US011950591B2

(12) United States Patent
Ramsey et al.

(10) Patent No.: US 11,950,591 B2
(45) Date of Patent: Apr. 9, 2024

(54) CONTAINER WITH BIOLOGICAL MATERIALS HAVING MULTIPLE SEALED PORTIONS

(71) Applicant: Instant Systems, Inc., Norfolk, VA (US)

(72) Inventors: Tara C. Ramsey, Norfolk, VA (US); Uzair Rajput, Norfolk, VA (US)

(73) Assignee: Instant Systems, Inc., Norfolk, VA (US)

(*) Notice: Subject to any disclaimer, the term of this patent is extended or adjusted under 35 U.S.C. 154(b) by 0 days.

(21) Appl. No.: 18/014,470

(22) PCT Filed: Jun. 10, 2022

(86) PCT No.: PCT/US2022/032931
§ 371 (c)(1),
(2) Date: Jan. 4, 2023

(87) PCT Pub. No.: WO2022/261389
PCT Pub. Date: Dec. 15, 2022

(65) Prior Publication Data
US 2023/0189793 A1    Jun. 22, 2023

Related U.S. Application Data

(60) Provisional application No. 63/209,712, filed on Jun. 11, 2021.

(51) Int. Cl.
*A01N 1/02* (2006.01)
*B65D 75/30* (2006.01)
*B65D 75/52* (2006.01)

(52) U.S. Cl.
CPC ........... *A01N 1/0273* (2013.01); *B65D 75/30* (2013.01); *B65D 75/527* (2013.01)

(58) Field of Classification Search
CPC ........... B65D 75/5805; B65D 75/5855; B65D 75/58; B65D 25/08; B65D 81/3266;
(Continued)

(56) References Cited

U.S. PATENT DOCUMENTS 1,438,487 A * 12/1922 Greene .............. B65D 75/5822
222/215
2,775,082 A    12/1956 Vog
(Continued)

FOREIGN PATENT DOCUMENTS

CN    202313465 U    7/2012
EP    1 031 341    11/2003
(Continued)

OTHER PUBLICATIONS

International Search Report and Written Opinion for PCT/US2022/032931, dated Nov. 30, 2022.

*Primary Examiner* — Chun Hoi Cheung
(74) *Attorney, Agent, or Firm* — Ambrose, Mills & Lazarow, PLLC

(57) ABSTRACT

An apparatus is disclosed having a first layer coupled to a second layer via a plurality of seals to define a storage volume that is separable by at least one intermediate seal into a first volume and a second volume. The intermediate seal is applicable after a material is introduced into the storage volume storage. The apparatus includes a first opening into the storage volume and a second opening into the storage volume. The first opening and the second opening are positioned near opposite edges. The apparatus also includes a first frangible region positioned along the intermediate seal and configured for separation of the first volume and the second volume.

17 Claims, 28 Drawing Sheets

(58) Field of Classification Search
CPC .......... B65D 81/32; B65D 75/527; A61J 1/12; A61J 1/10
USPC .... 206/216, 823, 581, 730, 229, 484, 459.1, 206/459.5; 222/541.6
See application file for complete search history.

(56) References Cited

U.S. PATENT DOCUMENTS

| | | | |
|---|---|---|---|
| 2,864,492 A | 12/1958 | Lappala | |
| 2,884,988 A | 5/1959 | D'Angelo | |
| 3,254,828 A | 6/1966 | Hershey | |
| 3,326,450 A | 6/1967 | Langdon | |
| 3,339,826 A | 9/1967 | Beskind | |
| 3,548,723 A | 12/1970 | Sengewald | |
| 3,735,918 A | 5/1973 | Tundermann | |
| 3,749,237 A | 7/1973 | Dorton | |
| 3,754,700 A | 8/1973 | Bonk | |
| 4,035,304 A | 7/1977 | Watanabe | |
| 4,140,162 A | 2/1979 | Gajewski et al. | |
| 4,152,184 A | 5/1979 | Bacehowski | |
| 4,176,746 A | 12/1979 | Kooi | |
| 4,181,069 A | 1/1980 | Porter | |
| 4,305,503 A | 12/1981 | Membrino | |
| 4,335,770 A * | 6/1982 | Kulle | A61J 1/10 383/29 |
| 4,344,557 A | 8/1982 | Lerner | |
| 4,479,989 A | 10/1984 | Mahal | |
| 4,548,023 A | 10/1985 | Danby et al. | |
| 4,550,831 A | 11/1985 | Whitford | |
| 4,561,110 A | 12/1985 | Herbert | |
| 4,581,007 A | 4/1986 | Kamp | |
| 4,616,760 A | 10/1986 | Kersten et al. | |
| 4,630,448 A | 12/1986 | Bilstad et al. | |
| 4,635,294 A | 1/1987 | Bentsen | |
| 4,693,701 A | 9/1987 | deBin | |
| 4,699,607 A | 10/1987 | Lambrecht | |
| 4,714,595 A | 12/1987 | Anthony et al. | |
| 4,863,285 A | 9/1989 | Claxton | |
| 4,887,715 A | 12/1989 | Spahn et al. | |
| 4,925,438 A | 5/1990 | Wagner | |
| 4,945,713 A | 8/1990 | Widenback | |
| 4,998,671 A | 3/1991 | Leifheit | |
| 5,007,744 A | 4/1991 | Scarberry et al. | |
| 5,031,762 A | 7/1991 | Heacox | |
| 5,088,994 A | 2/1992 | Porat et al. | |
| 5,114,004 A | 5/1992 | Isono et al. | |
| 5,118,202 A | 6/1992 | Bruno | |
| 5,160,329 A | 11/1992 | Oxley | |
| 5,209,745 A | 5/1993 | Irr et al. | |
| 5,221,567 A | 6/1993 | Baker | |
| D337,382 S | 7/1993 | Wallace | |
| 5,226,858 A | 7/1993 | Snowdon | |
| 5,236,088 A | 8/1993 | Dhority et al. | |
| 5,253,754 A * | 10/1993 | Soodak | A01N 1/0268 493/189 |
| 5,266,140 A | 11/1993 | Kohno | |
| 5,309,698 A | 5/1994 | Huseman | |
| 5,360,413 A | 11/1994 | Leason et al. | |
| 5,370,221 A | 12/1994 | Magnusson | |
| 5,728,086 A | 3/1998 | Niedospial | |
| 5,804,265 A | 9/1998 | Saad et al. | |
| RE36,132 E | 3/1999 | Heacox | |
| 5,971,155 A | 10/1999 | Liang | |
| 6,022,344 A | 2/2000 | Meijer et al. | |
| 6,045,546 A | 4/2000 | Drago et al. | |
| 6,089,541 A | 7/2000 | Weinheimer et al. | |
| 6,127,009 A | 10/2000 | Strassmann | |
| 6,149,302 A | 11/2000 | Taheri | |
| 6,176,371 B1 | 1/2001 | Tyrrell | |
| 6,238,090 B1 | 5/2001 | Yuter | |
| 6,287,284 B1 | 9/2001 | Warburton-Pitt | |
| 6,367,634 B1 | 4/2002 | Lynn et al. | |
| 6,375,613 B1 | 4/2002 | Brasile | |
| 6,394,993 B1 | 5/2002 | Chang et al. | |
| 6,398,771 B1 | 6/2002 | Gustafsson et al. | |
| 6,419,392 B1 | 7/2002 | Baker | |
| 6,422,753 B1 | 7/2002 | Thomas | |
| 6,523,698 B1 | 2/2003 | Dennehey et al. | |
| 6,579,008 B2 | 6/2003 | Price et al. | |
| 6,648,133 B1 | 11/2003 | Blaschke et al. | |
| 6,730,071 B1 | 5/2004 | Dassa | |
| 6,773,425 B1 | 8/2004 | Tamari | |
| 6,945,695 B2 | 9/2005 | Rabiea | |
| 7,051,879 B2 * | 5/2006 | Ramet | B65D 35/22 206/823 |
| 7,121,064 B2 | 10/2006 | Ausnit | |
| 7,354,426 B2 | 4/2008 | Young | |
| D595,842 S | 7/2009 | Haga et al. | |
| 7,594,578 B2 | 9/2009 | Smith et al. | |
| 7,670,384 B2 | 3/2010 | Kumar et al. | |
| 7,674,039 B2 | 3/2010 | McMahon et al. | |
| 7,770,611 B2 | 8/2010 | Houwaert et al. | |
| 7,810,667 B2 | 10/2010 | Douglas et al. | |
| 7,875,015 B2 | 1/2011 | Pahlberg et al. | |
| 8,038,348 B2 | 10/2011 | Lerner et al. | |
| 8,136,330 B2 | 3/2012 | Ostler et al. | |
| 8,267,912 B2 | 9/2012 | Ferris | |
| 8,287,680 B2 | 10/2012 | Foucaut et al. | |
| 8,591,391 B2 | 11/2013 | Chavarria et al. | |
| 8,597,223 B2 | 12/2013 | D'Ayot et al. | |
| D705,443 S | 5/2014 | Ichimura et al. | |
| 9,095,499 B2 | 8/2015 | Kugelmann et al. | |
| 9,155,606 B2 | 10/2015 | Benoit et al. | |
| 9,198,830 B2 | 12/2015 | Kugelmann et al. | |
| 9,796,166 B2 | 10/2017 | Verri et al. | |
| 9,879,217 B2 | 1/2018 | Coupier | |
| 9,926,524 B2 | 3/2018 | Clark et al. | |
| 9,962,898 B1 | 5/2018 | Russell et al. | |
| 9,974,528 B2 | 5/2018 | Taylor et al. | |
| 10,111,739 B2 | 10/2018 | Benoit et al. | |
| 10,582,994 B2 | 3/2020 | Kapec et al. | |
| 11,058,530 B2 | 7/2021 | Chen et al. | |
| 11,065,095 B2 | 7/2021 | Alden et al. | |
| 11,155,374 B2 * | 10/2021 | Thesing | B65B 9/2056 |
| 11,332,282 B2 | 5/2022 | Murray | |
| 2002/0130093 A1 | 9/2002 | Ferrara, Jr. et al. | |
| 2003/0009989 A1 * | 1/2003 | Knoerzer | B65B 9/2028 53/551 |
| 2003/0075474 A1 * | 4/2003 | Moyer | A61B 50/33 206/570 |
| 2003/0089084 A1 | 5/2003 | Ausnit | |
| 2004/0134166 A1 | 7/2004 | Ausnit | |
| 2004/0161167 A1 | 8/2004 | Ausnit et al. | |
| 2005/0261659 A1 | 11/2005 | Mizuo et al. | |
| 2005/0271307 A1 | 12/2005 | Pawloski et al. | |
| 2006/0024818 A1 | 2/2006 | Conconi | |
| 2007/0074980 A1 | 4/2007 | Bankoski et al. | |
| 2007/0092398 A1 | 4/2007 | McDonald | |
| 2007/0206888 A1 | 9/2007 | Chang | |
| 2008/0017543 A1 | 1/2008 | Pahlberg et al. | |
| 2008/0214998 A1 | 9/2008 | Kurek et al. | |
| 2008/0234654 A1 | 9/2008 | McCarthy et al. | |
| 2008/0254171 A1 | 10/2008 | Bordano | |
| 2008/0285896 A1 | 11/2008 | Taheri | |
| 2008/0304771 A1 | 12/2008 | Harder et al. | |
| 2009/0030396 A1 | 1/2009 | Ferris | |
| 2009/0034885 A1 * | 2/2009 | McGruder | B65D 33/25 383/38 |
| 2009/0105684 A1 | 4/2009 | Balteau et al. | |
| 2009/0238495 A1 | 9/2009 | Anderson | |
| 2010/0040308 A1 | 2/2010 | McLellan et al. | |
| 2011/0308977 A1 | 12/2011 | DiLiberto et al. | |
| 2011/0308992 A1 * | 12/2011 | Bahcall | B65D 75/566 206/812 |
| 2012/0195533 A1 | 8/2012 | Mead | |
| 2013/0209000 A1 | 8/2013 | Owensby et al. | |
| 2013/0281964 A1 | 10/2013 | Kugelmann et al. | |
| 2015/0216763 A1 | 8/2015 | Fearnot | |
| 2016/0000062 A1 | 1/2016 | Chen et al. | |
| 2016/0052690 A1 | 2/2016 | Bolhous et al. | |
| 2016/0137354 A1 | 5/2016 | Sargin | |
| 2016/0177245 A1 | 6/2016 | Johnson et al. | |
| 2016/0228231 A1 | 8/2016 | Southard et al. | |
| 2016/0305577 A1 | 10/2016 | Huschke | |

(56)  References Cited

U.S. PATENT DOCUMENTS

| | | |
|---|---|---|
| 2017/0001782 A1 | 1/2017 | Arent et al. |
| 2017/0121061 A1 | 5/2017 | Sprehe et al. |
| 2017/0172847 A1 | 6/2017 | Platenkamp et al. |
| 2017/0181426 A1 | 6/2017 | Wolf et al. |
| 2017/0202740 A1 | 7/2017 | Yoshida et al. |
| 2018/0154289 A1 | 6/2018 | Rhodes |
| 2018/0249703 A1 | 9/2018 | Llyin |
| 2020/0008921 A1* | 1/2020 | Alden .................. A01N 1/0273 |
| 2020/0061365 A1 | 2/2020 | Alden et al. |
| 2021/0298888 A1 | 9/2021 | Alden et al. |
| 2022/0273464 A1 | 9/2022 | Rister et al. |
| 2022/0305738 A1* | 9/2022 | Ramsey ............. B65D 75/5855 |
| 2023/0233309 A1 | 7/2023 | Alden et al. |

FOREIGN PATENT DOCUMENTS

| | | |
|---|---|---|
| WO | WO 1997/042897 | 11/1997 |
| WO | WO 2002/041824 | 5/2002 |
| WO | WO 2017/026131 | 2/2017 |
| WO | WO 2020/014162 | 1/2020 |

* cited by examiner

CONTAINER WITH BIOLOGICAL MATERIALS HAVING MULTIPLE SEALED PORTIONS

CROSS-REFERENCE TO RELATED APPLICATIONS

This application is a U.S. national stage filing under 35 U.S.C. § 371 of International Application No. PCT/US2022/032931, filed Jun. 10, 2022, entitled "Container for Biological Materials Having Multiple Sealed Portions," which claims priority to U.S. Provisional Application Ser. No. 63/209,712, entitled "Multi-Use Container for Biological Materials and Compounded Pharmaceuticals," filed Jun. 11, 2021, each of which is incorporated herein by reference in its entirety.

BACKGROUND

The embodiments described herein relate to containers for storing, handling, packaging, and transporting material. Specifically, the embodiments described herein relate to containers for containing biological materials that have one or more seals that define multiple portions, some of which can be easily removed.

Known biological materials are used in a variety of procedures to perform medical procedures. Such procedures can include implanting bone or gum tissue to address dental or periodontal issues, bone grafting to repair fractures, and tendon grafting to repair damaged ligaments and/or tendons (e.g., repair of a torn anterior cruciate ligament), to name just a few. In many instances, the tissue implant is not taken from the patient's body (i.e., is not an autograft), but rather is from another source, such as from a human cadaver (i.e., an allograft) or an animal (i.e., a xenograft). Known non-autologous grafts are often stored in a dried condition within a sterile package, and thus must be rehydrated or otherwise prepared prior to use.

Some known storage containers include a port that can be coupled to a tube set to allow fluids to be conveyed into or out of the container (e.g., to rehydrate the material stored within the container). In some instances, the port can also allow ingress or egress of flowable biological materials, such as bone chips, bone paste, blood, or cells (within a liquid medium). Many known ports include a tubular member that is sealed between opposing layers of material from which the container is constructed, and that extends from an end of the container. The inclusion of such ports increases the overall size of the container, thus such containers can require a greater volume for storage (e.g., for cold storage). This can reduce the storage capacity, which increases costs and decreases efficiency.

A port that extends from the end of the container, and which is often more rigid than the remainder of the container, can also contact surrounding structures during handling. For example, some known containers include ports that can catch on a shoulder or surface of storage containers or otherwise be subjected to external forces during handling. Accordingly, the port can be a point of failure for the container.

In addition to storing grafts, known containers are also used for storage, handling, and processing of blood, cells, and other liquid biological materials. Some cell processing and handling systems include multiple containers coupled together (e.g., via a tube set) so that desired amounts of the cells can be stored in separate locations. For example, some systems include different containers for holding harvested cells removed from a culture that need to be washed separate from cells that have been washed and are ready for storage. Because some biologic materials, such as blood and cells, require quality testing of samples (e.g., to ensure that the materials are appropriate for the desired use), some known systems include separate containers for holding quality control ("QC") samples separately from the primary storage container. In use, the QC containers are often filled separately from the primary storage container by switching valves, tubes, or other fluid pathways during processing. Such known systems and methods, however, can be cumbersome and time consuming to properly separate the QC sample. Moreover, such known system can sometimes result in errors in ensuring that the QC sample is associated with the primary portion of the material (e.g., due to errors in valving, switching tubes, and the like).

Thus, a need exists for improved containers and methods for storing, transporting, and/or processing, units of biological material including improving quality control of the materials, improving the robustness of the storage of the materials, and dispersing the materials from the storage containers. Additionally, a need exists for better quality control of materials stored in containers and containers that facilitate that quality control.

SUMMARY

Material storage systems are described herein along with containers and methods for storing materials including tissue and other biological materials. In some embodiments, the system includes a first layer and a second layer. The first layer and second layer are coupled together to form a container having a first end portion, a second end portion, a first edge between the first end portion and the second end portion, and a second edge between the first end portion and the second end portion, the first edge opposite the second edge. The system includes a plurality of seals coupling the first layer and the second layer together along at least the first end portion, the second end portion, the first edge, or the second edge to define a storage volume between the first layer and the second layer. The system includes a first opening into the storage volume, with the first opening being positioned at the first end portion. The system includes at least one intermediate seal extending between the first edge and the second edge that separates the storage volume into a first volume and a second volume. The intermediate seal is applicable after a material is introduced into the storage volume such that the target material is stored within the first volume and the second volume. The system includes a frangible region extending along the intermediate seal that allows for physical separation of the container into a first container portion that includes the first volume and a second container portion that includes the second volume.

In some embodiments, the frangible region includes any of a perforation, a tear notch, or a stress concentration riser. In some embodiments, the frangible region includes a stress riser in the first layer and the second layer to initiate a tear along the frangible region. In some embodiments, the frangible region includes a first perforation defined in the first layer and a second perforation defined in the second layer, the first perforation aligned with the second perforation. In some embodiments, a width of the intermediate seal is greater than a width of the frangible region. The frangible region is proximal to the second end portion and is configured to allow removal of the second container portion by hand (i.e., without any external tools, such as a cutting blade or scissors).

In some embodiments, a first seal of the plurality of seals is located along the first edge and a second seal of the plurality of seals is located along the second edge. The system includes a port positioned along the first end portion that defines the opening. In some embodiments, the first end portion includes an end portion seal and an end portion frangible region that is configured such that in response to separation at the end portion frangible region, the port is removed from the storage volume.

In some embodiments, the second end portion includes an end portion seal that is applicable after the material is introduced to the storage volume. The end portion seal fluidically isolates the second opening from the storage volume.

In some embodiments, either of the second edge or the second container portion includes a tapered portion. The tapered portion extends from the first end portion to the second end portion of the container. Alternatively, the tapered portion extends from an end of the second edge to a tip at the second end portion. The second container portion includes the length of the tapered portion. In some embodiments, the opening into the container is a first opening and the plurality of seals coupling the first layer and the second layer includes a peelable seal at the tip. The peelable seal is configured such that the first layer can be peeled away from the second layer to produce a second opening at the tip.

In some embodiments, the first volume or the second volume are partially defined by one or more of the plurality of seals and the intermediate seal completes a closure to fully isolate the first volume and the second volume from one another. The frangible region is proximal to the second end portion and is configured to remove the tapered portion while maintaining the plurality of seals of the first container portion and the second container portion keeping them enclosed.

In some embodiments, the first volume is larger than the second volume. The first volume is more than twice the size of the second volume. In some embodiments, both the first volume and the second volume include regions that are openable to remove the material from each of the first volume and the second volume. The first volume includes a port and the second volume include a peelable region. The second container portion includes a plurality of graduated markings that indicate quantity of the material stored therein. The second volume is larger than the first volume.

In some embodiments, the first container portion includes a first indicium associated with the target material and the second container portion includes a second indicium associated with at least one of the first indicium, the first container portion, or the target material.

In some embodiments, the second volume includes a plurality of ports extending to an exterior of the container. At least one of the first layer or the second layer includes a separation tab extending from an exterior portion of the first layer or the second layer and oriented such that a user can grip the tab and separate the first layer from the second layer.

In some embodiments, a storage container includes a first layer and a second layer. The first layer and second layer are coupled together to form a container having a first end portion, a second end portion, a first edge between the first end portion and the second end portion, and a second edge between the first end portion and the second end portion. The first edge is opposite the second edge. The storage container includes a plurality of seals coupling the first layer and the second layer together along at least the first end portion, the second end portion, the first edge, or the second edge to define a storage volume between the first layer and the second layer. The storage container includes a port coupled to the first end portion of the container that defines an opening into the storage volume. The storage container includes an end portion seal at the first end portion of the container that fluidically isolates the port from the storage volume. The storage container includes an end portion frangible region extending between the first edge and the second edge along of the end portion seal. The end portion frangible region is configured for physically separating the port from the storage volume while keeping the storage volume isolated.

In some embodiments, the storage container includes an at least one intermediate seal extending between the first edge and the second edge, the storage volume being separable into a first volume and a second volume by the at least one intermediate seal. The intermediate seal is applicable after a material is introduced into the storage volume. The storage container includes an intermediate frangible region extending along the at least one intermediate seal that allows for physical separation between the first volume and the second volume defining a first container portion storing the material and a second container portion storing the material. The first volume or the second volume are partially defined by one or more of the plurality of seals and the at least one intermediate seal completes a closure to fully isolate the first volume and the second volume from one another. The intermediate frangible region includes a stress riser in the first layer and the second layer to initiate a tear along the intermediate frangible region.

In some embodiments, the second end portion includes an end portion seal that is applicable after the material is introduced to the storage volume. The end portion seal is a peelable seal. The storage container tapers along the second edge extending from the first end portion to the second end portion. The storage container tapers from an end of the second edge to the second end portion. The second container portion includes the length of the tapered portion of the storage container.

In some embodiments, the frangible region is proximal to the second end portion and is configured to remove the tapered portion forming an opening into the first container portion. The end portion frangible region is proximal to the second end portion and is configured to remove the tapered portion while maintaining the plurality of seals keeping the first container portion and the second container portion enclosed.

In some embodiments, the tapered region includes graduated markings that indicate quantity of a material stored therein. The second volume is larger than the first volume. The second volume includes a plurality of ports extending to an exterior of the container. At least one of the first layer or the second layer includes a separation tab extending from an exterior portion of the first layer or the second layer and oriented such that a user can grip the tab and separate the first layer from the second layer.

In some embodiments, a method of storing a material includes providing a storage container having a storage volume defined between a first layer of the storage container and a second layer of the storage container. The storage container includes an opening. The method includes inserting the material into the storage volume via the opening. The method includes sealing the opening to enclose the storage volume. The method includes applying an intermediate seal separating the storage volume into a first volume and a second volume with the material being in both the first volume and the second volume. In some embodiments, the storage container includes a frangible region along the intermediate seal allowing the first volume and the second volume to be physically separated by hand along the frangible region. The method optionally includes separating the first volume from the second volume along the frangible region located along the intermediate seal. Additionally, or alternatively, the method can include separating and storing the second volume for future reference to the material stored therein. This allows ongoing testing and verification of the material to understand what material was used in the first volume. Additionally, or alternatively, the method can include dispending the material from either the first volume or the second volume. The material can be used, tested, or stored. Since both volumes contain materials that match the other volume, one can serve as a reference material after the other volume is used.

DETAILED DESCRIPTION

Figure 1A:
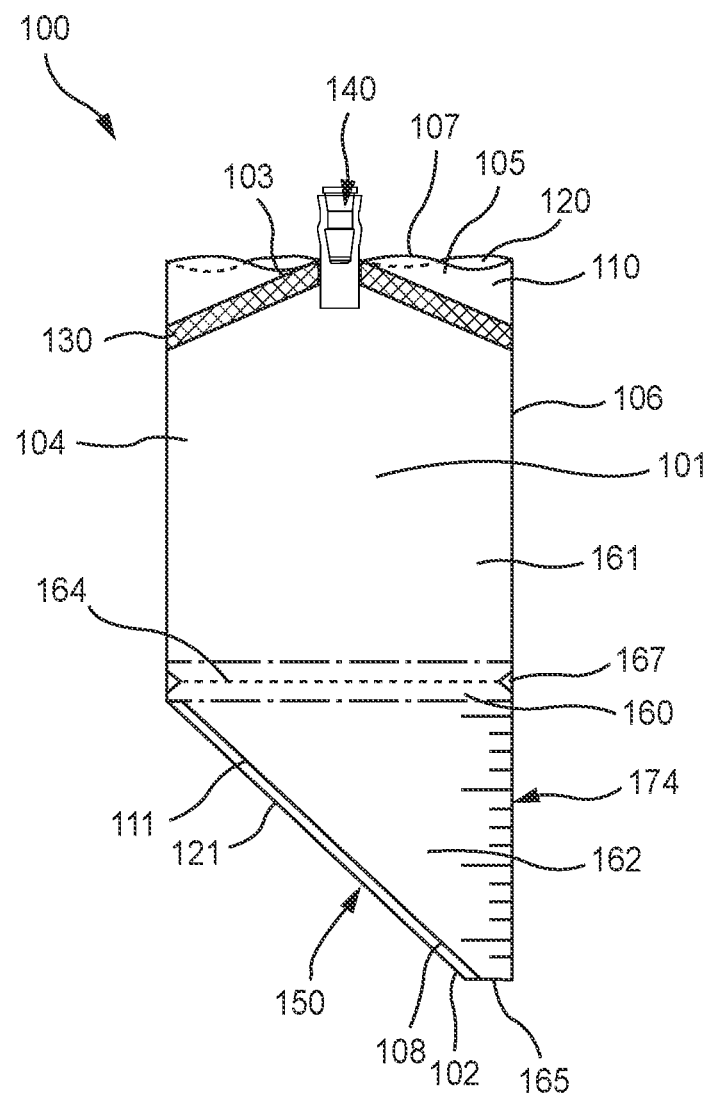
FIG. 1A is a schematic illustration of a storage container according to an embodiment.

The embodiments described herein related to a storage container that can advantageously be used with a wide variety of materials for transportation, processing and/or implantation operations associated with the materials. In particular, the storage containers described herein can allow for material (e.g., a tissue specimen, biologic material, etc.) to be loaded and sealed at the point of loading (e.g., a tissue bank, a cell culturing system, or the like). The storage containers described herein can further facilitate efficient transportation and storage of the materials therein by allowing a port or other portions of the container to be removed while maintaining the stored material in a hermetically sealed (or fluidically isolated) condition. The storage containers described herein can further facilitate quality control ("QC") testing and record keeping of QC test results by allowing a predetermined volume of the storage container to be removed from the primary storage portion after the container has been filled with the material.

In some embodiments, multiple stored product can be stored within respective storage volumes of the storage container, transported together as part of the same storage container, and frozen together as part of the same storage container (e.g., cryogenically frozen down to about −200° C.). In some embodiments, the entire storage container is thawed. In some embodiments, one or more of the separable storage container portions of the storage container can be removed from the storage container and processed individually (e.g., thawed, subjected to QC testing, stored in a sample record keeping facility). In some embodiments, unused separable storage containers of the storage container can be re-frozen, transported to a different facility, or otherwise maintained for viable use. In some embodiments the storage container can be inserted into an overwrap or into one separable storage containers of a multi-chamber overwrap assembly.

In some embodiments, a method of rehydrating a tissue specimen includes conveying a rehydration fluid into a storage volume defined between a first layer of a storage container and a second layer of the storage container. The rehydration fluid is conveyed via a port coupled to the storage container. The storage volume contains a tissue specimen hermetically sealed therein, and, in some embodiments, the tissue specimen is supported by a support structure. A stiffness of the support structure is greater than each of a stiffness of the first layer and a stiffness of the second layer. The rehydration fluid is maintained within the storage volume to rehydrate the tissue specimen. The first layer is then peeled from the second layer to expose the storage volume. The method further includes removing the rehydrated tissue specimen from the storage volume after the first layer is peeled.

In some embodiments, a method of processing a biologic material (e.g., cells, blood, or the like) includes conveying the biologic material into a storage volume defined between a first layer of a storage container and a second layer of the storage container. The biologic material is conveyed via a port coupled to the storage container. After the biologic material is within the storage volume, an end portion seal is produced to fluidically isolate the storage volume from the port. The port (and any portions of an end portion of the storage container to which the port is coupled) is removed from the remainder of the storage container by separating the port (and any portions of an end portion of the storage container to which the port is coupled) via a frangible region along the end portion seal. The separation via the frangible region can be performed by hand (i.e., without the use of a cutting blade, machinery or equipment). In some embodiments, the frangible region can include a perforation, a tear notch, or a stress concentration riser.

As used herein, the term "about" when used in connection with a referenced numeric indication means the referenced numeric indication plus or minus up to 10% of that referenced numeric indication. For example, the language "about 50" covers the range of 45 to 55. Similarly, the language "about 5" covers the range of 4.5 to 5.5.

As used herein, the term "tissue specimen" or "tissue graft" refers to any material that can be used in a tissue repair procedure or other procedures which use tissue grafts (e.g., birth tissue used as patch for healing then removed). Thus, a tissue specimen or a tissue graft can include any of a skin graft, bone tissue, fiber tissue (e.g., tendon tissue, ligament tissue, or the like), ocular tissue (e.g., corneal implants), birth tissue (e.g., amnion graft), cardio vascular tissue (e.g., heart valve) or the like. A tissue specimen or a tissue graft can include a portion of tissue harvested from a donor or a structure component that includes both tissue and non-tissue material (e.g., a synthetic matrix that includes tissue therein). For example, a tissue specimen or a tissue graft can include bone tissue that also includes bone cement or other non-tissue components. As another example, a tissue specimen or tissue graft can include bone chips including cortical bone chips, cancellous bone chips, and corticocancellous bone chips, and/or bone chips with viable bone lineage committed cells.

used herein, the term "biologic material" refers to any material that is produced or derived from a living (or recently living) organism. Biologic materials can include, for example, tissues, cells, blood, or other bodily fluids. Biologic materials can also include plants, plant products, micoorganisms, genetically modified organisms (including cells and cell lines). Biologic materials can also include DNA or RNA (including plasmids, oligonucleotides, cDNA) or viral vectors.

As used in this specification, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes include various spatial device positions and orientations.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

The storage containers discussed herein including any suitable package, pouch, bag, or container assemblies (e.g., storage containers 100, 200, 300, 400, 500, 600, 700, 800, 900, 1000) includes internal volumes configured to suitably store one or more of the materials 50. The storage containers (e.g., storage containers 100, 200, 300, 400, 500, 600, 700, 800, 900, 1000) can include in some embodiments a flexible material defining a flexible container. In some embodiments, the storage containers can include one or more rigid components.

As used herein the materials 50 can include compounded and non-compounded pharmaceuticals, a tissue or tissues, cellular material, biological material (including but not limited to biological material 50, as described herein), and/or related media (herein referred to together as stored product). In some embodiments, the container assemblies described herein can be used to store packages containing tissue, cellular material, biological material, or related media. In some embodiments, the stored product within internal volumes or within packages within internal volumes can include biologic materials, including but not limited to, human and animal tissues, human and animal cells or cellular materials, plant materials (tissue and cellular materials), organs, organoids, biologically sourced materials (e.g., printed tissues, cells, organs, or organoids), bacteria, viruses, viral vectors, fungi, medical devices, combination devices, material for homologous or non-homologous use, and/or materials for autologous or allogenic use. In some embodiments, the stored product can include cellular material, including but is not limited to, lineage committed and non-lineage committed cells (e.g., bone lineage committed cells, osteoblasts, osteocytes, etc.), differentiated cells or non-differentiated cells (e.g., muscle cells, endothelial cells, etc.), and/or genetically modified or non-genetically modified materials. Examples of human and animal tissues include, but is not limited to, birth tissues (e.g., amnion, cord, cord blood, chorion, placenta, etc.), bones and/or products made from bones (e.g., machined allografts, ground particles, etc.), bone sources (e.g., tibia, fibula, humerus, cranial flaps, radius, ulna, pelvic bones, and joints, etc.), brain tissue, cartilages (from all sources in bodies generally from knee joints, shoulders, etc.), fascia lata, heart valves, arteries, veins, nerves, organs (e.g., lungs, hearts, liver, kidneys, etc.), reproduction tissue (e.g., semen and eggs), ribs, soft tissues (e.g., all tendons, Achilles, patellar, etc.), skin, and/or tumors. Examples of the human or animal cellular materials include, but is not limited to, B-cells, blood cells and blood derived cells, bone cells, CAR-T cells, egg cells, engineered T-Cells, fat cells, muscle, cells, natural killer cells, nerve cells, sperm cells, stem cells (modified and un-modified, differentiated, and non-differentiated), T-cells, tumor infiltrating lymphocytes (TIL), viral vectors, viruses and bacteria. The human or animal cellular material can be modified or non-modified (such as genetically modified). Examples of the plant materials include, but is not limited to, cellulose, hemicellulose, pectin, fruit, fungi, leaves, mitochondria, plant organelles, pollen, roots, seeds, shoots, and/or stems. In some embodiments, the stored product can include related media, including but not limited to, culture media, saline solution, cryoprotectant, preservation solution, etc. It will be appreciated that any suitable stored product can be stored within any of the container assemblies described herein.

An embodiment of a storage container 100 is shown in FIG. 1A. The storage container 100 (and any of the container assemblies described herein) includes a storage volume 101 that can be used to store the material 50 (e.g., e), and/or to perform any of the methods described herein and/or the methods of preparing the material 50 for use in a procedure. As described herein, the storage container 100 provides a container that can be used for cryogenically freezing, storage, transport, processing, defrosting and/or rehydration of the material 50. The storage container 100 also includes a first layer 110, a second layer 120 and one or more seals 130 connecting the first layer 110 and the second layer 120. The one or more seals 130 form side edges 104, 106 of the storage container 100. While sealed edges can define the storage container 100, it is also appreciated that in some embodiments, the two layers (e.g., 110, 120) can be provided as tubular material that is flattened forming two longitudinal connections between the layers on the flattened longitudinal edges of the tubular material (e.g., layflat tubular film). Said another way, the side edges 104, 106 need not be formed by the one or more seals 130.

As shown in FIG. 1, the storage container 100 includes one or more material ingresses and/or egresses. For example, the storage container 100 can include a first end portion 103 and a second end portion 102. The storage container 100 can include a first opening 141. The first opening can include any opening suitable to receive or expel the material 50 (or other fluids or flowable substances associated with the material 50, such as a wash solution, buffer, or rehydration solution). For example, the first opening can be defined by a port 140. In other examples the first opening 141 can include a capped opening, unattached layers, a resealable opening, or any other suitable passage for receiving or expelling the material 50, The first opening is referred to herein as a port for simplicity. This should not be construed as limiting from other structural configurations for the opening. In some embodiments the port 140 is proximal to (extends from) the end portion 103. The storage container 100 can also or alternatively include a second opening (not shown). The second opening can include any opening suitable to receive or expel the material 50. For example, the second opening can include an edge opening defined by a portion where the layers defining the container are unattached.

In some embodiments, the first opening is defined by the port 140. For example, as shown in FIG. 1A, the two layers (e.g., the first layer 110, the second layer 120) respectively are joined at a first end portion 103 with the port 140 therebetween, and the two side edges 105, 107 at the first end portion 103 are joined together. Thus, the port 140 is coupled to the first end portion 103 of the storage container 100 and is configured to allow fluid communication between the outside of the storage container 100 and the storage volume 101 that is defined between the first layer 110 and the second layer 120. In this manner, the material can be inserted or additionally or alternatively treated (e.g., with a preservation fluid) after being conveyed into the storage container 100 via the port 140. Additionally or alternatively, the port 140 can also be coupled to a vacuum source to evacuate the storage volume. Additionally or alternatively, when in use (e.g., during a surgical procedure), the port 140 can allow for cryogenically defrosting the material 50. Additionally or alternatively, when in use (e.g., during a surgical procedure), the port 140 can allow for inflow of fluid for rehydration or other purposes. Additionally or alternatively, when in use, the port 140 can allow for removal of fluid.

The port 140 can be any suitable port that selectively provides fluid communication to the storage volume 101. For example, the port 140 can include a tube, a valve, and/or a cap. In some embodiments, the port 140 can be a needle-free port. In some embodiments, the port 140 can be a swabable connector. Similarly stated in some embodiments, the port 140 can have external surfaces and can be devoid of recesses or crevices such that the port 140 can be easily wiped or "swabbed" to maintain sterility during use. In some embodiments, the port 140 can include any of the barbed, swabable valves produced by the Halkey-Roberts Corporation, such as the 2455 series of swabable valves. In other embodiments, the port 140 (and any of the ports described herein) need not be either a swabable connector or a needle-free port; any suitable port can be employed. In some embodiments, the port 140 can include a male or female luer fitting. In some embodiments, the port 140 can include a threaded connection for coupling with a syringe or a tubing set or a cap. In some embodiments, the port 140 can be sealed at the end for sterile docking or cutting.

Although the port 140 is shown as being coupled at the first end portion 103 of the storage container 100. In other embodiments, the port 140 (and any of the ports described herein) can be coupled at any location and to any portion of the storage container 100. For example, in some embodiments, the port 140 (and any of the ports described herein) need not be coupled to the first end portion 103 of the storage container 100, the port can be on the surface or another edge portion of the storage container 100. The port 140 (and any of the ports described herein) can be offset from a center line of the storage container 100. For example, in some embodiments, the port can be located at a corner of the container. In some embodiments, the port (and any of the ports described herein) can be coupled around a central portion of the container.

In some embodiments, the port 140 can include a filter. In some embodiments, the port 140 can include a Y-connector. The base of Y-connector near port can contain the filter. One end of Y-connector can be sealed. The other end of the Y-connector can be threaded port for syringe connection. This allows for both hospital uses (e.g., syringe connection to port) and lab uses (e.g., a sterile dockable connection to the port). In some embodiments, the material 50 stored in the storage volume 101 does not or is limited in its ability to move through the port 140. This may be due to size, viscosity, or other characteristics. In such embodiment, the port can be filter-less allowing the material 50 to move into or out of the volume without regard to the material 50 stored therein.

Figure 1B:
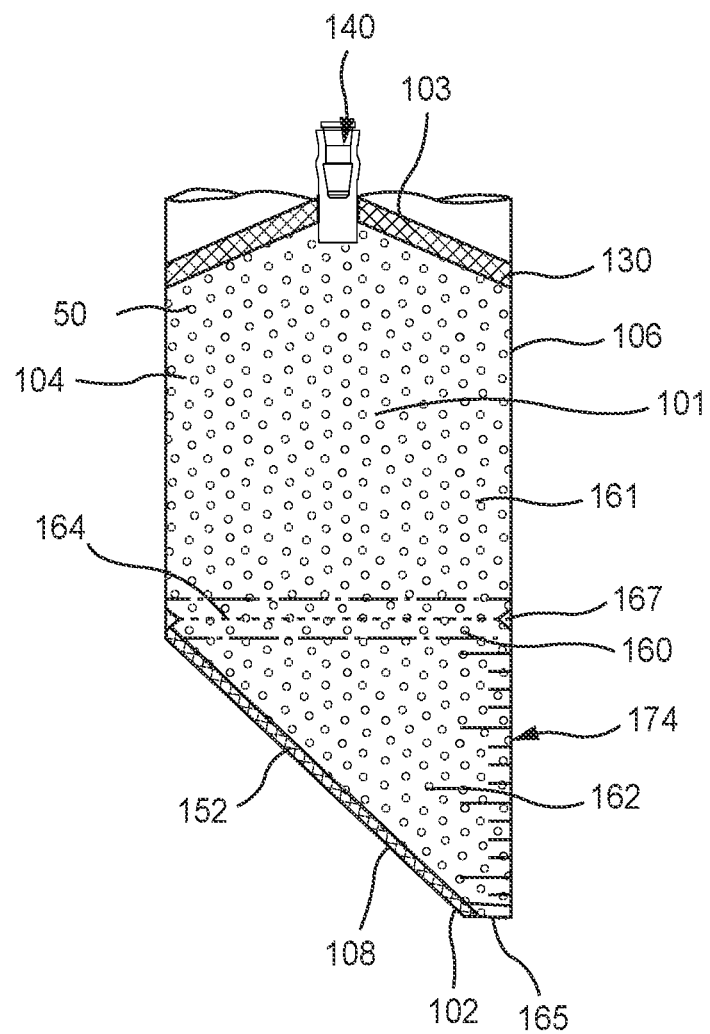
FIG. 1B is a schematic illustration of the storage container according to FIG. 1A filled with a material.

In some embodiments, as illustrated in FIG. 1A, in a first (or opened) configuration, one or more edges (e.g., edge 111) of the first layer 110 are spaced apart from one or more edges (e.g., edge 121) of the second layer 120 to define a second opening 150 into the storage volume 101 of the storage container 100. The opening 150 can be of any suitable size to facilitate loading of the material 50 (including e.g., tissue, biological material and/or treatment therapeutics) such that the volume 101 can receive the material 50. In this manner, such embodiments of the storage container 100 can receive materials that cannot be conveyed into the storage volume 101 via the port 140 (or the first opening 141). In some embodiments, the second opening 150 can extend across a portion of the length of an end or a side of the storage container 100. In some embodiments, the opening 150 can extend across substantially all of the end or side of the storage container 100. In the example shown in FIG. 1A, the second opening 150 can extend across the edge 108 of the storage container 100 defined by the separation between edges 111 and 121. This opening can be larger than a ported opening, such as the port 140 discussed above. A larger opening can allow for input of a larger material (e.g., a tissue graft) into the storage volume 101. Although it is appreciated that other materials as discussed herein can additionally or alternatively be introduced through opening 150. After the material 50 is introduced into storage volume 101, the opening 150 can be sealed by a seal 152 as shown in FIG. 1B. Sealing the second opening 150 by seal 152 encloses storage volume 101 isolating the material 50 therein. This allows for the loading of biologicals or other materials through the second opening 150 opposite the port 140. Once loaded, the second opening 150 is sealed. The seal can be performed by a heat seal, an adhesive, or other suitable methods. In some embodiments, a laser line guides the sealing of the opening.

Figure 1C:
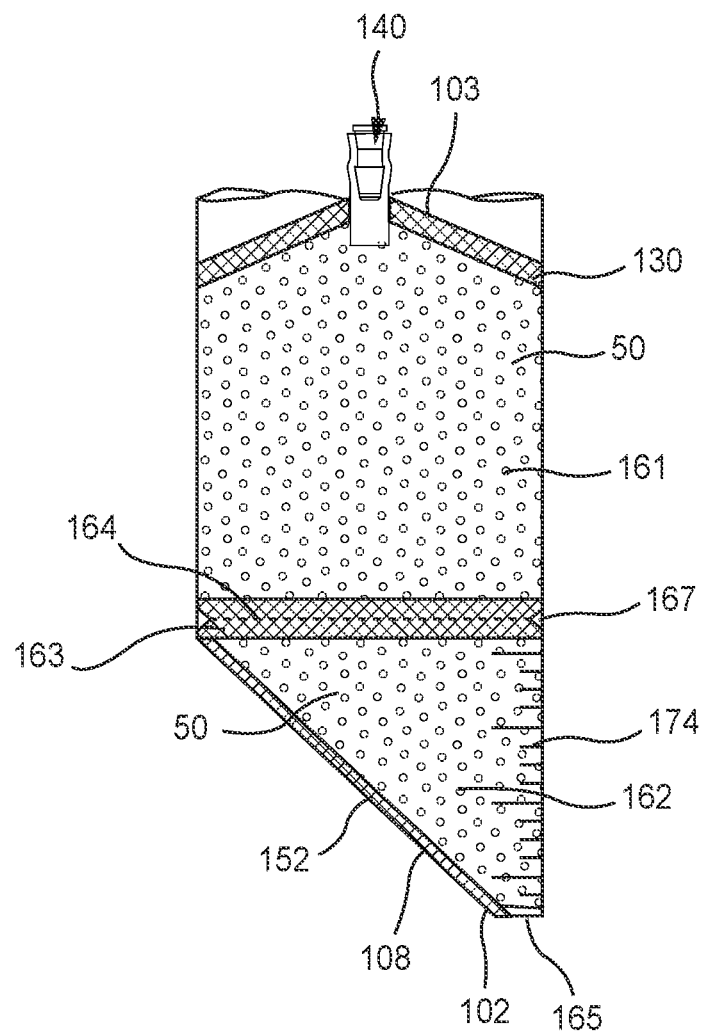
FIG. 1C is a schematic illustration of the storage container according to FIG. 1A with an intermediate seal.
Figure 1D:
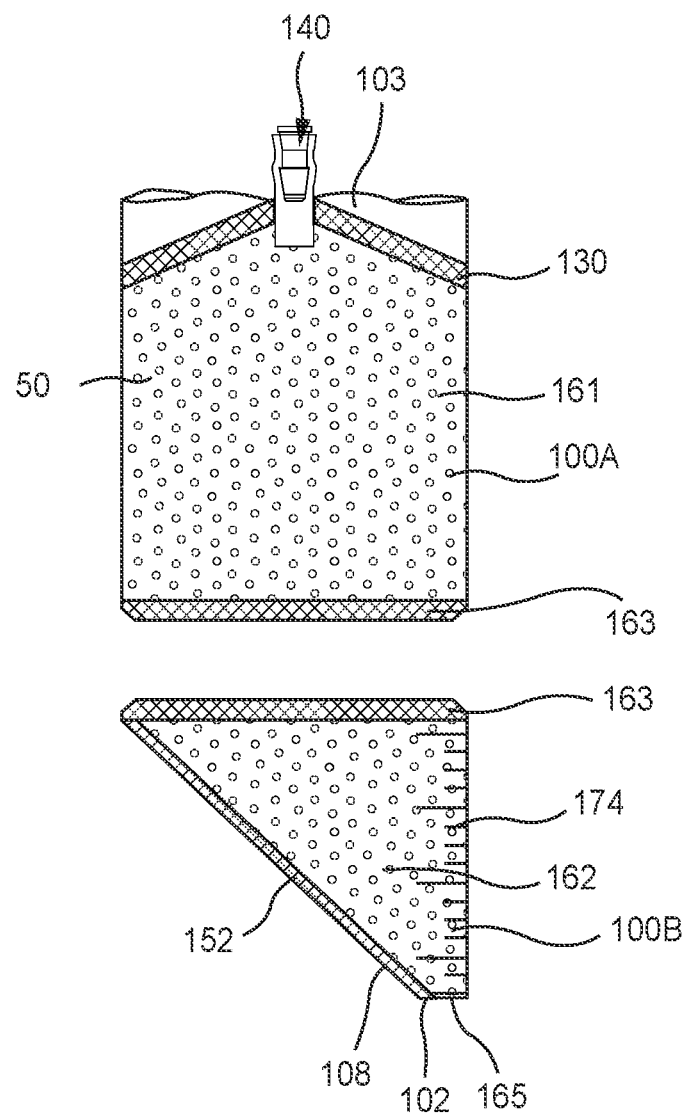
FIG. 1D is a schematic illustration of the storage container according to FIG. 1A showing a first volume and second volume separated.
Figure 1E:
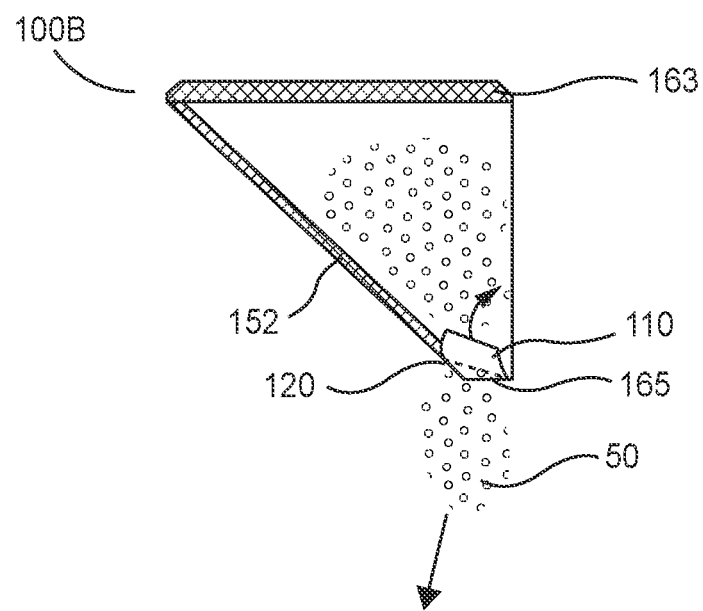
FIG. 1E is a schematic illustration of the storage container according to FIG. 1A showing dispensing the material from the second volume.

In some embodiments, the container is suitable for segregating the material 50 into multiple portions. For example, the storage container 100 can include a sealable region 160 (FIG. 1B), suitable to apply (or produce) an intermediate seal 163 (e.g., the intermediate seal 163 in FIG. 1C) to separate the storage volume 101 into a first volume 161 and a second volume 162. In some embodiments, the intermediate seal 163 is applied after the material 50 has been introduced into the storage volume 101. The intermediate seal 163 is applied or produced by any suitable procedure or mechanism, such as via a heat seal, a pressure seal, a laser weld, an adhesive seal, or any other suitable sealing procedures. The sealable region 160 can include indicia or other markings to indicate to the user loading the material 50 into the storage container 100 where to apply the intermediate seal 163. When sealed at the indicia, the volume on a first side of the seal will have a first predetermined volume (e.g., volume 161) and the volume on the other side of the seal has a second predetermined volume (e.g., volume 162). In this way, one portion of the material 50 (e.g., the material in volume 161) is usable for the intended process or operation while the other portion of the material 50 (e.g., the material contained in volume 162) can be stored for subsequent use (e.g., quality control, testing, archiving, etc.) Separating the material 50 into two portions allows for second portion in volume 162 to be a known sample that is the same (i.e., that is from the same batch, that has been subjected to the same processing, and/or that is filled at the same time) as the first portion in volume 161 for exact match retention. In other words, the material 50 within the volume 161 has substantially identical properties as the material 50 within the volume 162. In various embodiments, second portion in the volume 162 is a quality control sample that is fully representative of the portion stored in volume 161. In some embodiments, the volume 161 is the larger volume as shown in FIG. 1C-1E. Contrarily, in some embodiments, the volume 162 is the larger volume. In this alternative, the larger volume can be used for significant subsequent testing using more material than the actual procedure. The second portion can be stored and subsequently tested to show first portion meets certain criteria. In some embodiments, the second portion could be about 5 cubic centimeters to about 50 cubic centimeters in volume.

In some embodiments, the sealable region 160 includes a frangible region 164. The frangible region can be suitable to facilitate or initiate separation of volume 161 from volume 162 as shown in FIG. 1D defining a first storage container 100A and a second storage container 100B. The frangible region 164 can include perforations, thinning of material, a tear notch 167 (that functions as a stress riser), or any other suitable mechanism for separating volumes 161 and 162 of the storage container 100 from one another. Specifically, in some embodiments, the frangible region 164 can facilitate separating the first storage container 100A from the second storage container 100B by hand (e.g., without a cutting blade, machinery, or other external equipment). For example, as shown in FIG. 1B, the frangible region 164 includes perforations and stress risers 167. In some embodiments, the frangible region 164 can include one or more perforations lines positioned between the storage volume 161 and the storage volume 162. When the frangible regions are separated volume 162 is removable from the volume 161 without compromising the sealed structure of either of the volumes defining the first storage container 100A and the second storage container 100B. Specifically, as shown the width of the intermediate seal 163 is greater than the width of the frangible region 164. In some embodiments, the width of the intermediate seal 163 is at least two times than the width of the frangible region 164. In this manner the intermediate seal 163 will be maintained on the ends of each of the first storage container 100A and the second storage container 100B after the containers are separated.

While shown in FIG. 1D as a triangular section and a rectangular section, it will be appreciated that other shapes of the volumes, seals, and frangible regions are applicable as well. In some embodiments, the first volume 161 (which functions as the first container portion) and the second volume 162 (which functions as the second container portion) can be different shapes. For example, as shown in FIGS. 1A-1D, the first volume 161 can be generally rectangular. The second volume 162 can be tapered from one-side having a similar width to volume 161 to a narrower width on the opposite end of volume 162 at a tip 165 as shown in FIG. 1E. In some embodiments, the narrower width can be a point. In some embodiments, the narrower width can be a truncated end suitable to dispense the material through an opening as a defined flow (see FIG. 1E). The tapered portion with its narrow end can be opened thereby allowing the material within the second volume 162 to be dispensed in a controlled manner as shown in FIG. 1E. Without a port attached to the second volume 162, port leaking can be avoided, thus producing robust long-term storage. As shown in FIGS. 1A-1D, the first volume 161 can in some embodiments include the port 140, which remains coupled thereto, after separation from the second volume 162 allowing for the introduction and removal of fluids. In this manner, the first volume 161 (which functions as the first container portion 100A after the separation from the second volume 162) can function as a primary portion of the material. The first container portion 100A can be stored, transported, and otherwise processed for desired use of the material 50 therein. The second volume 162 (and the container portion 100B) can function as a secondary portion of the material. The second volume 162 can be dispensed by opening the tip 165. In response to the tip 165 being opened (see also e.g., tip 265 in FIGS. 2A-2B) the material 50 can be released or dispensed in a controlled manner during dispensing of the material 50, such as for example, in quality control operations. The tip 165 can be opened by tearing, pealing, cutting, or any other suitable manner to form an opening that allows for controlled dispensing of the material 50.

In some embodiments, the tapered portion also defines a larger diagonal bottom opening that is defined by a longer edge (e.g., along edges 111, 121) compared to the width of the volume 161, which would define the opening (e.g., if the opening was the same width as the sealable region 160) in the absence of a tapered volume 162. This configuration allows for a large opening for loading while retaining small footprint for both controlled freezing and space saving of the storage container 100 (including the second container portion 100B).

In some embodiments, the container can include measurement indicia 174. The measurement indicia 174 can include graduated markings located on the storage container 100. In some embodiments, the measurement indicia 174 are located on the tapered volume (e.g., volume 162. Measurement indicia allows for controlled filling into and/or dispensing of material 50 from the volume, thereby improving the quality control of testing and usage of the material in the volume.

In some embodiments, the first container portion 100A includes a first indicium (not shown) associated with the material 50. The first indicium can include a label or other marker associated with the material 50. In some embodiments, the label can be a machine-readable (and/or machine writable) label, such as a bar code, RFID, QR code, or the like. In this manner, information such as the type of material (e.g., a specific type of cell), the material lot, the packaging date, the source of the material (e.g., a cell line), the target use (including the destination) can be incorporated into the first container portion 100A to facilitate identification and tracking of the material therein. In some embodiments, the second container portion 100B includes a second indicium (not shown) associated with the material 50 or the first indicium. The second indicium can include a label or other marker associated with the material 50 or the first indicium (on the first container portion 100A). In some embodiments, the label can be a machine-readable (and/or machine writable) label, such as a bar code, RFID, QR code, or the like. In this manner, after the second container portion 100B is separated from the first container portion 100A, the two separate containers can be linked together to facilitate identification and tracking of the material therein. For example, QC test results performed on the materials from the second container portion 100B can be saved on the second indicium and loaded into a cloud storage system. These results can be associated with the materials in the first container portion 100A to ensure fast and accurate transmission of QC test results to the first container portion 100A.

Figure 13:
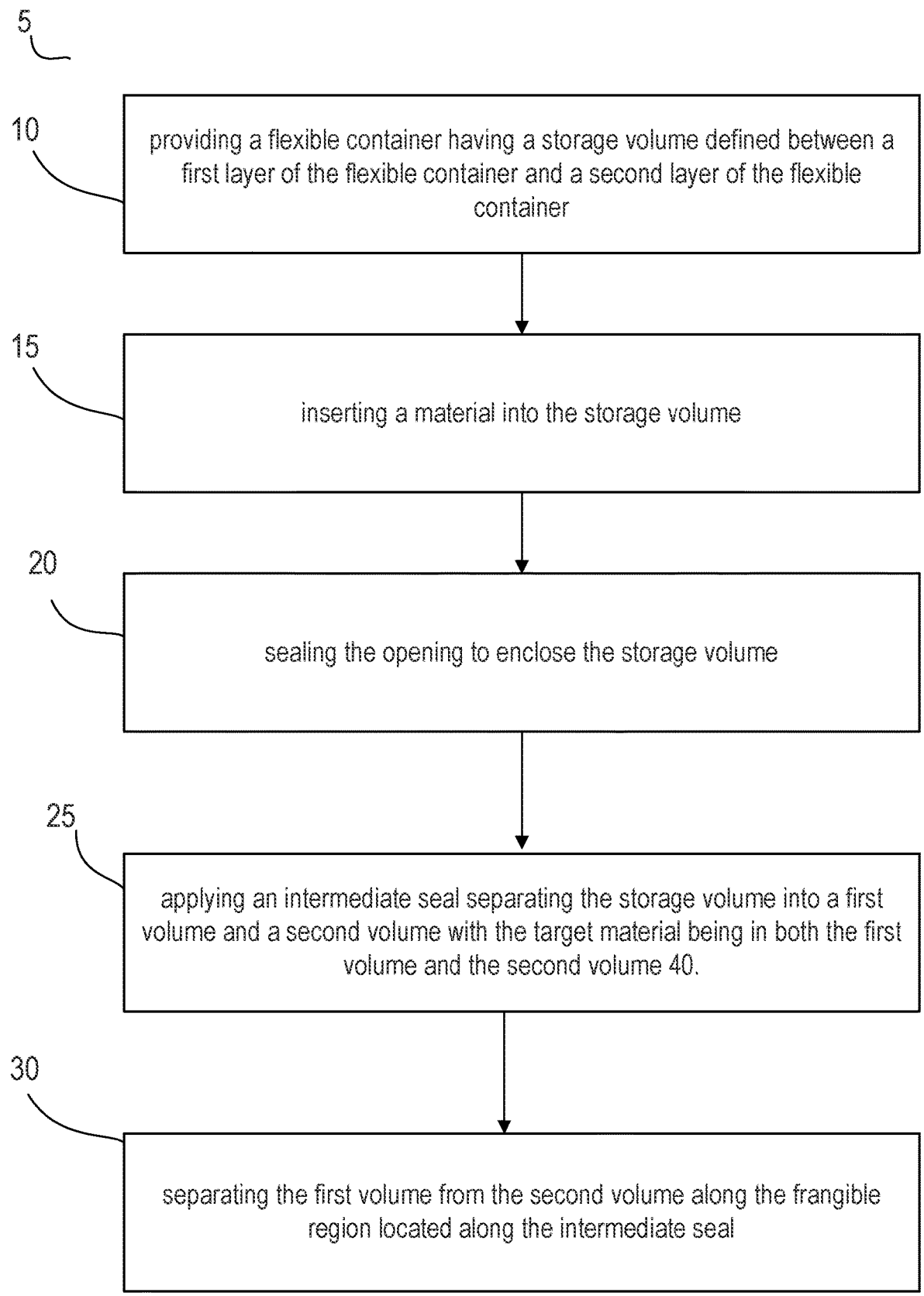
FIG. 13 is a flow chart illustrating a method of using a storage container system.

FIG. 13 is a flow chart showing a method 5 of storing a material 50 according to one embodiment. Although the method is described with reference to the container 100, in other embodiments, the method 5 can be performed on any of the containers described herein (e.g., container 200, 300, 400, 500, 600, 700, 800, 900, 1000, 1100, or 1200.) The method 5 includes providing (at 10) a storage container 100 (also referred to as a flexible container) having a storage volume 101 defined between a first layer 110 of the flexible container and a second layer 120 of the storage container 100. The storage container includes a first opening (e.g., port 140). The method 5 includes inserting (at 15) the material 50 into the storage volume 101 via the first opening (e.g., port 140). In some embodiments the container can optionally include, and material can be inserted via a second opening (e.g., edge opening 150). The method 5 includes sealing (at 20) the opening (e.g., closing the port 140) to enclose the storage volume 101. The method 5 includes applying (at 25) an intermediate seal 163 separating the storage volume 101 into a first volume 161 and a second volume 162 with the material being in both the first volume 161 and the second volume 162. In some embodiments, the storage container includes a frangible region 164 along the intermediate seal allowing the first volume and the second volume to be physically separated by hand along the frangible region 164. The method 5 includes separating (at 30) the first volume 161 from the second volume 162 along the frangible region 164 located along the intermediate seal 163. Additionally, or alternatively, the method can include separating and storing the second volume for future reference to the material stored therein. This allows ongoing testing and verification of the material to qualify, confirm, and/or verify the material included in the first volume. Additionally, or alternatively, the method can include dispending the material from either the first volume or the second volume. Since both volumes contain materials that match the other volume, one can serve as a reference material after the other volume is used.

Figure 2A:
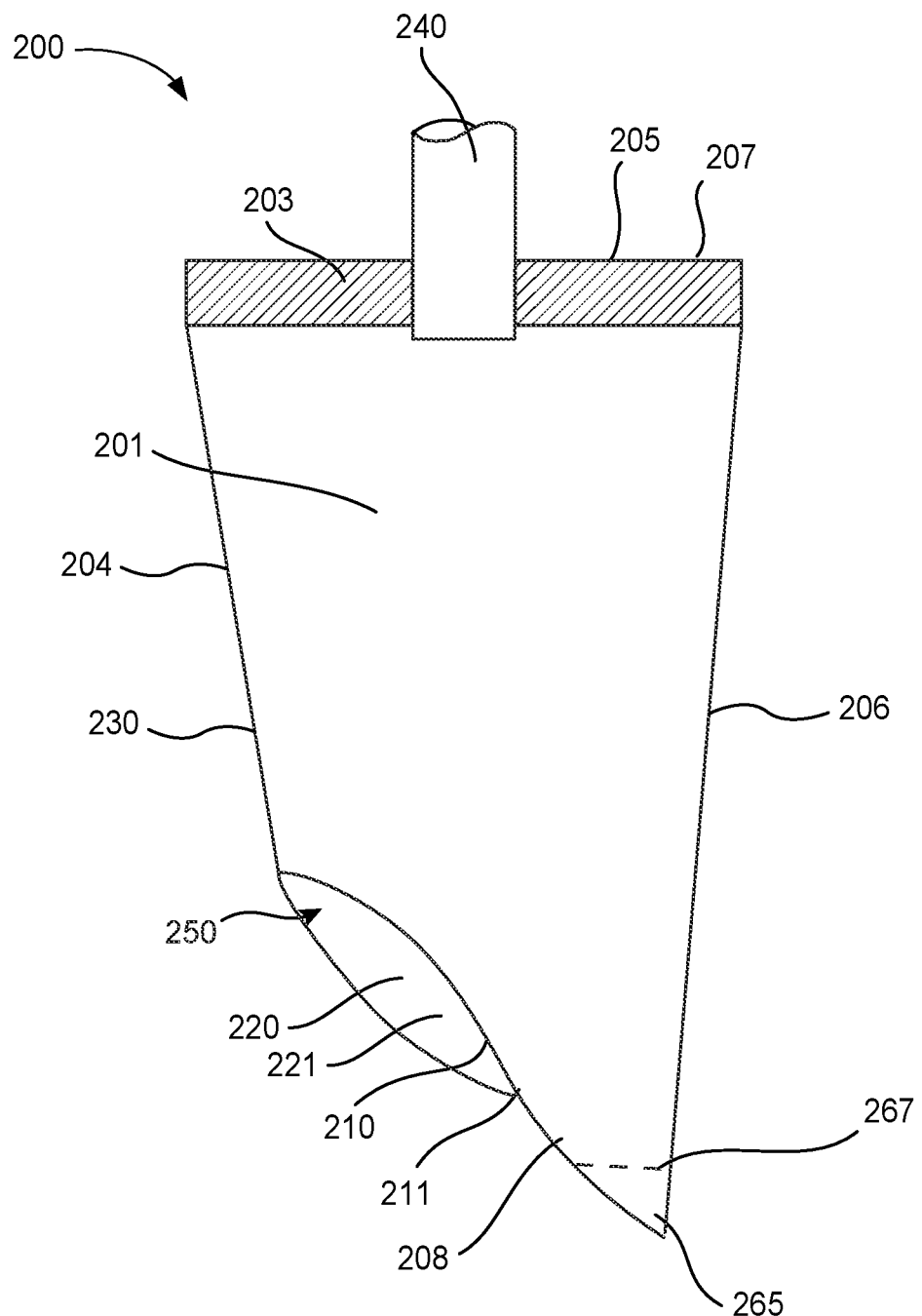
FIG. 2A is a schematic illustration of a storage container according to another embodiment in a first configuration.
Figure 2B:
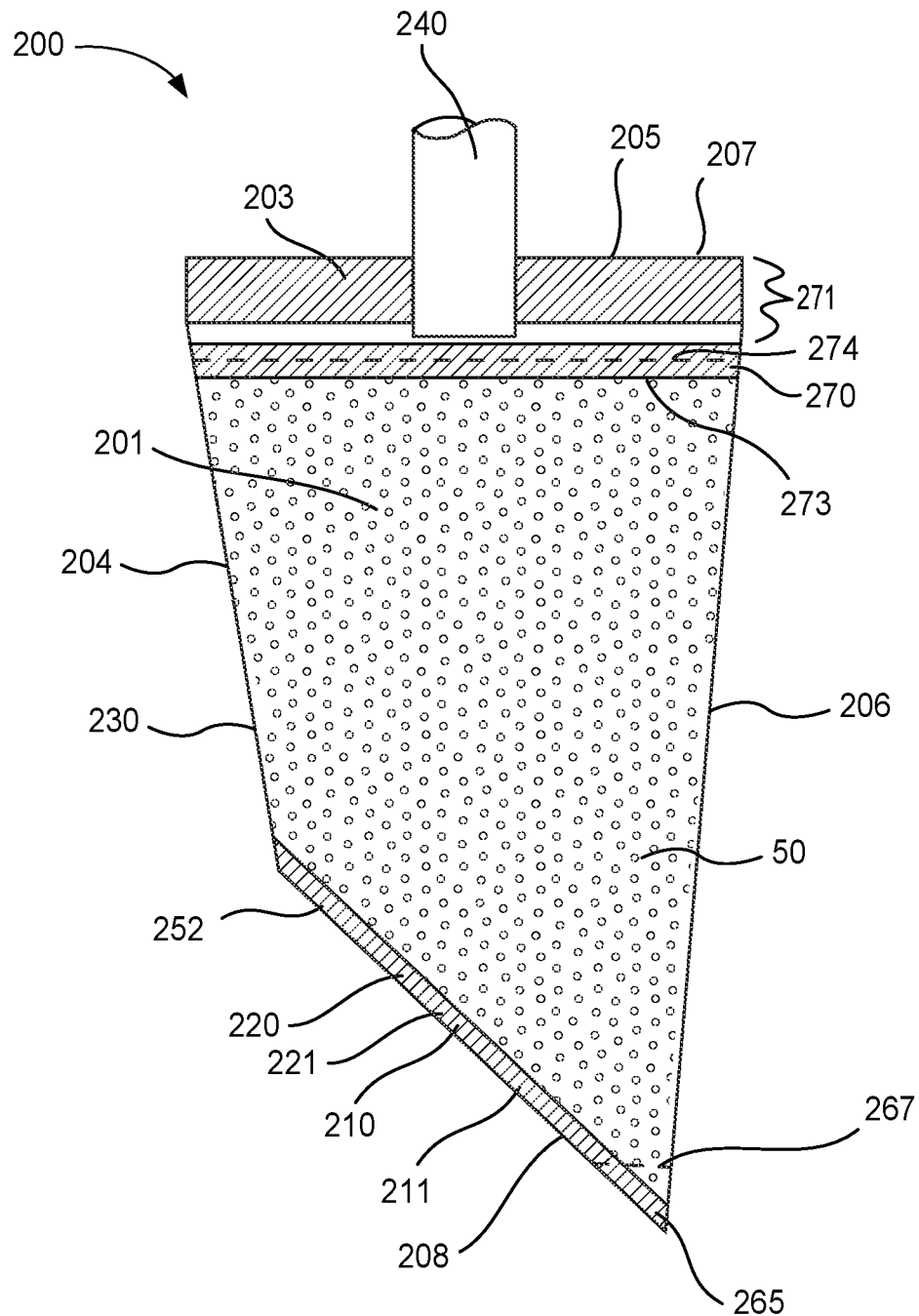
FIG. 2B is a schematic illustration of the storage container of FIG. 2A in a second configuration.

An embodiment of a storage container 200 is shown in FIGS. 2A-2B. The storage container 200 (and any of the container assemblies described herein) includes a storage volume 201 that can be used to store any of the tissue and biological materials described herein, and/or to perform any of the methods described herein and/or the methods of preparing the material for use in a procedure. As described herein, the storage container 200 provides a container that can be used for cryogenically freezing, storage, transport, processing, defrosting and/or rehydration of the material. The storage container 200 also includes a first layer 210, a second layer 220 and one or more seals 230 connecting the first layer 210 and the second layer 220. The one or more seals 230 form side edges 204, 206 of the storage container 200. While sealed edges can define the container 200, it is also appreciated that in some embodiments, the two layers (e.g., 210, 220) can be provided as tubular material that is flattened forming two longitudinal connections between the layers on the flattened longitudinal edges of the tubular material (e.g., layflat tubular film). Said another way, the side edges 204, 206 need not be formed by the one or more seals 230.

As shown in FIG. 2A, the storage container 200 includes one or more material ingresses and/or egresses. For example, the storage container 200 can include a first opening (e.g., port 240). The storage container 200 can also or alternatively include a second opening (e.g., edge opening 250). In some embodiments, the first opening is defined by a port 240. For example, as shown in FIG. 2A, the two layers 210, 220 respectively are joined at a first end portion 203 with the port 240 therebetween, and the two side edges 205, 207 at the first end portion are joined together. The port 240 is coupled to the first end portion 203 of the storage container 200 and is configured to allow fluid communication between the outside of the storage container 200 and the storage volume 201. In this manner, material can be inserted or additionally or alternatively treated (e.g., with a preservation fluid) after being conveyed into the storage container 200 via the port 140. Additionally or alternatively, the port 240 can also be coupled to a vacuum source to evacuate the storage volume. Additionally or alternatively, when in use (e.g., during a surgical procedure), the port 240 can allow for cryogenically defrosting the material. Additionally or alternatively, when in use (e.g., during a surgical procedure), the port 240 can allow for inflow of fluid for rehydration or other purposes. Additionally or alternatively, when in use, the port 240 can allow for removal of fluid.

The port 240 can be any suitable port that selectively provides fluid communication to the storage volume 201. For example, the port 240 can include a tube, a valve, and/or a cap. In some embodiments, the port 240 can be a needle-free port. In some embodiments, the port 240 can be a swabable connector. Similarly stated in some embodiments, the port 240 can have external surfaces and can be devoid of recesses or crevices such that the port 240 can be easily wiped or "swabbed" to maintain sterility during use. In some embodiments, the port 240 can include any of the barbed, swabable valves produced by the Halkey-Roberts Corporation, such as the 2455 series of swabable valves. In other embodiments, the port 240 (and any of the ports described herein) need not be either a swabable connector or a needle-free port; any suitable port can be employed. In some embodiments, the port 240 can include a male or female luer fitting. In some embodiments, the port 240 can include a threaded connection for coupling with a syringe or a tubing set. In some embodiments, the port 240 can be sealed at the end for sterile docking or cutting.

Although the port 240 is shown as being coupled at the first end portion 203 of the storage container 200. In other embodiments, the port 240 (and any of the ports described herein) can be coupled at any location and to any portion of the storage container 200. For example, in some embodiments, the port 240 (and any of the ports described herein) need not be coupled to the first end portion 203 of the container 200, the port can be on the surface or another edge portion of the container 200. The port 240 (and any of the ports described herein) can be offset from a center line of the storage container 200. For example, in some embodiments, the port can be located at a corner of the container. In some embodiments, the port (and any of the ports described herein) can be coupled around a central portion of the container.

In some embodiments, the port 240 can include a filter. In some embodiments, the port 240 can include a Y-connector. The base of the Y-connector near port can contain the filter. One end of the Y-connector can be sealed. The other end of the Y-connector can be threaded port for syringe connection. This allows for both hospital uses (e.g., syringe connection to port) and lab uses (e.g., a sterile dockable connection to the port). In some embodiments, the material stored in the storage volume 201 does not or is limited in its ability to move through the port 240. This may be due to size, viscosity, or other characteristics. In such embodiment, the port can be filterless allowing processing material to move into or out of the volume without regard to the material stored therein. In some embodiments, the port 240 allows material to be inserted into and removed from the storage volume 201 of each of the storage container 200.

In some embodiments, the container 200 includes a seal 252 along the tapered second end portion that extends across the edge 208 of container 200 to connect the separation between edges 211 and 221. In some embodiments, seal 252 is a permanent seal. In some embodiments, seal 252 is a peelable seal. For example, the connection between the first layer 210 and the second layer 220 can be a peelable connection such that the opening 250 includes areas in which the first layer 210 and the second layer 220 can be peeled apart after connection. The container 200 can include features of the various the containers as disclosed in U.S. Pat. No. 11,065,095 (the '095 patent), titled "Sample Container with Peelable Seal and Access Port," which is hereby incorporated by reference in its entirety. In light of the disclosure in the present application a person of ordinary skill in the art could adapt the features of the container in the '095 patent to be formed on as a storage container having peel reseal openings similar to those disclosed in the '095 patent.

In various examples, the connection between the first layer 210 and the second layer 220 can be a peelable connection such that the region includes areas in which the first layer and the second layer can be peeled apart after connection. For example, in some embodiments, the peelable seal 252 can be an adhesive-based seal in which an adhesive layer pulls back from one of the first layer 210 or the second layer 220 when the first layer 210 is peeled apart from the second layer 220. In other embodiments, the peelable seal can be a cohesive seal in which an adhesive layer or intermediate layer fails within itself when the first layer 210 is peeled apart from the second layer 220. The peelable seal 252 can be produced by any suitable methods and/or mechanism as described herein, such as, for example, by a heat-sealing operation. The seal and/or the layers 210, 220, whether peelable or permanent hermetically seals the storage volume 201. The peelable seal 252 can be of any suitable geometry to facilitate the desired peel direction, peel strength, and the like. For example, in some embodiments, the peelable seal 252 can be an angled seal that provides for peel tabs that can be grasped by the user to peel the first layer 210 from the second layer 220. In some embodiments, as illustrated in FIG. 2B, the seal 252 can extend across the length of the tapered edge 211, 221. However, in other embodiments, the seal 252 can extend across a portion of an edge. Because cutting and tearing can introduce foreign matter, the peelable opening allows for the contents inside to remain aseptic after opening the container 200. Additionally, the peel strength can be adjusted based on the material selected. In some examples, the peel strength is between 0.25 pounds and 5 pounds. In other examples, the peel strength is between 0.5 pounds and 2 pounds. In one example, the peel strength is about 1 pound.

In some embodiments, the container 200 includes a seal 273 (which functions as an end portion seal). As illustrated in FIG. 2A, the container 200 can be empty and ready for use in the storage system. The material 50 (shown in FIG. 2B) can be inserted through port 240 or opening 250. After the material has been inserted into the volume 201 of container 200, the seal 273 can be applied as shown in FIG. 2B. For example, the storage container 200 can include a sealable region suitable to apply (or produce) the end portion seal 273 to fluidically isolate the storage volume 201 from the port 240. Specifically, the end portion seal 273 is applied after the material 50 has been introduced into the storage volume 201. The end portion seal 273 is applied or produced by any suitable procedure or mechanism, such as via a heat seal, a pressure seal, a laser weld, an adhesive seal, or any other suitable sealing procedures. In some embodiments, the sealable region can include indicia or other markings to indicate to the user loading the material 50 into the storage container 200 where to apply the end portion seal 273.

When sealed at the indicia, the seal 273 also allows for removal of the port 240. Specifically, in some embodiments, the container 200 includes a frangible region 270. The frangible region 270 can be suitable to facilitate or initiate separation of the port section 271 including the port 240 from storage volume 201. The frangible region 270 can include perforations, thinning of material, stress risers suitable to directional tearing, adhesive attached otherwise detached containers or any other suitable mechanism for separating the port section 271 and storage volume 201 of the storage container 200 from one another. In some embodiments, the frangible region 270 can include one or more perforations lines 274 positioned between storage volume 201 and port section 271. When the frangible regions are separated, port section 271 is removable from the storage volume 201 without compromising the sealed structure of storage volume 201. However, it will be appreciated that other shapes of the volumes, seals, and frangible regions are applicable as well. In some embodiments, the port section can be different shapes suitable to allow removal of the port 240 from container 200. In some embodiments, the width of the end portion seal 273 is greater than the width of the frangible region 270. In some embodiments, the width of the end portion seal 273 is at least two times than the width of the frangible region 270. In some embodiments, the frangible region can include a seal (e.g., 273) and a frangible portion (e.g., perforations). Additionally or alternatively, the frangible portion may separate the storage volume 201 into separate volumes similar to the embodiments discussed with regards to FIG. 1C-1E above.

In some embodiments, the storage volume 201 can be tapered from a first end portion 203 to a narrower width on the opposite side at tip 265. In some embodiments the narrower width tip 265 can be a point as shown in FIGS. 2A and 2B. The tapered portion with its narrow end can be opened thereby allowing material within the storage volume 201 to be dispensed in a controlled manner. Without a port on the storage volume 201, port leaking can be avoided producing robust long-term storage. After removal of port 240, the storage volume 201 can be dispensed by separating tip 265 along a frangible region 267. When the tip 265 is removed the material can be released or dispensed in a controlled manner. The opening can control the amount of material dispensed. For example, the size of the opening adjusts the amount of material to be dispensed. The size can also be adjusted to the type of material being dispense. For example, a more viscous material can benefit from a larger opening. A less viscous material can benefit from a smaller opening.

In some embodiments, the tapered portion also defines a larger diagonal bottom opening that is defined by a longer edge (e.g., along edges 211, 221) compared to the width of the storage volume 201 at its widest region (e.g., above the tapered region). This configuration allows for a large opening for loading while retaining small footprint for both controlled freezing and space saving of the container 200.

Figure 3A:
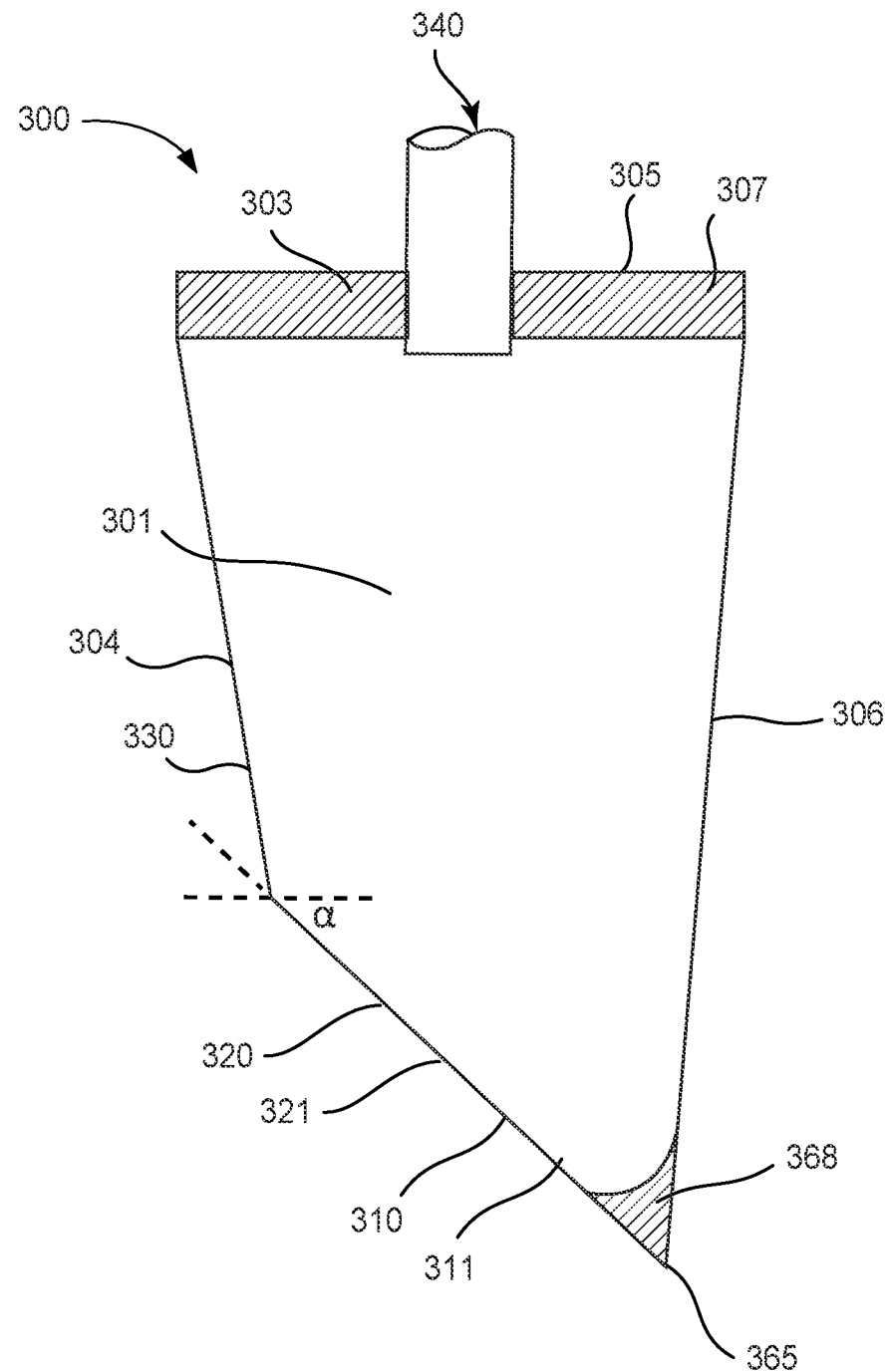
FIG. 3A is a schematic illustration of a storage container according to another embodiment in a first configuration.

An embodiment of a storage container 300 is shown in FIG. 3A. The storage container 300 (and any of the container assemblies described herein) includes a storage volume 301 that can be used to store any of the tissue and biological materials described herein, and/or to perform any of the methods described herein and/or the methods of preparing the material for use in a procedure. As described herein, the storage container 300 provides a container that can be used for cryogenically freezing, storage, transport, processing, defrosting and/or rehydration of the material. The storage container 300 also includes a first layer 310, a second layer 320 and one or more seals 330 connecting the first layer 310 and the second layer 320. The one or more seals 330 form side edges 304, 306 of the storage container 300. While sealed edges can define the container 300, it is also appreciated that in some embodiments, the two layers (e.g., 310, 320) can be provided as tubular material that is flattened forming two longitudinal connections between the layers on the flattened longitudinal edges of the tubular material (e.g., layflat tubular film). Said another way, the side edges 304, 306 need not be formed by the one or more seals 330.

Figure 3B:
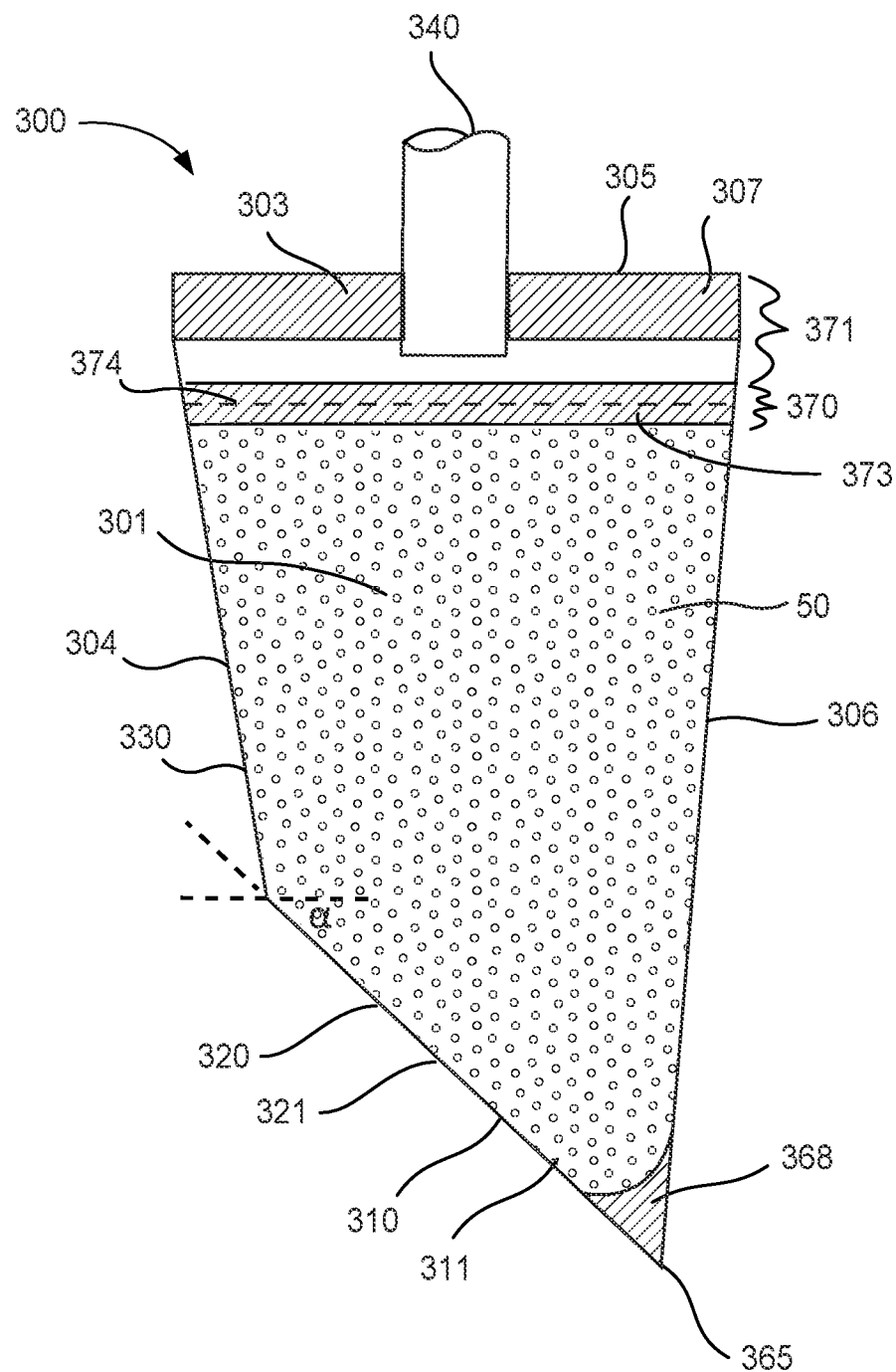
FIG. 3B is a schematic illustration of the storage container of FIG. 3A in a second configuration.

As shown in FIG. 3B, the storage container 300 includes one or more material ingresses and/or egresses. For example, the storage container 300 can include a first opening (e.g., defined by the port 340). The storage container 300 can also or alternatively include a second opening (e.g., peelable region 368). The first opening can include any opening suitable to receive or expel the material (or other fluids or flowable substances associated with the material, such as a wash solution, buffer, or rehydration solution). In some embodiments, the first opening is defined by a port 340. For example, as shown in FIG. 3A, the two layers 310, 320 respectively are joined at a first end portion 303 with the port 340 therebetween, and the two side edges 305, 307 are joined together. The port 340 is coupled to the first end portion 303 of the storage container 300 and is configured to allow fluid communication between the outside of the storage container 300 and the storage volume 301. In this manner, material can be inserted or additionally or alternatively treated (e.g., with a preservation fluid) after being conveyed into the storage container 300. Additionally or alternatively, the port 340 can also be coupled to a vacuum source to evacuate the storage volume. Additionally or alternatively, when in use (e.g., during a surgical procedure), the port 340 can allow for cryogenically defrosting the material. Additionally or alternatively, when in use (e.g., during a surgical procedure), the port 340 can allow for inflow of fluid used in rehydration or other purposes. Additionally or alternatively, when in use, the port 340 can allow for removal of fluid.

The port 340 can be any suitable port that selectively provides fluid communication to the storage volume 301. For example, the port 340 can include a tube, a valve, and/or a cap. In some embodiments, the port 340 can be a needle-free port. In some embodiments, the port 340 can be a swabable connector. Similarly stated in some embodiments, the port 340 can have external surfaces and can be devoid of recesses or crevices such that the port 340 can be easily wiped or "swabbed" to maintain sterility during use. In some embodiments, the port 340 can include any of the barbed, swabable valves produced by the Halkey-Roberts Corporation, such as the 3455 series of swabable valves. In other embodiments, the port 340 (and any of the ports described herein) need not be either a swabable connector or a needle-free port; any suitable port can be employed. In some embodiments, the port 340 can include a male or female luer fitting. In some embodiments, the port 340 can include a threaded connection for coupling with a syringe or a tubing set. In some embodiments, the port 340 can be sealed at the end for sterile docking or cutting.

Although the port 340 is shown as being coupled at the first end portion 303 of the storage container 300. In other embodiments, the port 340 (and any of the ports described herein) can be coupled at any location and to any portion of the storage container 300. For example, in some embodiments, the port 340 (and any of the ports described herein)

need not be coupled to the first end portion 303 of the container 300, the port can be on the surface or another edge portion of the container 300. The port 340 (and any of the ports described herein) can be offset from a center line of the storage container 300. For example, in some embodiments, the port can be located at a corner of the container. In some embodiments, the port (and any of the ports described herein) can be coupled around a central portion of the container.

In some embodiments, the port 340 can include a filter. In some embodiments, the port 340 can include a Y-connector. The base of the Y-connector near port can contain the filter. One end of the Y-connector can be sealed. The other end of the Y-connector can be threaded port for syringe connection. This allows for both hospital uses (e.g., syringe connection to port) and lab uses (e.g., a sterile dockable connection to the port). In some embodiments, the material stored in the storage volume 301 does not or is limited in its ability to move through the port 340. This may be due to size, viscosity, or other characteristics. In such embodiment, the port can be filterless allowing processing material to move into or out of the volume without regard to the material stored therein.

In some embodiments, the container 300 includes a seal 373 (which functions as an end portion seal). As illustrated in FIG. 3A, the container 300 can be empty and ready for use in the storage system. The material 50 (shown in FIG. 3B) can be inserted through port 340. After the material has been inserted into the volume 301 of container 300, the seal 373 can be applied as shown in FIG. 3B. For example, the storage container 300 can include a sealable region suitable to apply (or produce) the end portion seal 373 to fluidically isolate the storage volume 301 from the port 340. Specifically, the end portion seal 373 is applied after the material 50 has been introduced into the storage volume 301. The end portion seal 373 is applied or produced by any suitable procedure or mechanism, such as via a heat seal, a pressure seal, a laser weld, an adhesive seal, or any other suitable sealing procedures. In some embodiments, the sealable region can include indicia or other markings to indicate to the user loading the material 50 into the storage container 300 where to apply the end portion seal 373.

The seal 373 also allows for removal of the port 340. In some embodiments, the container 300 includes a frangible region 370. The frangible region 370 can be suitable to facilitate or initiate separation of the port section 371 including the port 340 from the storage volume 301. The frangible region 370 can include perforations, thinning of material, stress risers suitable to directional tearing, adhesive attached otherwise detached containers or any other suitable mechanism for separating the port section 371 and the storage volume 301 of the storage container 300 from one another. In some embodiments, the frangible region 370 can include one or more perforations lines 374 positioned between the storage volume 301 and port section 371. When the frangible regions are separated port section 371 is removable from the storage volume 301 without compromising the sealed structure of the storage volume 301. However, it will be appreciated that other shapes of the volumes, seals, and frangible regions are applicable as well. In some embodiments, the port section can be different shapes suitable to allow removal of the port 340 from container 300. In some embodiments, the width of the end portion seal 373 is greater than the width of the frangible region 370. In some embodiments, the width of the end portion seal 373 is at least two times than the width of the frangible region 370.

In some embodiments, the frangible region can include a seal (e.g., 373) and a frangible portion (e.g., perforations). Additionally or alternatively, the frangible portion may separate the storage volume 301 into separate volumes similar to the embodiments discussed with regards to FIG. 1A-1E above.

In some embodiments, the storage volume 301 can be tapered from end portion 303 to a narrower width on the opposite side end 365. In some embodiments the narrower width end 365 can be a point or a tip as shown in FIG. 3A. The tapered portion with its narrow end can be opened thereby allowing the storage volume 301 to be dispensed in a controlled manner. Without a port attached to the storage volume 301, port leaking can be avoided producing robust long-term storage. After removal of port 340, the storage volume 301 can be dispensed by separating tip 365 along opening 367. When the tip 365 is opened, the material can be released or dispensed in a controlled manner. In some embodiments, the opening is a peelable seal 368. The connection between the first layer 310 and the second layer 320 can be a peelable connection such that the opening includes areas in which the first layer 310 and the second layer 320 can be peeled apart after connection. The container 300 can include features of the various the containers as disclosed in U.S. Pat. No. 11,065,095 (the '095 patent, titled "Sample Container with Peelable Seal and Access Port," which is hereby incorporated by reference in its entirety. In light of the disclosure in the present application a person of ordinary skill in the art could adapt the features of the container in the '095 patent to be formed on as a storage container having peel reseal openings similar to those disclosed in the '095 patent.

In various examples, the connection between the first layer 310 and the second layer 320 can be a peelable connection such that the region includes areas in which the first layer and the second layer can be peeled apart after connection. For example, in some embodiments, the peelable region 368 can be an adhesive-based seal in which an adhesive layer pulls back from one of the first layer 310 or the second layer 320 when the first layer 310 is peeled apart from the second layer 320. In other embodiments, the peelable seal can be a cohesive seal in which an adhesive layer or intermediate layer fails within itself when the first layer 310 is peeled apart from the second layer 320. The peelable region 368 can be produced by any suitable methods and/or mechanism as described herein. The seal and/or the layers 310, 320, whether peelable or permanent hermetically seals the storage volume 301. The peelable region 368 can be of any suitable geometry to facilitate the desired peel direction, peel strength, and the like. For example, in some embodiments, the peelable region 368 can be an angled seal that provides for peel tabs that can be grasped by the user to peel the first layer 310 from the second layer 320. In some embodiments, as illustrated in FIG. 3B, the peelable region 368 can extend across the length of the tapered edge 311, 321. However, in other embodiments, the peelable region 368 can extend across a portion of an edge. Because cutting and tearing can introduce foreign matter, the peelable opening allows for the contents inside to remain aseptic after opening the container 300. Additionally, the peel strength can be adjusted based on the material selected. In some examples, the peel strength is between 0.25 pounds and 5 pounds. In other examples, the peel strength is between 0.5 pounds and 2 pounds. In one example, the peel strength is about 1 pound. The peel can also control the amount of material dispensed. For example, how far the layers are peeled adjusts the opening size allowing more material to be dispensed relative to a smaller opening. The size can also be adjusted to the type of material being dispense. For example, a more viscous material can benefit from a larger opening. A less viscous material can benefit from a smaller opening. In some embodiments, the tapered edge 311, 321 (or any other tapered edges described herein) extends at an angle (a) of between about degrees to about 75 degrees.

Figure 4:
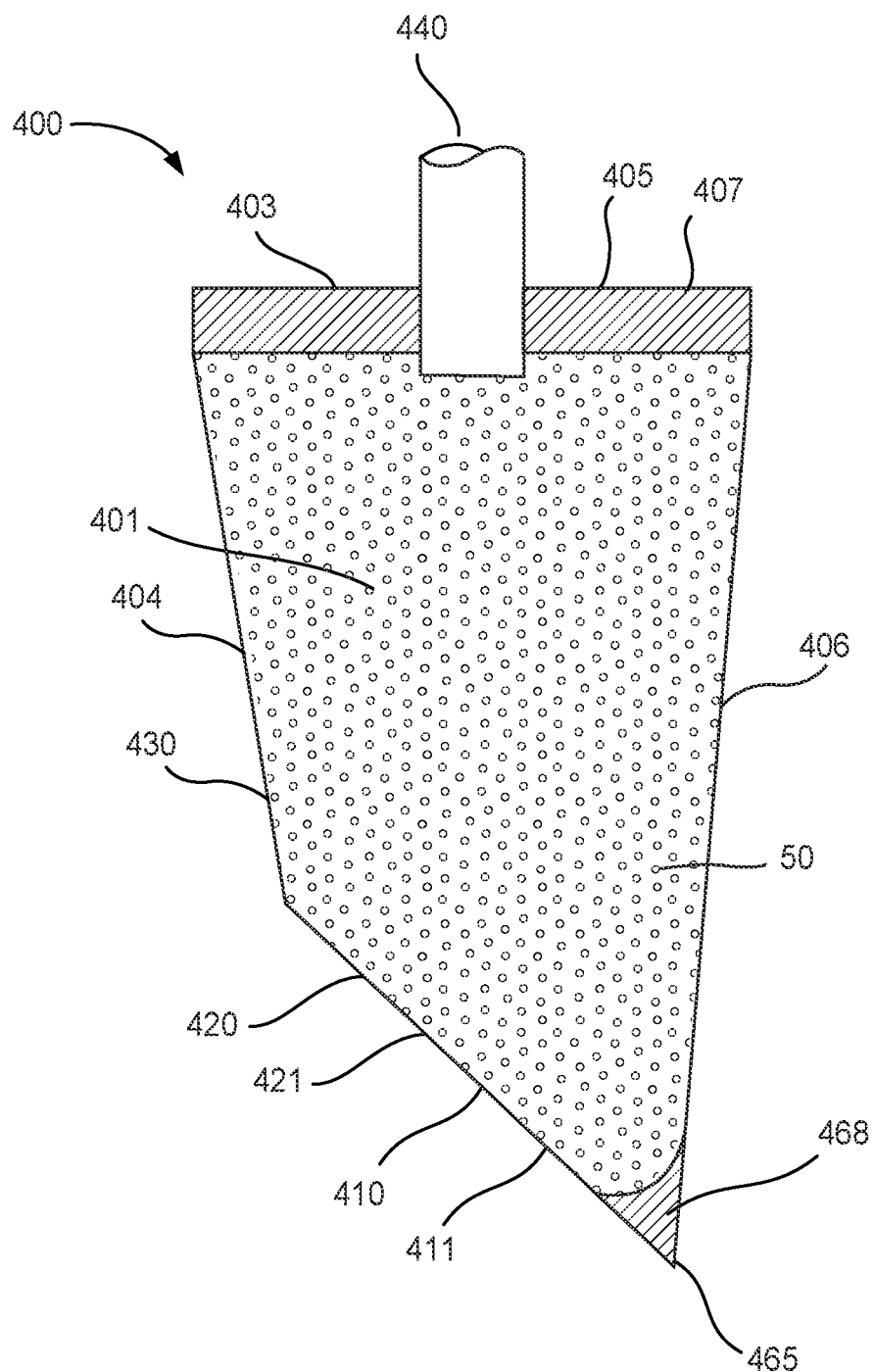
FIG. 4 is a schematic illustration of a storage container according to another embodiment.

An embodiment of a storage container 400 is shown in FIG. 4. The storage container 400 (and any of the container assemblies described herein) includes a storage volume 401 that can be used to store any of the tissue and biological materials described herein, and/or to perform any of the methods described herein and/or the methods of preparing the material for use in a procedure. As described herein, the storage container 400 provides a container that can be used for cryogenically freezing, storage, transport, processing, defrosting and/or rehydration of the material. The storage container 400 also includes a first layer 410, a second layer 420 and one or more seals 430 connecting the first layer 410 and the second layer 420. The one or more seals 430 form side edges 404, 406 of the storage container 400. While sealed edges can define the container 400, it is also appreciated that in some embodiments, the two layers (e.g., 410, 420) can be provided as tubular material that is flattened forming two longitudinal connections between the layers on the flattened longitudinal edges of the tubular material (e.g., layflat tubular film).

As shown in FIG. 4, the storage container 400 includes one or more material egresses. For example, the storage container 400 can include a first opening (e.g., port 440). The storage container 400 can also or alternatively include a second opening suitable for dispensing the material 50 located at tip 465. In some embodiments, the opening can include a peelable seal 468. FIG. 4 is an alternative to FIG. 3B in that the frangible region and upper seal proximal to the port are not applied.

In some embodiments, the first opening is a port 440. For example, as shown in FIG. 4, the two layers 410, 420 respectively are joined at a first end portion 403 with the port 440 therebetween, and the two side edges 405, 407 are joined together. The port 440 is coupled to the first end portion 403 of the storage container 400 and is configured to allow fluid communication between the outside of the storage container 400 and the storage volume 401. In this manner, material can be inserted or additionally or alternatively treated (e.g., with a preservation fluid) after being sealed within the storage container 400. Additionally or alternatively, the port 440 can also be coupled to a vacuum source to evacuate the storage volume. Additionally or alternatively, when in use (e.g., during a surgical procedure), the port 440 can allow for cryogenically defrosting the material. Additionally or alternatively, when in use (e.g., during a surgical procedure), the port 440 can allow for inflow of fluid used for rehydration or other uses. Additionally or alternatively, when in use, the port 440 can allow for removal of fluid.

The port 440 can be any suitable port that selectively provides fluid communication to the storage volume 401. For example, the port 440 can include a tube, a valve, and/or a cap. In some embodiments, the port 440 can be a needle-free port. In some embodiments, the port 440 can be a swabable connector. Similarly stated in some embodiments, the port 440 can have external surfaces and can be devoid of recesses or crevices such that the port 440 can be easily wiped or "swabbed" to maintain sterility during use. In some embodiments, the port 440 can include any of the barbed, swabable valves produced by the Halkey-Roberts Corporation, such as the 3455 series of swabable valves. In other embodiments, the port 440 (and any of the ports described herein) need not be either a swabable connector or a needle-free port; any suitable port can be employed. In some embodiments, the port 440 can include a male or female luer fitting. In some embodiments, the port 440 can include a threaded connection for coupling with a syringe or a tubing set. In some embodiments, the port 440 can be sealed at the end for sterile docking or cutting.

Although the port 440 is shown as being coupled at the first end portion 403 of the storage container 400. In other embodiments, the port 440 (and any of the ports described herein) can be coupled at any location and to any portion of the storage container 400. For example, in some embodiments, the port 440 (and any of the ports described herein) need not be coupled to the first end portion 403 of the container 400, the port can be on the surface or another edge portion of the container 400. The port 440 (and any of the ports described herein) can be offset from a center line of the storage container 400. For example, in some embodiments, the port can be located at a corner of the container. In some embodiments, the port (and any of the ports described herein) can be coupled around a central portion of the container.

In some embodiments, the port 440 can include a filter. In some embodiments, the port 440 can include a Y-connector. The base of the Y-connector near port can contain the filter. One end of the Y-connector can be sealed. The other end of the Y-connector can be threaded port for syringe connection. This allows for both hospital uses (e.g., syringe connection to port) and lab uses (e.g., a sterile dockable connection to the port). In some embodiments, the material stored in the storage volume 401 does not or is limited in its ability to move through the port 440. This may be due to size, viscosity, or other characteristics. In such embodiment, the port 440 can be filterless allowing processing material to move into or out of the storage volume 401 without regard to the material stored therein.

In some embodiments, volume 401 can be tapered from end portion 403 to a narrower width on the opposite end portion near tip 465. In some embodiments the narrower width portion of the container can be a point or tip 465 as shown in FIG. 4. The tapered portion with its narrow end can be opened thereby allowing the storage volume 401 to be dispensed in a controlled manner. Without a port attached to the storage volume 401, port leaking can be avoided producing robust long-term storage. After removal of port 440, the storage volume 401 can be dispensed by separating tip 465 along opening 467. When the tip 465 is opened, the material can be released or dispensed in a controlled manner.

In some embodiments, one opening is a peelable seal 468. The connection between the first layer 410 and the second layer 420 can be a peelable connection such that the opening includes areas in which the first layer 410 and the second layer 420 can be peeled apart after connection defining the peelable seal 468. The container 400 can include features of the various the containers as disclosed in U.S. Pat. No. 11,065,095 (the '095 patent, titled "Sample Container with Peelable Seal and Access Port," which is hereby incorporated by reference in its entirety. In light of the disclosure in the present application, a person of ordinary skill in the art could adapt the features of the container in the '095 patent to be formed on as a storage container having peel reseal openings similar to those disclosed in the '095 patent.

In various examples, the connection between the first layer 410 and the second layer 420 can be a peelable connection such that the region includes areas in which the first layer and the second layer can be peeled apart after connection. For example, in some embodiments, the peelable seal 468 can be an adhesive-based seal in which an adhesive layer pulls back from one of the first layer 410 or the second layer 420 when the first layer 410 is peeled apart from the second layer 420. In other embodiments, the peelable seal can be a cohesive seal in which an adhesive layer or intermediate layer fails within itself when the first layer 410 is peeled apart from the second layer 420. The peelable seal 468 can be produced by any suitable methods and/or mechanism as described herein. The seal and/or the layers 410, 420, whether peelable or permanent hermetically seals the storage volume 401. The peelable seal 468 can be of any suitable geometry to facilitate the desired peel direction, peel strength, and the like. For example, in some embodiments, the peelable seal 468 can be an angled seal that provides for peel tabs that can be grasped by the user to peel the first layer 410 from the second layer 420. In some embodiments, as illustrated in FIG. 4, the peelable seal 468 can extend across the length of the tapered edge 411, 421. However, in other embodiments, the peelable seal 468 can extend across a portion of an edge. Because cutting and tearing can introduce foreign matter, the peelable opening allows for the contents inside to remain aseptic after opening the container 400. Additionally, the peel strength can be adjusted based on the material selected. In some examples, the peel strength is between 0.25 pounds and 5 pounds. In other examples, the peel strength is between 0.5 pounds and 2 pounds. In one example, the peel strength is about 1 pound. The peel can also control the amount of material dispensed. For example, how far the layers are peeled adjusts the opening size allowing more material to be dispensed relative to a smaller opening. The size can also be adjusted to the type of material being dispense. For example, a more viscous material can benefit from a larger opening. A less viscous material can benefit from a smaller opening.

Figure 5A:
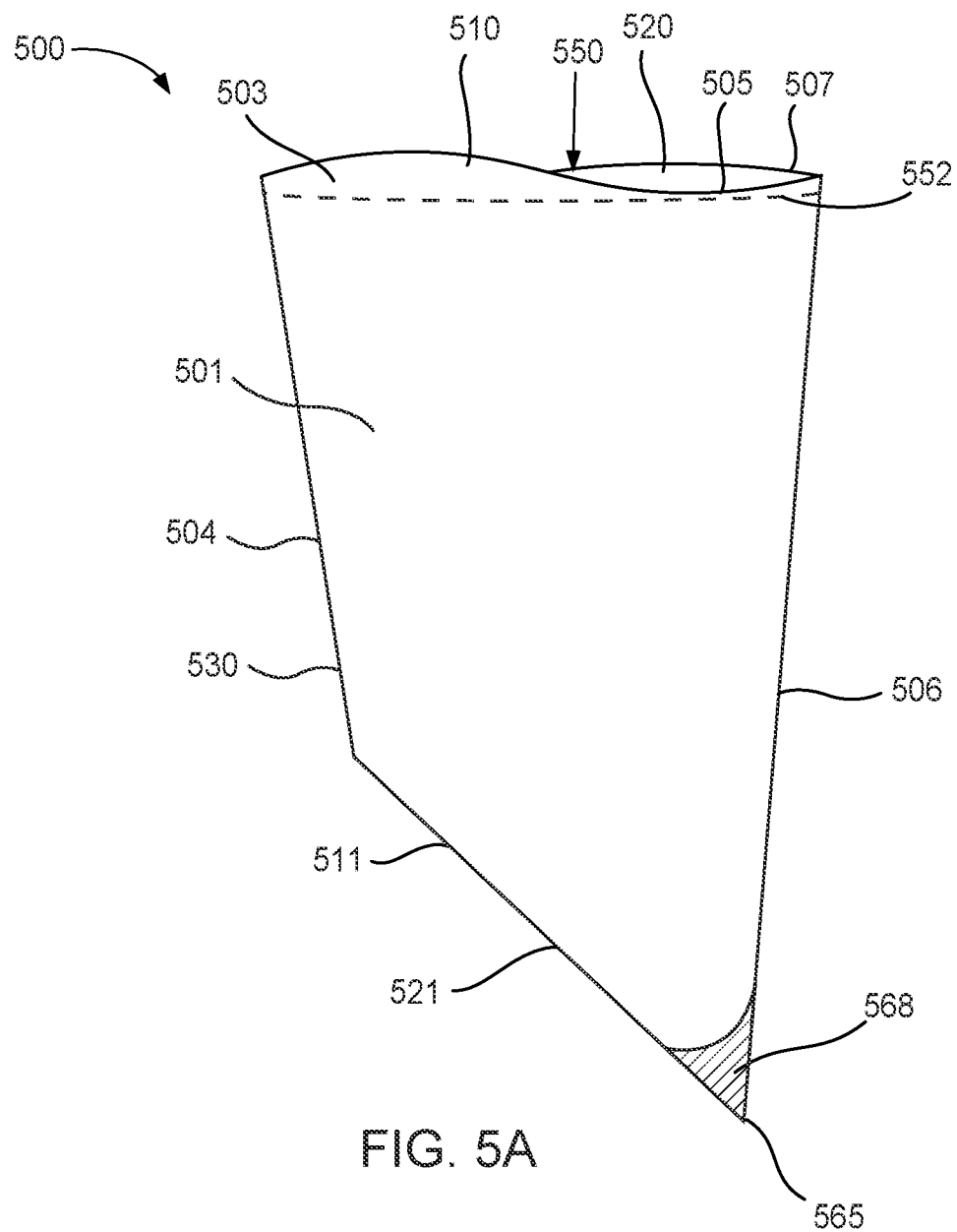
FIG. 5A is a schematic illustration of a storage container according to another embodiment in a first configuration.

An embodiment of a storage container 500 is shown in FIG. 5A. The storage container 500 (and any of the container assemblies described herein) includes a storage volume 501 that can be used to store any of the tissue and biological materials described herein, and/or to perform any of the methods described herein, and/or the methods of preparing the material for use in a procedure. As described herein, the storage container 500 provides a container that can be used for cryogenically freezing, storage, transport, processing, defrosting and/or rehydration of the material. The storage container 500 also includes a first layer 510, a second layer 520 and one or more seals 530 connecting the first layer 510 and the second layer 520. The one or more seals 530 form side edges 504, 506 of the storage container 500. While sealed edges can define the container 500, it is also appreciated that in some embodiments, the two layers (e.g., 510, 520) can be provided as tubular material that is flattened forming two longitudinal connections between the layers on the flattened longitudinal edges of the tubular material (e.g., layflat tubular film). Said another way, the side edges 504, 506 need not be formed by the one or more seals 530.

Figure 5B:
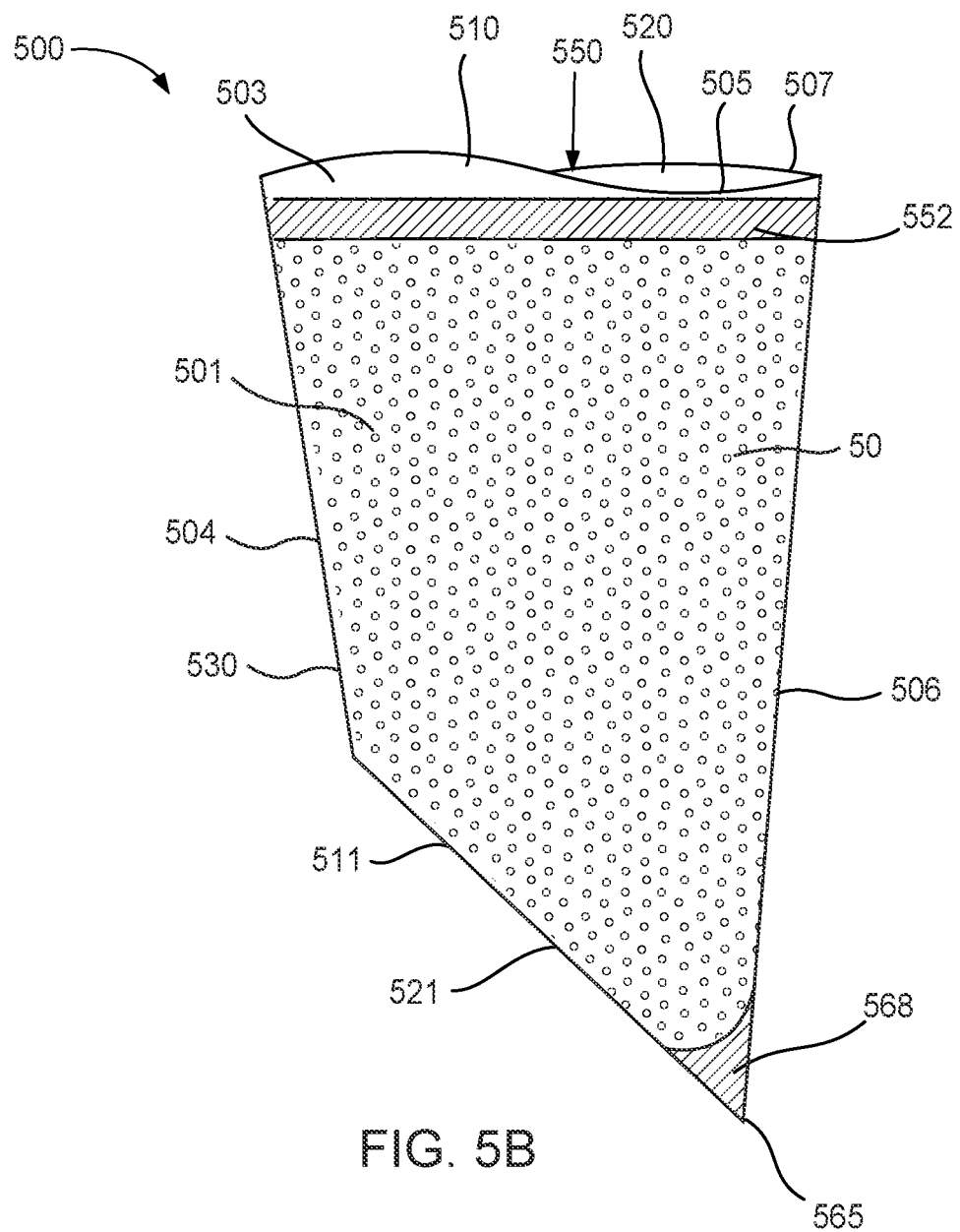
FIG. 5B is a schematic illustration of the storage container of FIG. 5A in a second configuration.

As shown in FIG. 5B, the storage container 500 includes one or more material ingresses and/or egresses. For example, the storage container 500 can include a first opening (e.g., opening 550). The storage container 500 can also or alternatively include a second opening (e.g., peelable region 568).

In some embodiments, in a first (or opened) configuration, one or more edges (e.g., edge 505) of the first layer 510 are spaced apart from one or more edges (e.g., edge 507) of the second layer 520 to define an opening 550 into the storage volume 501 of each of the storage container 500. The opening 550 can be of any suitable size to facilitate loading of the material (e.g., a tissue graft), as described herein. In some embodiments, the opening 550 can extend across a portion of the length of an end or a side of the storage container 500. In some embodiments, the opening 550 can extend across substantially all of the end or side of the storage container 500. In the example shown in FIG. 5A, the opening can extend across the end portion 503 of container 500 defined by the separation between edges 505 and 507. This opening can be larger than a ported opening, such as those ports discussed above. A larger opening can allow for input of a larger material (e.g., a tissue graft) into the storage volume 501. Although it is appreciated that other materials as discussed herein can additionally or alternatively be introduced through opening 550. In some embodiments, the container 500 includes a seal 552. As illustrated in FIG. 5A, the container 500 can be empty and ready for use in the storage system. The material 50 (shown in FIG. 5B) can be inserted through opening 550. After the material is introduced into volume 501, the opening 550 can be sealed by seal 552 enclosing volume 501 as shown in FIG. 5B. This allows for the loading of biologicals or other materials through the opening 550. Once loaded, the opening 550 is sealed with seal 552 hermetically containing the material. The seal can be performed by a heat seal, an adhesive, or other suitable methods. In some embodiments, a laser line guides seal closing the opening 550.

In some embodiments, seal 552 is a peelable seal. The connection between the first layer 510 and the second layer 520 can be a peelable connection such that the opening 550 includes areas in which the first layer 510 and the second layer 520 can be peeled apart after connection. The container 500 can include features of the various the containers as disclosed in U.S. Pat. No. 11,065,095 (the '095 patent, titled "Sample Container with Peelable Seal and Access Port," which is hereby incorporated by reference in its entirety. In light of the disclosure in the present application a person of ordinary skill in the art could adapt the features of the container in the '095 patent to be formed on as a storage container having peel reseal openings similar to those disclosed in the '095 patent.

In various examples, the connection between the first layer 510 and the second layer 520 can be a peelable connection such that the region includes areas in which the first layer and the second layer can be peeled apart after connection. For example, in some embodiments, the peelable seal 552 can be an adhesive-based seal in which an adhesive layer pulls back from one of the first layer 510 or the second layer 520 when the first layer 510 is peeled apart from the second layer 520. In other embodiments, the peelable seal can be a cohesive seal in which an adhesive layer or intermediate layer fails within itself when the first layer 510 is peeled apart from the second layer 520. The peelable seal 552 can be produced by any suitable methods and/or mechanism as described herein. The seal and/or the layers 510, 520, whether peelable or permanent hermetically seals the storage volume 501. The peelable seal 552 can be of any suitable geometry to facilitate the desired peel direction, peel strength, and the like. For example, in some embodiments, the peelable seal 552 can be an angled seal that provides for peel tabs that can be grasped by the user to peel the first layer 510 from the second layer 520. In some embodiments, as illustrated in FIG. 5B, the seal 552 can extend across the width of the end portion 503. However, in other embodiments, the seal 552 can extend across a portion of an end portion 503. Because cutting and tearing can introduce foreign matter, the peelable opening allows for the contents inside to remain aseptic after opening the container 500. Additionally, the peel strength can be adjusted based on the material selected. In some examples, the peel strength is between 0.25 pounds and 5 pounds. In other examples, the peel strength is between 0.5 pounds and 2 pounds. In one example, the peel strength is about 1 pound.

In some embodiments, volume 501 can be tapered. As shown in FIG. 5B the taper extends a portion of the way between end portion 503 and tip 565. In some embodiments, the taper can extend from end portion 503 to a narrower width on the opposite side. The tapered portion with its narrow end can be opened thereby allowing the storage volume 501 to be dispensed in a controlled manner. Without a port attached to storage volume 501, port leaking can be avoided producing robust long-term storage. After removal of port 540, the storage volume 501 can be dispensed by separating tip 565 along opening 567. When the tip 565 is opened, the material can be released or dispensed in a controlled manner. In some embodiments, the opening is a peelable seal 568. The connection between the first layer 510 and the second layer 420 can be a peelable connection such that the peelable seal 568 includes areas in which the first layer 510 and the second layer 520 can be peeled apart after connection. The container 500 can include features of the various the containers as disclosed in U.S. Pat. No. 11,065,095 (the '095 patent, titled "Sample Container with Peelable Seal and Access Port," which is hereby incorporated by reference in its entirety. In light of the disclosure in the present application, a person of ordinary skill in the art could adapt the features of the container in the '095 patent to be formed on as a storage container having peel reseal openings similar to those disclosed in the '095 patent.

In various examples, the connection between the first layer 510 and the second layer 520 can be a peelable connection such that the region includes areas in which the first layer and the second layer can be peeled apart after connection. For example, in some embodiments, the peelable seal 568 can be an adhesive-based seal in which an adhesive layer pulls back from one of the first layer 510 or the second layer 520 when the first layer 510 is peeled apart from the second layer 520. In other embodiments, the peelable seal can be a cohesive seal in which an adhesive layer or intermediate layer fails within itself when the first layer 510 is peeled apart from the second layer 520. The peelable seal 568 can be produced by any suitable methods and/or mechanism as described herein. The seal and/or the layers 510, 520, whether peelable or permanent hermetically seals the storage volume 501. The peelable seal 568 can be of any suitable geometry to facilitate the desired peel direction, peel strength, and the like. For example, in some embodiments, the peelable seal 568 can be an angled seal that provides for peel tabs 3560 that can be grasped by the user to peel the first layer 510 from the second layer 520. In some embodiments, as illustrated in FIG. 5B, the peelable seal 568 can extend across the length of the tapered edge 511, 521. However, in other embodiments, the peelable seal 568 can extend across a portion of an edge. Because cutting and tearing can introduce foreign matter, the peelable opening allows for the contents inside to remain aseptic after opening the container 500. Additionally, the peel strength can be adjusted based on the material selected. In some examples, the peel strength is between 0.25 pounds and 5 pounds. In other examples, the peel strength is between 0.5 pounds and 2 pounds. In one example, the peel strength is about 1 pound. The peel can also control the amount of material dispensed. For example, how far the layers are peeled adjusts the opening size allowing more material to be dispensed relative to a smaller opening. The size can also be adjusted to the type of material being dispense. For example, a more viscous material can benefit from a larger opening. A less viscous material can benefit from a smaller opening.

Figure 6A:
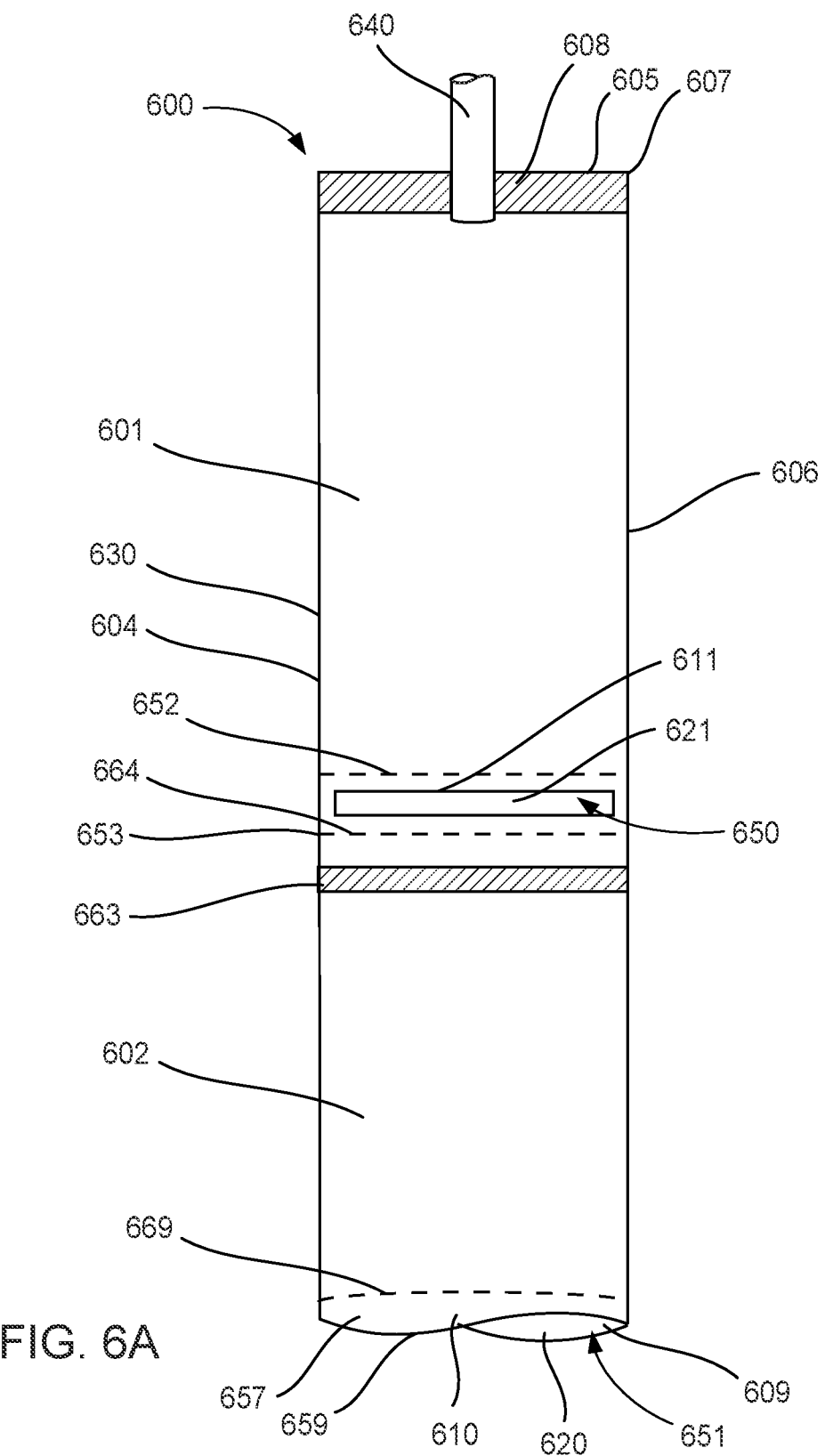
FIG. 6A is a schematic illustration of a storage container according to another embodiment in a first configuration.
Figure 6B:
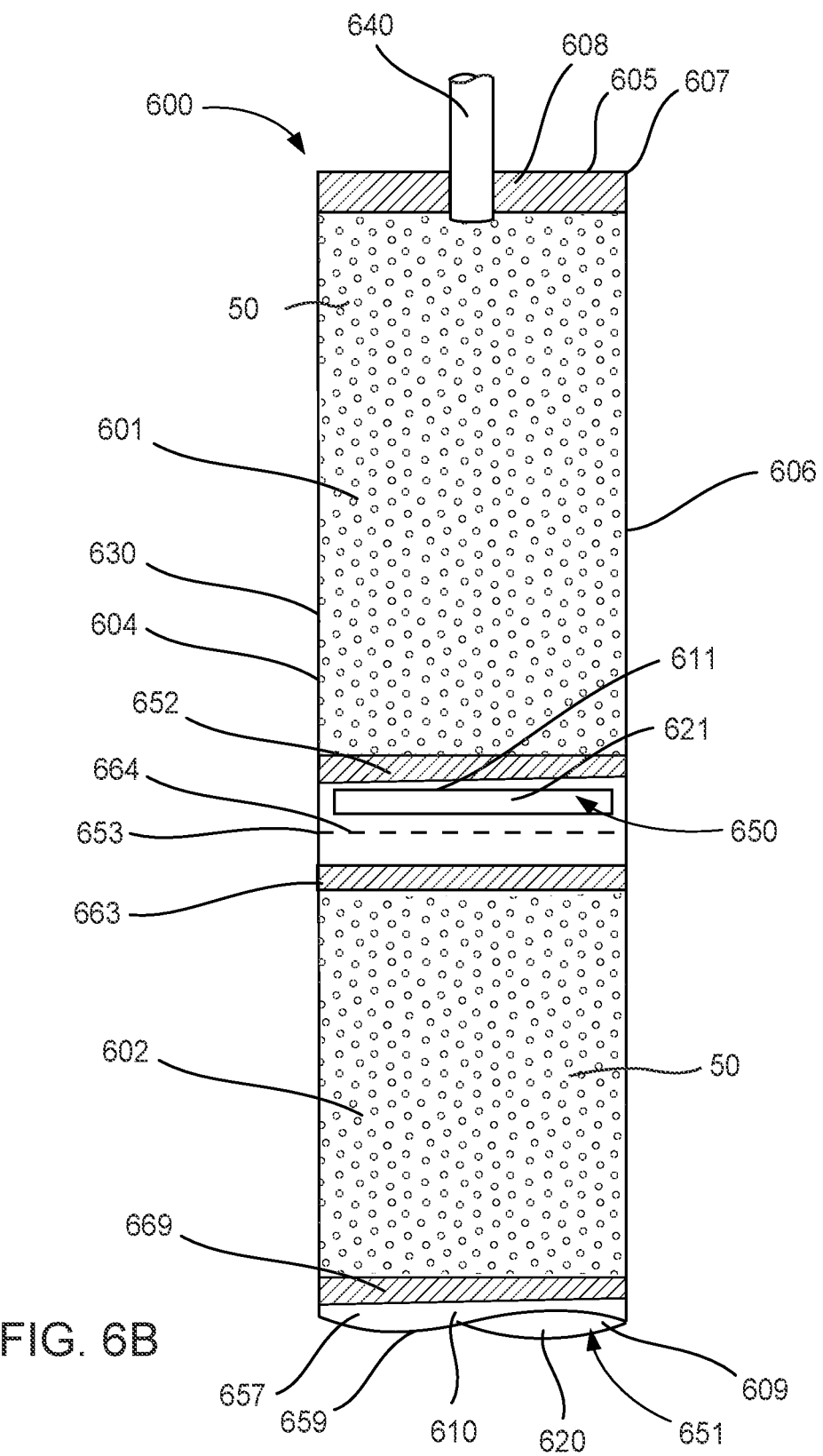
FIG. 6B is a schematic illustration of the storage container of FIG. 6A in a second configuration.

An embodiment of a storage container 600 is shown in FIG. 6A-B. The storage container 600 includes multiple storage volumes 601 and 602. The storage container 600 (and any of the container assemblies described herein) includes a first storage volume 601 that can be used to store any of the tissue and biological materials described herein, and/or to perform any of the methods described herein, and/or the methods of preparing the material for use in a procedure. In some embodiments, the storage container 600 can include a second storage volume 602 that can be used similarly to the first storage volume 601 to store any of the tissue and biological materials described herein, and/or to perform any of the methods described herein. Alternatively, the second storage volume 602 can be used to store peripheral items such as labels (e.g., to identify the material in the storage volume 601), tools (e.g., to perform procedures with the material in the storage volume 601), therapeutic treatments (e.g., to supplement or use with the material in the storage volume 601), etc.

As described herein, the storage container 600 can be used for cryogenically freezing, storage, transport, processing, defrosting and/or rehydration of the material. The storage container 600 also includes a first layer 610, a second layer 620 and one or more seals 630 connecting the first layer 610 and the second layer 620. The one or more seals 630 form side edges 604, 606 of the storage container 600. While sealed edges can define the container 600, it is also appreciated that in some embodiments, the two layers (e.g., 610, 620) can be provided as tubular material that is flattened forming two longitudinal connections between the layers on the flattened longitudinal edges of the tubular material (e.g., layflat tubular film).

As shown in FIG. 6A, the storage container 600 includes one or more material ingresses and/or egresses. For example, the storage container 600 can include a first opening (e.g., port 640). The storage container 600 can also or alternatively include a second opening (e.g., opening 650). In some embodiments, the first opening is a port 640. For example, as shown in FIG. 6A, the two layers 610, 620 respectively are joined at a first end portion 603 with the port 640 therebetween, and the two side edges 605, 607 are joined together. The port 640 is coupled to the first end portion 603 of the storage container 600 and is configured to allow fluid communication between the outside of the storage container 600 and the storage volume 601. In this manner, material can be inserted or additionally or alternatively treated (e.g., with a preservation fluid) after being sealed within the storage container 600. Additionally or alternatively, the port 640 can also be coupled to a vacuum source to evacuate the storage volume. Additionally or alternatively, when in use (e.g., during a surgical procedure), the port 640 can allow for cryogenically defrosting the material. Additionally or alternatively, when in use (e.g., during a surgical procedure), the port 640 can allow for inflow of fluid used in rehydration or other uses. Additionally or alternatively, when in use, the port 640 can allow for removal of fluid.

The port 640 can be any suitable port that selectively provides fluid communication to the storage volume 601. For example, the port 640 can include a tube, a valve, and/or a cap. In some embodiments, the port 640 can be a needle-free port. In some embodiments, the port 640 can be a swabable connector. Similarly stated in some embodiments, the port 640 can have external surfaces and can be devoid of recesses or crevices such that the port 640 can be easily wiped or "swabbed" to maintain sterility during use. In some embodiments, the port 640 can include any of the barbed, swabable valves produced by the Halkey-Roberts Corporation, such as the 2455 series of swabable valves. In other embodiments, the port 640 (and any of the ports described herein) need not be either a swabable connector or a needle-free port; any suitable port can be employed. In some embodiments, the port 640 can include a male or female luer fitting. In some embodiments, the port 640 can include a threaded connection for coupling with a syringe or a tubing set. In some embodiments, the port 640 can be sealed at the end for sterile docking or cutting.

Although the port 640 is shown as being coupled at the first end portion 603 of the storage container 600. In other embodiments, the port 640 (and any of the ports described herein) can be coupled at any location and to any portion of the storage container 600. For example, in some embodiments, the port 640 (and any of the ports described herein) need not be coupled to the first end portion 603 of the container 600, the port can be on the surface or another edge portion of the container 600. The port 640 (and any of the ports described herein) can be offset from a center line of the storage container 600. For example, in some embodiments, the port can be located at a corner of the container. In some embodiments, the port (and any of the ports described herein) can be coupled around a central portion of the container.

In some embodiments, the port 640 can include a filter. In some embodiments, the port 640 can include a Y-connector. The base of Y-connector near port can contain the filter. One end of Y-connector can be sealed. The other end of the Y-connector can be threaded port for syringe connection. This allows for both hospital uses (e.g., syringe connection to port) and lab uses (e.g., a sterile dockable connection to the port). In some embodiments, the material stored in the storage volume 601 does not or is limited in its ability to move through the port 640. This may be due to size, viscosity, or other characteristics. In such embodiment, the port can be filterless allowing processing material to move into or out of the storage volume 601 without regard to the material stored therein.

In some embodiments, in a first (or opened) configuration, one or more edges (e.g., edge 611) of the first layer 610 are spaced apart from one or more edges (e.g., edge 621) of the second layer 620 to define an opening 650 into the storage volume 601 of each of the storage container 600. The opening 650 can be of any suitable size to facilitate loading of the tissue, biological material and/or treatment (e.g., a tissue graft), as described herein. In some embodiments, the opening 650 can extend across a portion of the length of an end or a side of the storage container 600. In some embodiments, the opening 650 can extend across substantially all of the end or side of the storage container 600.

In the example shown in FIG. 6A, the opening 650 can extend across a face or layer 610 near the seal opposite port 640 (e.g., seal 663 or 653) of container 600 defined by the separation between edges 611 and 621. In one example, the opening 650 is defined by a slit in the first layer 610. This opening 650 can be larger than a ported opening, such as the port 640 discussed above. A larger opening can allow for input of a larger material (e.g., a tissue graft) into the storage volume 601. Although it is appreciated that other materials as discussed herein can additionally or alternatively be introduced through opening 650. After the material is introduced into volume 601, the opening 650 can be sealed by seal 652 (e.g., a heat seal, adhesive seal, etc.), thereby enclosing the storage volume 601. This allows for the loading of biologicals or other materials through the opening 650 opposite the port 640. Once loaded, the opening 650 is sealed. The seal can be performed by a heat seal, an adhesive, or other suitable methods. In some embodiments, a laser line guides seal. In some embodiments, seal 653 can also be applied to fully separate opening 650 from the adjacent storage volumes.

In some embodiments, the container 600 is suitable for segregating a single material into multiple portions. For example, the storage container 600 can include a sealable region 660, suitable to apply a seal 663 to separate the storage volume 601 into volume 601 and 602. In some embodiments, the seal 663 can be applied before the material has been introduced into volume 601 thereby defining volume 601 and 602 separately before the material is introduced. In some embodiments, one or more edges (e.g., edge 611) of the first layer 610 are spaced apart from one or more edges (e.g., edge 659) of the second layer 620 to define an opening 651 into the storage volume 602 of each of the storage container 600. The opening 651 can be of any suitable size to facilitate loading of the tissue, biological material and/or treatment (e.g., a tissue graft), as described herein. The opening 651 can be of any suitable size to facilitate loading of peripheral items such as labels, instruments, therapeutics, etc., as described herein. In some embodiments, the opening 651 can extend across a portion of the length of an end or a side of the storage container 600. In some embodiments, the opening 651 can extend across substantially all of the end or side of the storage container 600. In some embodiments, the opening 651 can extend across a face or layer 610 near edge 609 of the container 600 defined by the separation between edges 657 and 659. In another example, the opening 651 is defined by an unsealed portion of the layers 610 and 620 at edge 609. In another example, the opening 651 is defined by a slit in the layer 610. This opening can be larger than a ported opening, such as the port 640 discussed above. A larger opening can allow for input of a larger material (e.g., a tissue graft) into the storage volume 601. Although it is appreciated that other materials as discussed herein can additionally or alternatively be introduced through opening 651. After the material is introduced into volume 602, the opening 651 can be sealed by seal 669 (e.g., a heat seal, adhesive seal, etc.) enclosing the storage volume 602. This allows for the loading of materials through the opening 651 opposite the port 640. Once loaded, the opening 651 is sealed. The seal can be performed by a heat seal, an adhesive, or other suitable methods. In some embodiments, a laser line guides seal.

In some embodiments, the seal 663 can be applied after the material has been introduced through opening 650 or alternatively opening 651. In such embodiments, the storage volumes 601 and 602 would be defined after the material was introduced such that the two volumes could have identical material. The separation region 660 can include an indicia to tell operator loading material into container 600 where to apply the separation seal 663. When sealed at the indicia, the volume on a first side of the seal will have a first predetermined volume (e.g., storage volume 601) and the volume on the other side of the seal has a second predetermined volume (e.g., storage volume 602). In this way, one portion of the material (e.g., the material in volume 601) is usable for the intended process or operation while the other portion of the material (e.g., the material in volume 602) can be stored for subsequent use (e.g., quality control, testing, archiving, etc.) Separating the material into two portions allows for the second portion in volume to be a known sample that is the same as the first portion in volume 601 for exact match retention. In other words, the material within the storage volume 601 has identical properties as the material within the storage volume 602. In various embodiments, the second portion in the storage volume 602 is a quality control sample that is fully representative of the portion stored in volume 601. In some embodiments, the storage volume 601 is the larger volume as shown in FIG. 6B. Contrarily, in some embodiments, the storage volume is the larger volume. In this alternative, the larger volume 602 can be used for significant subsequent testing using more material than the actual procedure. The second portion can be stored and subsequently tested to show first portion meets certain criteria. In some embodiments, the second portion could be about 5 cc to about 50 cc volume.

In some embodiments, the sealable region 660 can include a frangible region 664. The frangible region 664 can be suitable to facilitate or initiate separation of volume 601 from volume 602. The frangible region 664 can include perforations, thinning of material, stress risers suitable to directional tearing, adhesive attached otherwise detached containers or any other suitable mechanism for separating storage volumes 601 and 602 of the storage container 600 from one another. In some embodiments, the frangible region 664 can include one or more perforations lines positioned between container storage volumes 601 and 602. For example, frangible region 664 can be located between seal 652 and 663. When the frangible regions are separated volume 602 is removable from the storage volume 601 without compromising the sealed structure of either volume. However, it will be appreciated that other shapes of the volumes, seals, and frangible regions are applicable as well.

In some embodiments, the first storage volume 601 and the second storage volume 602 can be the same general shape, or in other embodiments, they can be different shapes. For example, as shown in FIG. 6B, the storage volume 601 can be generally rectangular. The storage volume 602 can similarly be generally rectangular. As discussed, the storage volume 602 can be sealed after material or items have been added and without a port attached to the storage volume 602, port leaking can be avoided producing robust long-term storage. As shown in FIG. 6B, the first storage volume 601 can in some embodiments include the port 640 after separation from volume 662 allowing for the introduction and removal of fluids. The storage volume 602 can be dispensed by cutting.

Figure 7A:
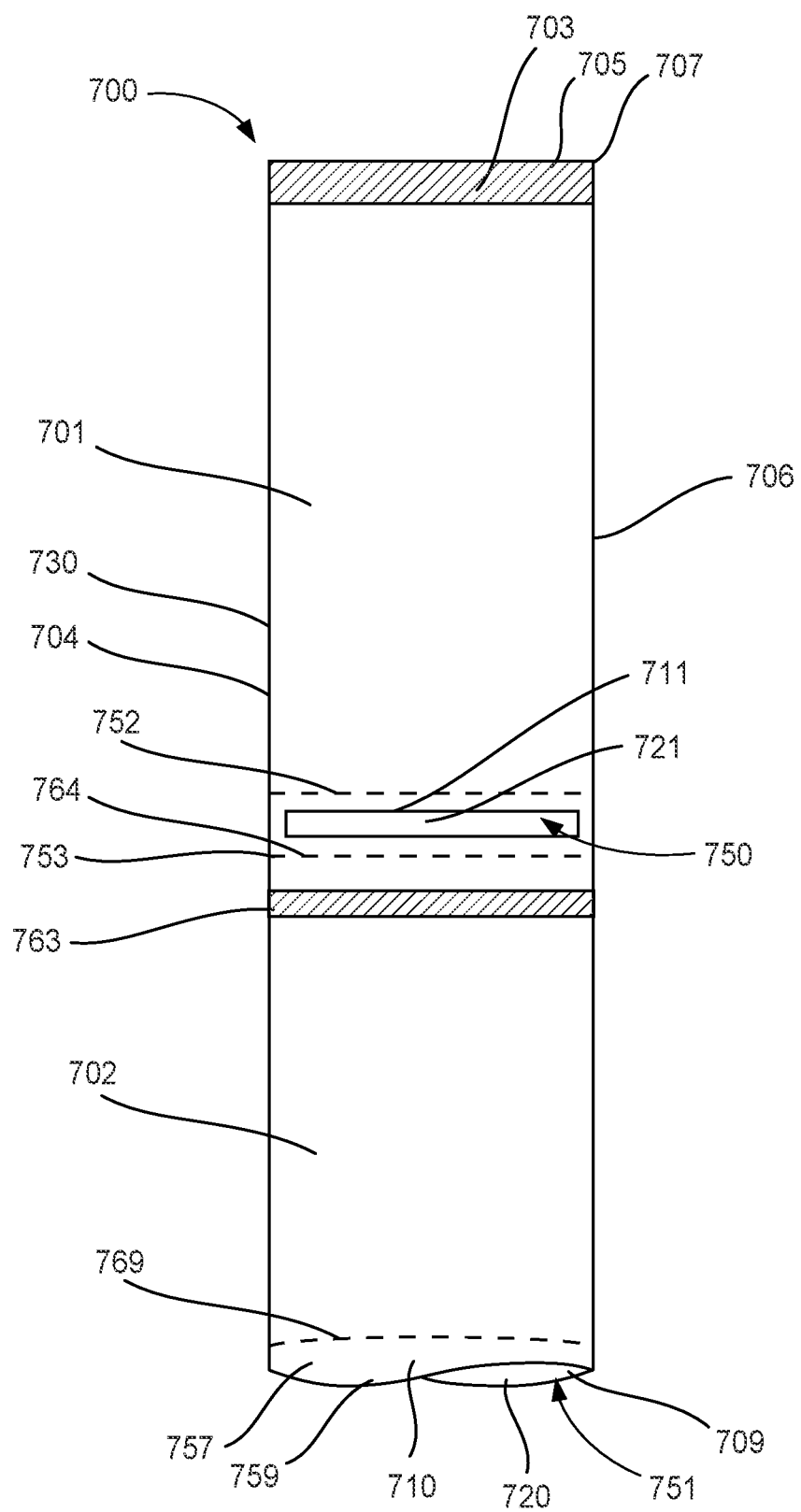
FIG. 7A is a schematic illustration of a storage container according to another embodiment in a first configuration.
Figure 7B:
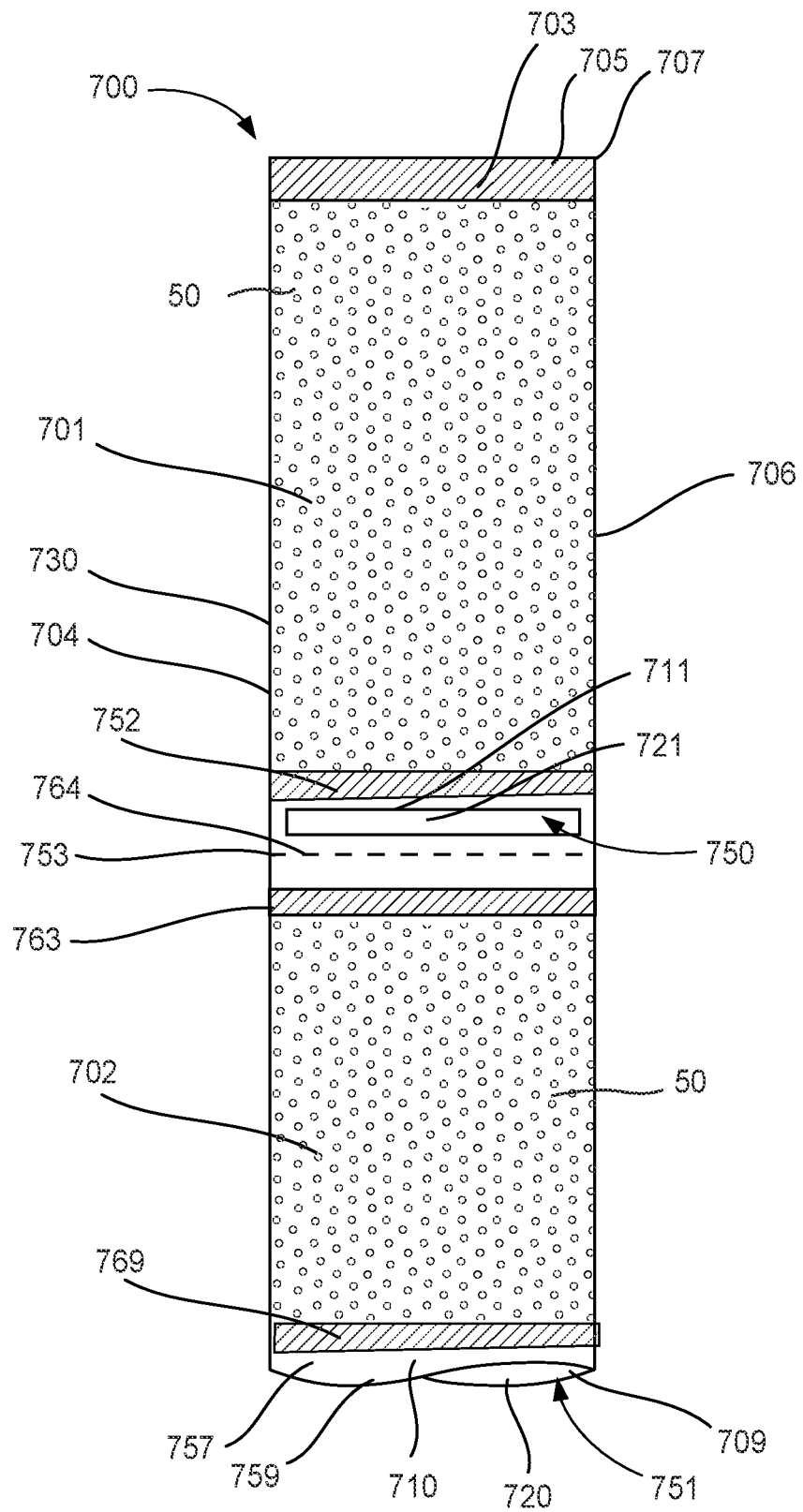
FIG. 7B is a schematic illustration of the storage container of FIG. 7A in a second configuration.

An embodiment of a storage container 700 is shown in FIGS. 7A-7B. The storage container 700 includes multiple storage volumes 701 and 702. The storage container 700 (and any of the container assemblies described herein) can include the storage volume 701 that can be used to store any of the tissue and biological materials described herein, and/or to perform any of the methods described herein, and/or the methods of preparing the material for use in a procedure. In some embodiments, the storage container 700 can include a storage volume 702 that can be used similarly to storage volume 701 to store any of the tissue and biological materials described herein, and/or to perform any of the methods described herein. Alternatively, the storage volume 702 can be used to store peripheral items such as labels (e.g., to identify the material in the storage volume 701), tools (e.g., to perform procedures with the material in the storage volume 701), therapeutic treatments (e.g., to supplement or use with the material in the storage volume 701), etc.

As described herein, the storage container 700 provides a container that can be used for cryogenically freezing, storage, transport, processing, cryogenically defrosting and/or rehydration of the material. The storage container 700 also includes a first layer 710, a second layer 720 and one or more seals 730 connecting the first layer 710 and the second layer 720. The one or more seals 730 form side edges 704, 706 of the storage container 700. While sealed edges can define the container 700, it is also appreciated that in some embodiments, the two layers (e.g., 710, 720) can be provided as tubular material that is flattened forming two longitudinal connections between the layers on the flattened longitudinal edges of the tubular material (e.g., layflat tubular film).

As shown in FIG. 7A, the storage container 700 includes one or more material ingresses and/or egresses. The storage container 700 can include a first opening (e.g., opening 750). The storage container 700 can also or alternatively include a second opening (e.g., edge opening 751). In some embodiments, such as the embodiment illustrated in FIG. 7A, the container 700 does not include a port. In some embodiments, the port is removeable, via the mechanisms described herein (e.g., the end portion seal and associated frangible region).

The two layers 710, 720 respectively are joined at a first end portion 703. For example, the two side edges 705, 707 are joined together. In such an embodiment, material can be inserted or additionally or alternatively treated (e.g., with a preservation fluid) via the opening 750 or 751.

In some embodiments, in a first (or opened) configuration, one or more edges (e.g., edge 711) of the first layer 710 are spaced apart from one or more edges (e.g., edge 721) of the second layer 720 to define an opening 750 into the storage volume 701 of each of the storage container 700. The opening 750 can be of any suitable size to facilitate loading of the tissue, biological material and/or treatment (e.g., a tissue graft), as described herein. In some embodiments, the opening 750 can extend across a portion of the length of an end or a side of the storage container 700. In some embodiments, the opening 750 can extend across substantially all of the end or side of the storage container 700.

In the example shown in FIG. 7A, the opening 750 can extend across a face or layer 710 near a seal (e.g., seal 763) of container 700 defined by the separation between edges 711 and 721. In one example, the opening 750 is defined by a slit in the first layer 710. A larger opening can allow for input of a larger material (e.g., a tissue graft) into the storage volume 701. Although it is appreciated that other materials as discussed herein can additionally or alternatively be introduced through the opening 750. After the material is introduced into the storage volume 701, the opening 750 can be sealed by the seal 752 (e.g., a heat seal, adhesive seal, etc.), thereby enclosing the storage volume 701. This allows for the loading of biologicals or other materials through the opening 750. Once loaded, the opening 750 is sealed. The seal can be performed by a heat seal, an adhesive, or other suitable methods. In some embodiments, a laser line guides seal. In some embodiments, the seal 753 can also be applied to fully separate the opening 750 from the adjacent storage volumes.

In some embodiments, the container is suitable for segregating a single material into multiple portions. For example, the storage container 700 can include a sealable region 760, suitable to apply a seal 763 to separate the storage volume 701 into volume 701 and 702. In some embodiments, the seal 763 can be applied before the material has been introduced into volume 701 thereby defining volume 701 and 702 separately before the material is introduced. In some embodiments, such as this one, the storage container 700 can include an opening 751 into volume 702. One or more edges (e.g., edge 757) of the first layer 710 are spaced apart from one or more edges (e.g., edge 759) of the second layer 720 to define an opening 751 into the storage volume 702 of each of the storage container 700. The opening 751 can be of any suitable size to facilitate loading of the tissue, biological material and/or treatment (e.g., a tissue graft), as described herein. The opening 751 can be of any suitable size to facilitate loading of peripheral items such as labels, instruments, therapeutics, etc., as described herein. In some embodiments, the opening 751 can extend across a portion of the length of an end or a side of the storage container 700. In some embodiments, the opening 751 can extend across substantially all of the end or side of the storage container 700. In some embodiments, the opening can extend across a face or layer 710 near edge 709 of container 700 defined by the separation between edges 757 and 759. In another example, the opening 751 is defined by an unsealed portion of the layers 710 and 720 at edge 709. In another example, the opening 751 is defined by a slit in the layer 710. A larger opening can allow for input of a larger material (e.g., a tissue graft) into the storage volume 701. Although it is appreciated that other materials as discussed herein can additionally or alternatively be introduced through opening 751. After the material is introduced into volume 702, the opening 751 can be sealed by seal 769 (e.g., a heat seal, adhesive seal, etc.) enclosing volume 702. This allows for the loading of materials through the opening 751. Once loaded, the opening 751 is sealed. The seal can be performed by a heat seal, an adhesive, or other suitable methods. In some embodiments, a laser line guides seal.

In some embodiments, the seal 763 can be applied after the material has been introduced through opening 750 or alternatively opening 751. In such embodiments, the storage volumes 701 and 702 would be defined after the material was introduced such that the two volumes could have identical material. The separation region 760 can include an indicia to tell operator loading material into container 700 where to apply the separation seal 763. When sealed at the indicia, the volume on a first side of the seal will have a first predetermined volume (e.g., storage volume 701) and volume on the other side of the seal has a second predetermined volume (e.g., storage volume 702). In this way, one portion of the material (e.g., the material in storage volume 701) is usable for the intended process or operation while the other portion of the material (e.g., the material in volume 702) can be stored for subsequent use (e.g., quality control, testing, archiving, etc.) Separating the material into two portions allows for second portion in volume 702 to be a known sample that is the same as the first portion in volume 701 for exact match retention. In other words, the material within the storage volume 701 has identical properties as the material within the volume 702. In various embodiments, second portion in the storage volume 702 is a quality control sample that is fully representative of the portion stored in volume 701. In some embodiments, the storage volume 701 is the larger volume as shown in FIG. 7B. Contrarily, in some embodiments, the storage volume 702 is the larger volume. In this alternative, the larger volume 702 can be used for significant subsequent testing using more material than the actual procedure. The second portion can be stored and subsequently tested to show first portion meets certain criteria. In some embodiments, the second portion could be about 5 cc to about 50 cc volume.

In some embodiments, the sealable region 760 can include a frangible region 764. The frangible region can be suitable to facilitate or initiate separation of volume 701 from volume 702. The frangible region 764 can include perforations, thinning of material, stress risers suitable to directional tearing, adhesive attached otherwise detached containers or any other suitable mechanism for separating storage volumes 701 and 702 of the storage container 700 from one another. In some embodiments, the frangible region 764 can include one or more perforations lines positioned between container storage volumes 701 and 702. For example, frangible region 764 can be located between seal 752 and 763. In another example, the frangible region can be located along one or more of seals 752, 753, or 763. When the frangible regions are separated volume 702 is removable from the storage volume 701 without compromising the sealed structure of either volume. However, it will be appreciated that other shapes of the volumes, seals, and frangible regions are applicable as well.

In some embodiments, the first volume 701 and the second volume 702 can be the same general shape, or in other embodiments, they can be different shapes. For example, as shown in FIG. 7B, volume 701 can be generally rectangular. Volume 702 can similarly be generally rectangular. As discussed, the storage volume 702 can be sealed after material or items have been added and without a port attached to the storage volume 702, port leaking can be avoided producing robust long-term storage. The storage volume 702 can be dispensed by cutting.

Figure 8A:
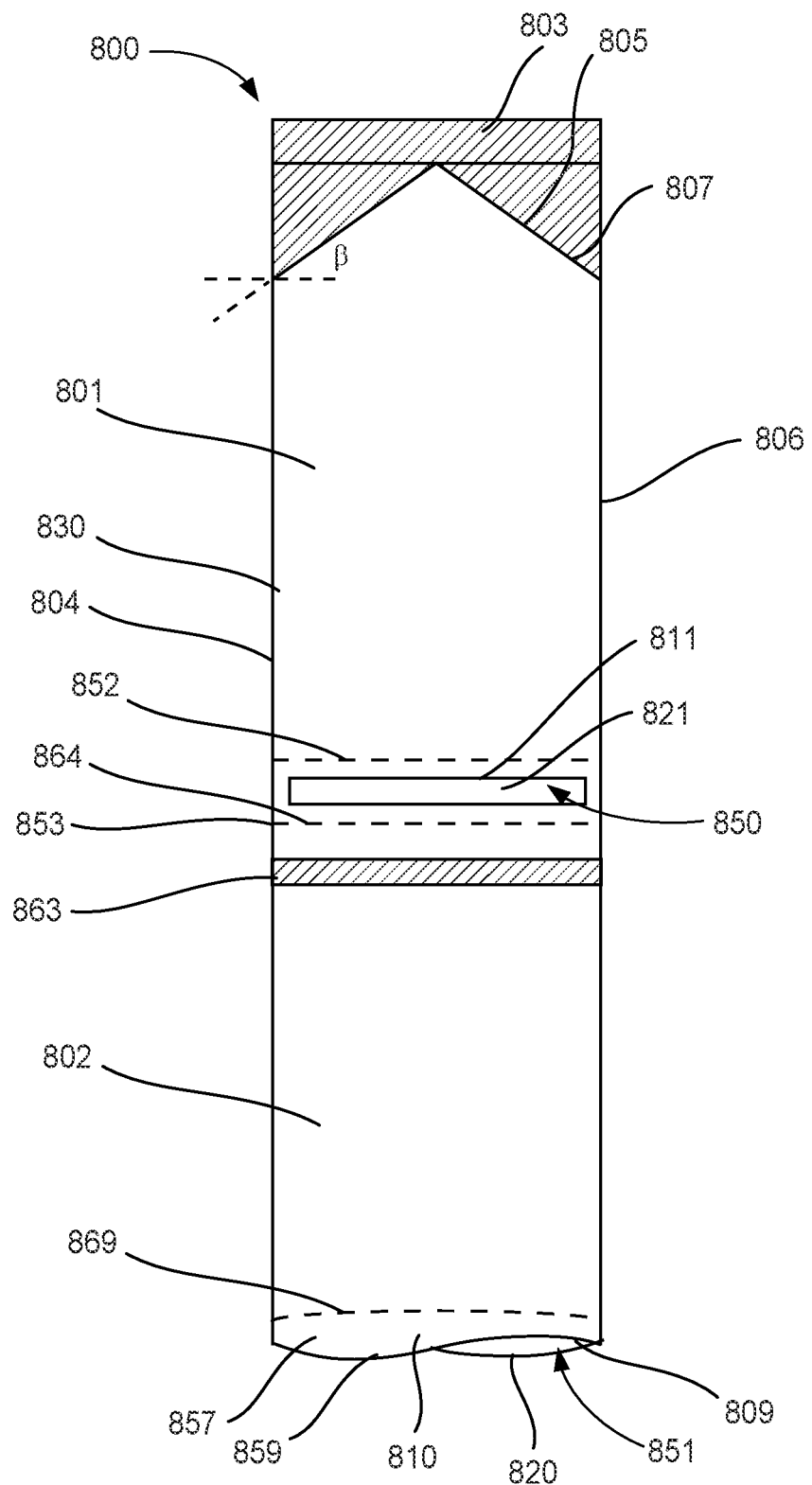
FIG. 8A is a schematic illustration of a storage container according to another embodiment in a first configuration.
Figure 8B:
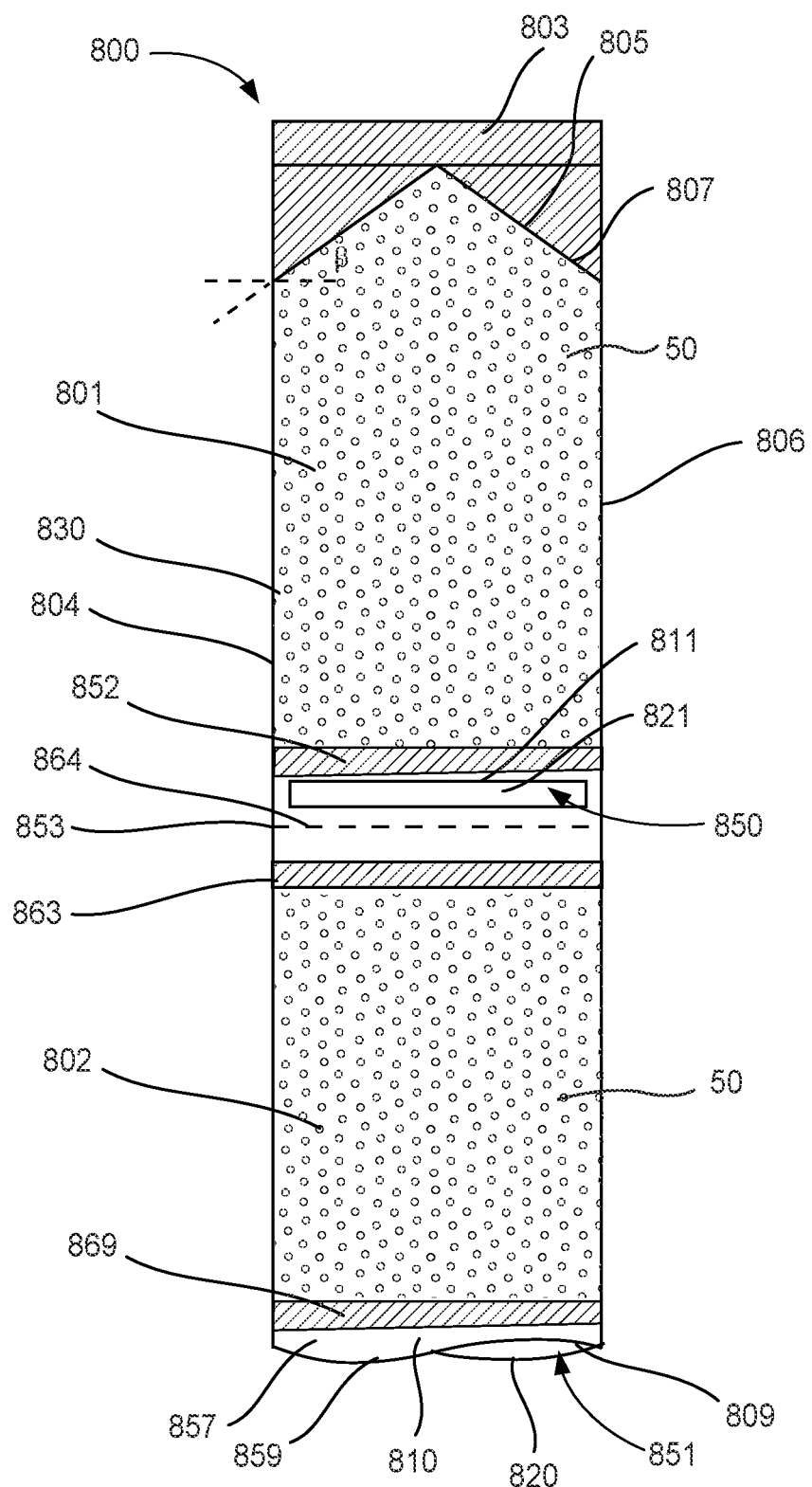
FIG. 8B is a schematic illustration of the storage container of FIG. 8A in a second configuration.

An embodiment of a storage container 800 is shown in FIGS. 8A-8B. The storage container 800 includes multiple storage volumes 801 and 802. The storage container 800 (and any of the container assemblies described herein) can include the storage volume 801 that can be used to store any of the tissue and biological materials described herein, and/or to perform any of the methods described herein, and/or the methods of preparing the material for use in a procedure. In some embodiments, the storage container 800 can include a storage volume 802 that can be used similarly to storage volume 801 to store any of the tissue and biological materials described herein, and/or to perform any of the methods described herein. Alternatively, storage volume 802 can be used to store peripheral items such as labels (e.g., to identify the material in 801), tools (e.g., to perform procedures with the material in 801), therapeutic treatments (e.g., to supplement or use with the material in 801), etc.

As described herein, the storage container 800 provides a container that can be used for cryogenically freezing, storage, transport, processing, defrosting and/or rehydration of the material. The storage container 800 also includes a first layer 810, a second layer 820 and one or more seals 830 connecting the first layer 810 and the second layer 820. The one or more seals 830 form side edges 804, 806 of the storage container 800. While sealed edges can define the container 800, it is also appreciated that in some embodiments, the two layers (e.g., 810, 820) can be provided as tubular material that is flattened forming two longitudinal connections between the layers on the flattened longitudinal edges of the tubular material (e.g., layflat tubular film).

As shown in FIG. 8A, the storage container 800 includes one or more material egresses. The storage container 800 can include a first opening (e.g., opening 850). The storage container 800 can also or alternatively include a second opening (e.g., edge opening 851). In some embodiments, such as the embodiment illustrated in FIG. 8A, the container 800 includes a peelable seal suitable for removing the contents from the container 800.

The two layers 810, 820 respectively are joined at a first end portion 803. For example, the two side edges 805, 807 are joined together. In such an embodiment, material can be inserted or additionally or alternatively treated (e.g., with a preservation fluid) via the opening 850 or 851.

In some embodiments, in a first (or opened) configuration, one or more edges (e.g., edge 811) of the first layer 810 are spaced apart from one or more edges (e.g., edge 821) of the second layer 820 to define an opening 850 into the storage volume 801 of each of the storage container 800. The opening 850 can be of any suitable size to facilitate loading of the tissue, biological material and/or treatment (e.g., a tissue graft), as described herein. In some embodiments, the opening 850 can extend across a portion of the length of an end or a side of the storage container 800. In some embodiments, the opening 850 can extend across substantially all of the end or side of the storage container 800. In the example shown in FIG. 8A, the opening can extend across a face or layer 810 near edge 808 of container 800 defined by the separation between edges 811 and 821. In one example, the opening 850 is defined by a slit in the first layer 810. A larger opening can allow for input of a larger material (e.g., a tissue graft) into the storage volume 801. Although it is appreciated that other materials as discussed herein can additionally or alternatively be introduced through opening 850. After the material is introduced into the storage volume 801, opening 850 can be sealed by seal 852 (e.g., a heat seal, adhesive seal, etc.), thereby enclosing the storage volume 801. This allows for the loading of biologicals or other materials through the opening 850. Once loaded, the opening 850 is sealed. The seal can be performed by a heat seal, an adhesive, or other suitable methods. In some embodiments, a laser line guides seal. In some embodiments, seal 853 can also be applied to fully separate opening 850 from the adjacent storage volumes.

In some embodiments, the container is suitable for segregating a single material into multiple portions. For example, the storage container 800 can include a sealable region 860, suitable to apply a seal 863 to separate the storage volume 801 into storage volumes 801 and 802. In some embodiments, the seal 863 can be applied before the material has been introduced into volume 801 thereby defining storage volume 801 and 802 separately before the material is introduced. In some embodiments, such as this one, the storage container 800 can include an opening 851 into volume 802. One or more edges (e.g., edge 857) of the first layer 810 are spaced apart from one or more edges (e.g., edge 859) of the second layer 820 to define an opening 851 into the storage volume 802 of each of the storage container 800. The opening 851 can be of any suitable size to facilitate loading of the tissue, biological material and/or treatment (e.g., a tissue graft), as described herein. The opening 851 can be of any suitable size to facilitate loading of peripheral items such as labels, instruments, therapeutics, etc., as described herein. In some embodiments, the opening 851 can extend across a portion of the length of an end or a side of the storage container 800. In some embodiments, the opening 851 can extend across substantially all of the end or side of the storage container 800. In some embodiments, the opening can extend across a face or layer 810 near edge 809 of container 800 defined by the separation between edges 857 and 859. In another example, the opening 851 is defined by an unsealed portion of the layers 810 and 820 at edge 809. In another example, the opening 851 is defined by a slit in the layer 810. A larger opening can allow for input of a larger material (e.g., a tissue graft) into the storage volume 801. Although it is appreciated that other materials as discussed herein can additionally or alternatively be introduced through opening 851. After the material is introduced into volume 802, the opening 851 can be sealed by seal 869 (e.g., a heat seal, adhesive seal, etc.) enclosing volume 802. This allows for the loading of materials through the open end 851. Once loaded, the open end 851 is sealed. The seal can be performed by a heat seal, an adhesive, or other suitable methods. In some embodiments, a laser line guides seal.

In some embodiments, the seal 863 can be applied after the material has been introduced through opening 850 or alternatively opening 851. In such embodiments, the storage volumes 801 and 802 would be defined after the material was introduced such that the two volumes could have identical material. The separation region 860 can include an indicium to tell operator loading material into container 800 where to apply the separation seal 863. When sealed at the indicia, the volume on a first side of the seal will have a first predetermined volume (e.g., storage volume 801) and volume on the other side of the seal has a second predetermined volume (e.g., storage volume 802). In this way, one portion of the material (e.g., the material in volume 801) is usable for the intended process or operation while the other portion of the material (e.g., the material in volume 802) can be stored for subsequent use (e.g., quality control, testing, archiving, etc.) Separating the material into two portions allows for second portion in volume 802 to be a known sample that is the same as the first portion in volume 801 for exact match retention. In other words, the material within the volume 801 has identical properties as the material within the storage volume 802. In various embodiments, second portion in the storage volume 802 is a quality control sample that is fully representative of the portion stored in the storage volume 801. In some embodiments, the storage volume 801 is the larger volume as shown in FIG. 8B. Contrarily, in some embodiments, the storage volume 802 is the larger volume. In this alternative, the larger volume 802 can be used for significant subsequent testing using more material than the actual procedure. The second portion can be stored and subsequently tested to show first portion meets certain criteria. In some embodiments, the second portion could be about 5 cc to about 50 cc volume.

In some embodiments, the sealable region 860 can include a frangible region 864. The frangible region can be suitable to facilitate or initiate separation of the storage volume 801 from the storage volume 802. The frangible region 864 can include perforations, thinning of material, stress risers suitable to directional tearing, adhesive attached otherwise detached containers or any other suitable mechanism for separating storage volumes 801 and 802 of the storage container 800 from one another. In some embodiments, the frangible region 864 can include one or more perforations lines positioned between container storage volumes 801 and 802. For example, frangible region 864 can be located between seal 852 and 863. In another example, the frangible region can be located along one or more of seals 852, 853, or 863. When the frangible regions are separated volume 802 is removable from the storage volume 801 without compromising the sealed structure of either volume. However, it will be appreciated that other shapes of the volumes, seals, and frangible regions are applicable as well.

In some embodiments, the first storage volume 801 and the second storage volume 802 can be the same general shape, or in other embodiments, they can be different shapes. For example, as shown in FIG. 8B, the storage volume 801 can be generally rectangular. The storage volume 802 can similarly be generally rectangular. As discussed, the storage volume 802 can be sealed after material or items have been added and without a port attached to storage volume 802, port leaking can be avoided producing robust long-term storage. The storage volume 802 can be dispensed by cutting.

As shown in FIG. 8B, the storage container 800 includes one or more material egresses. For example, the storage container 800 can also or alternatively include opening (e.g., peelable seal 868). In some embodiments, opening is a peelable seal 868. A portion of connection between the first layer 810 and the second layer 820 can be a peelable connection such that the dispensing at the peelable seal 868 includes areas in which the first layer 810 and the second layer 820 can be peeled apart after connection. The container 800 can include features of the various the containers as disclosed in U.S. Pat. No. 11,065,095 (the '095 patent, titled "Sample Container with Peelable Seal and Access Port," which is hereby incorporated by reference in its entirety. In light of the disclosure in the present application, a person of ordinary skill in the art could adapt the features of the container in the '095 patent to be formed on as a storage container having peel reseal openings similar to those disclosed in the '095 patent.

In various examples, the connection between the first layer 810 and the second layer 820 can be a peelable connection such that the region includes areas in which the first layer and the second layer can be peeled apart after connection. For example, in some embodiments, the peelable seal 868 can be an adhesive-based seal in which an adhesive layer pulls back from one of the first layer 810 or the second layer 820 when the first layer 810 is peeled apart from the second layer 820. In other embodiments, the peelable seal can be a cohesive seal in which an adhesive layer or intermediate layer fails within itself when the first layer 810 is peeled apart from the second layer 820. The peelable seal 868 can be produced by any suitable methods and/or mechanism as described herein. The seal and/or the layers 810, 820, whether peelable or permanent hermetically seals the storage volume 801. The peelable seal 868 can be of any suitable geometry to facilitate the desired peel direction, peel strength, and the like. For example, in some embodiments, the peelable seal 868 can be an angled seal that provides for peel tabs that can be grasped by the user to peel the first layer 810 from the second layer 820. In some embodiments, as illustrated in FIG. 8B, the peelable seal 868 can extend across the length and define the edge 805, 807. However, in other embodiments, the peelable seal 868 can extend across a portion of an edge. Because cutting and tearing can introduce foreign matter, the peelable opening allows for the contents inside to remain aseptic after opening the container 800. Additionally, the peel strength can be adjusted based on the material selected. In some examples, the peel strength is between 0.25 pounds and 5 pounds. In other examples, the peel strength is between 0.5 pounds and 2 pounds. In one example, the peel strength is about 1 pound. The peel can also control the amount of material dispensed. For example, how far the layers are peeled adjusts the opening size allowing more material to be dispensed relative to a smaller opening. The size can also be adjusted to the type of material being dispense. For example, a more viscous material can benefit from a larger opening. A less viscous material can benefit from a smaller opening.

The storage container 800 can include a tapered portion. The tapered portion can define a narrow egress that can be opened thereby allowing the storage volume 801 to be dispensed in a controlled manner. Without a port attached to storage volume 801, port leaking can be avoided producing robust long-term storage. The storage volume 801 can be dispensed by peeling the peelable seal 868. When the peelable seal 868 is peeled the material can be released or dispensed in a controlled manner during dispensing of the material in quality control operations. The peelable seal 868 can be defined by the region near the tapered portion. Edges 804 and 806 can extend in parallel until they taper together forming edges 803 and 805. In some embodiments, the seals along end portions 803 and/or 805 (or any other sealed edges forming a funnel described herein) can extend at an angle ($\beta$) of between about 5 degrees to about 75 degrees. This configuration allows for a large opening for loading (e.g., opening 850) and a controlled egress at the peelable seal 868 for dispensing.

Figure 9A:
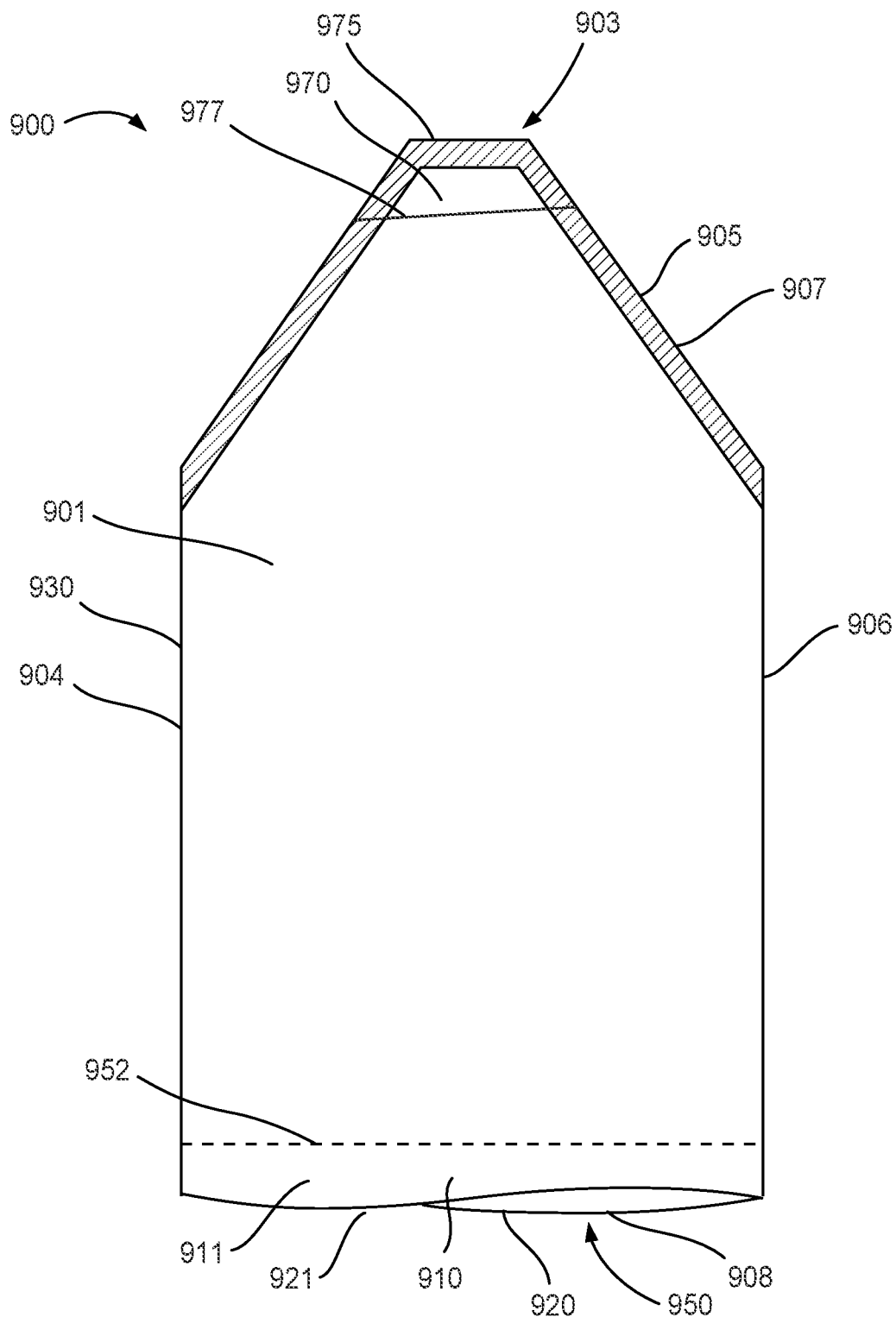
FIG. 9A is a schematic illustration of a storage container according to another embodiment in a first configuration.
Figure 9B:
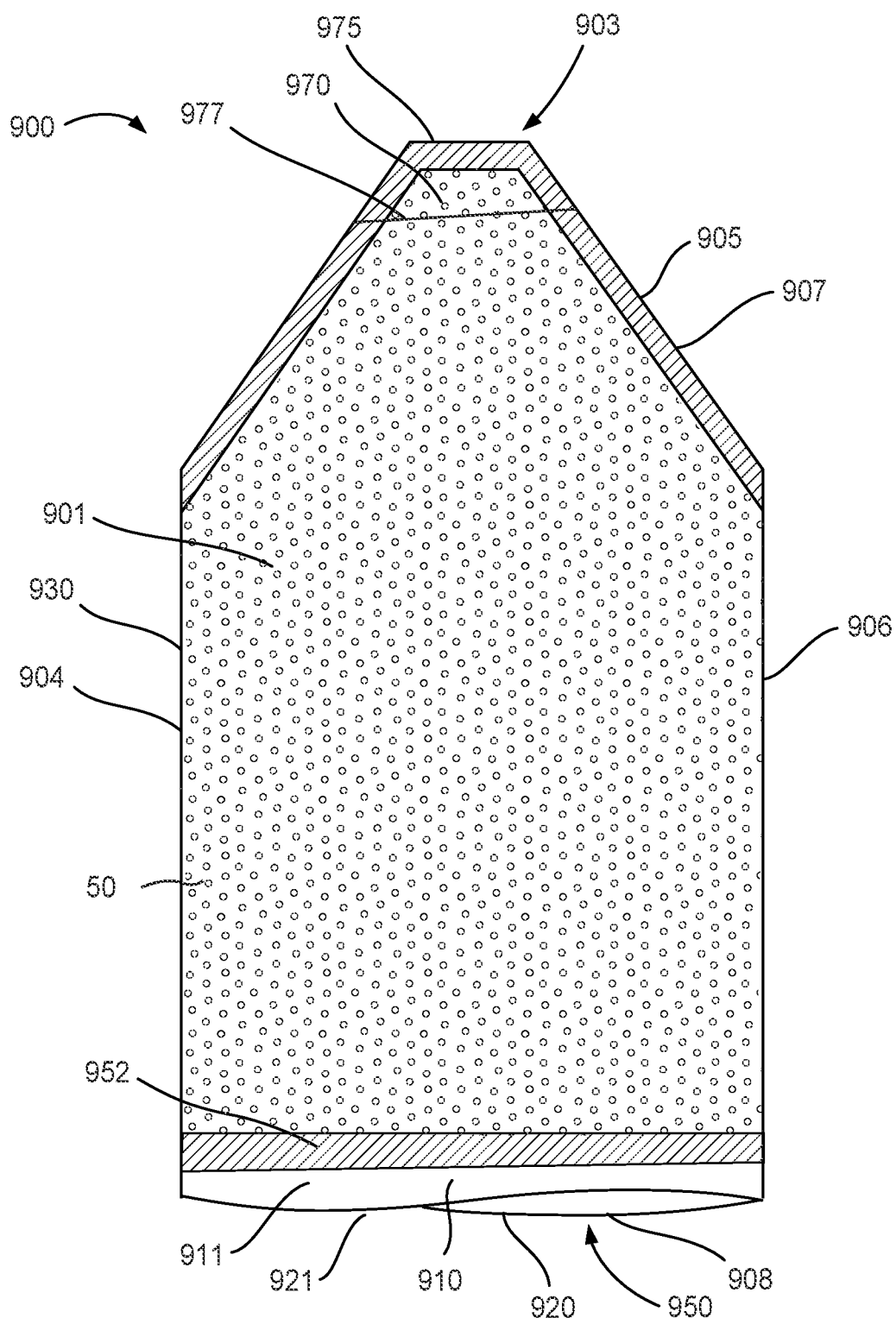
FIG. 9B is a schematic illustration of the storage container of FIG. 9A in a second configuration.

An embodiment of a storage container 900 is shown in FIGS. 9A-B. The storage container 900 includes a tapered end portion. The storage container 900 (and any of the container assemblies described herein) can include the storage volume 901 that can be used to store any of the tissue and biological materials described herein, and/or to perform any of the methods described herein and/or the methods of preparing the material for use in a procedure.

As described herein, the storage container 900 provides a container that can be used for cryogenically freezing, storage, transport, processing, defrosting and/or rehydration of the material. The storage container 900 also includes a first layer 910, a second layer 920 and one or more seals 930 connecting the first layer 910 and the second layer 920. The one or more seals 930 form side edges 904, 906 of the storage container 900. While sealed edges can define the container 900, it is also appreciated that in some embodiments, the two layers (e.g., 910, 920) can be provided as tubular material that is flattened forming two longitudinal connections between the layers on the flattened longitudinal edges of the tubular material (e.g., layflat tubular film).

As shown in FIG. 9A, the storage container 900 includes one or more material egresses. The storage container 900 can include a first opening (e.g., opening 950). The two layers 910, 920 respectively are joined at a first end portion 908. In such an embodiment, material can be inserted or additionally or alternatively treated (e.g., with a preservation fluid) via the opening 950.

In some embodiments, in a first (or opened) configuration, one or more edges (e.g., edge 911) of the first layer 910 are spaced apart from one or more edges (e.g., edge 921) of the second layer 920 to define an opening 950 into the storage volume 901 of each of the storage container 900. The opening 950 can be of any suitable size to facilitate loading of the tissue, biological material and/or treatment (e.g., a tissue graft), as described herein. In some embodiments, the opening 950 can extend across a portion of the length of an end or a side of the storage container 900. In the example shown in FIG. 9A, the opening 950 can extend across substantially all of the end or side of the storage container 900. In some embodiments, the opening can additionally or alternatively extend across a face or layer 910 near first end portion 908 of container 900 defined by the separation between edges 911 and 921. In one example, the opening 950 is defined by a slit in the layer 910. A larger opening can allow for input of a larger material (e.g., a tissue graft) into the storage volume 901. Although it is appreciated that other materials as discussed herein can additionally or alternatively be introduced through opening 950. After the material is introduced into the storage volume 901, the opening 950 can be sealed by seal 952 (e.g., a heat seal, adhesive seal, etc.) enclosing the storage volume 901. This allows for the loading of biologicals or other materials through the opening 950. Once loaded, the opening 950 is sealed. The seal can be performed by a heat seal, an adhesive, or other suitable methods. In some embodiments, a laser line guides seal.

The storage container 900 can include a tapered portion 903. The tapered portion 903 can define a narrow egress 970 that can be opened thereby allowing the storage volume 901 to be dispensed in a controlled manner. Without a port attached to the storage volume 901, port leaking can be avoided producing robust long-term storage. The storage volume 901 can be dispensed by egress 970. In various examples the egress can include a V-shaped end or tip 975. When the tip 975 is cut, the material can be released or dispensed in a controlled manner during dispensing of the material.

The egress 970 can be of any suitable geometry to facilitate or form the designed egress opening. For example, in some embodiments, the egress 970 can be an angled seal that funnels the material in volume 901 toward the tip 975. This taped end with angled seals along edges 905 and 907 allows for maximum material dispensing because there are limited regions for the material to get hung up on within the storage volume 901. In some embodiments, as illustrated in FIG. 9B, the egress 970 can extend across the width of the container 900 and define the edge 905, 907. However, in other embodiments, the egress 970 can extend across a portion of an edge. A cut indicia 977 can be provided on tip 975. For example, the cut indicia 977 can include a laser mark in layer 910 and/or 920 can be provided to position the correct cut or tear of the material. In some embodiments, this indicia 977 can also be a weakened area allowing for a directed and easier tear along the desired position. For example, the material may be thinned along the weakened area.

Figure 10A:
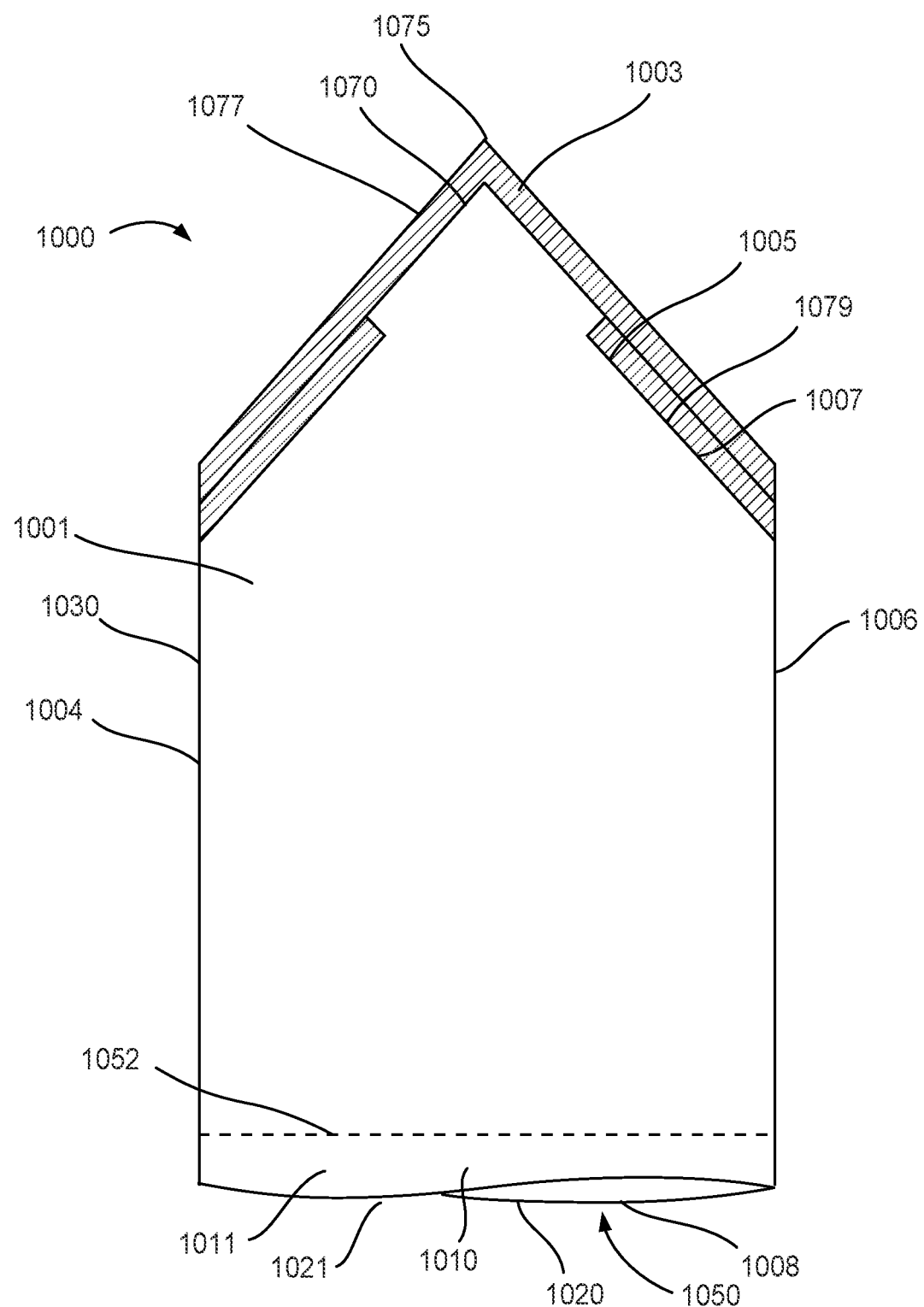
FIG. 10A is a schematic illustration of a storage container according to another embodiment in a first configuration.
Figure 10B:
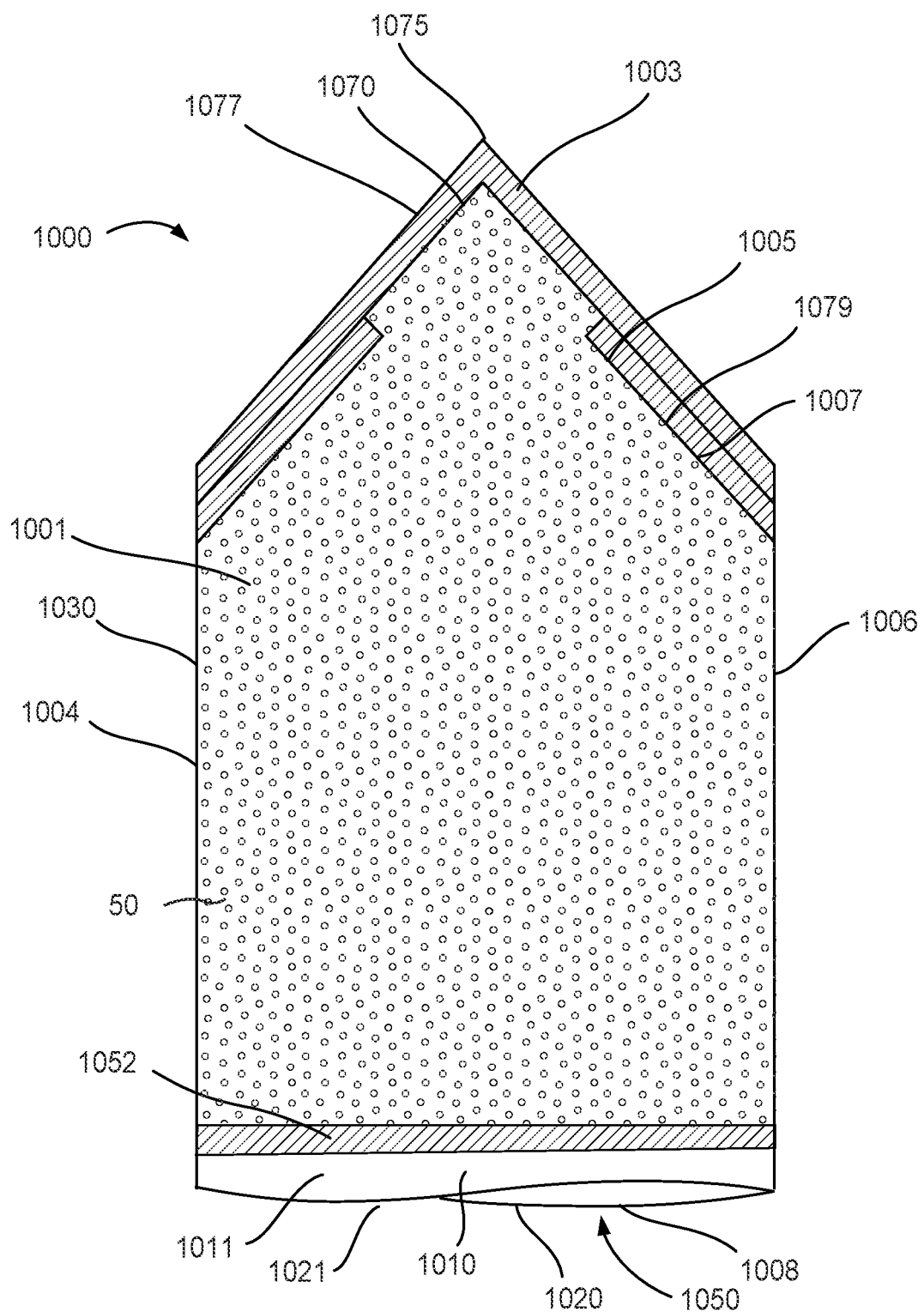
FIG. 10B is a schematic illustration of the storage container of FIG. 10A in a second configuration.

An embodiment of a storage container 1000 is shown in FIGS. 10A-B. The storage container 1000 includes a peelable tapered end portion. The storage container 1000 (and any of the container assemblies described herein) can include the storage volume 1001 that can be used to store any of the tissue and biological materials described herein, and/or to perform any of the methods described herein and/or the methods of preparing the material for use in a procedure.

As described herein, the storage container 1000 provides a container that can be used for cryogenically freezing, storage, transport, processing, cryogenically defrosting and/or rehydration of the material. The storage container 1000 also includes a first layer 1010, a second layer 1020 and one or more seals 1030 connecting the first layer 1010 and the second layer 1020. The one or more seals 1030 form side edges 1004, 1006 of the storage container 1000. While sealed edges can define the container 1000, it is also appreciated that in some embodiments, the two layers (e.g., 1010, 1020) can be provided as tubular material that is flattened forming two longitudinal connections between the layers on the flattened longitudinal edges of the tubular material (e.g., layflat tubular film).

As shown in FIG. 10A, the storage container 1000 includes one or more material egresses. The storage container 1000 can include a first opening (e.g., opening 1050). In such an embodiment, material can be inserted or additionally or alternatively treated (e.g., with a preservation fluid) via the opening 1050.

In some embodiments, in a first (or opened) configuration, one or more edges (e.g., edge 1011) of the first layer 1010 are spaced apart from one or more edges (e.g., edge 1021) of the second layer 1020 to define an opening 1050 into the storage volume 1001 of each of the storage container 1000. The opening 1050 can be of any suitable size to facilitate loading of the tissue, biological material and/or treatment (e.g., a tissue graft), as described herein. In some embodiments, the opening 1050 can extend across a portion of the length of an end or a side of the storage container 1000. In the example shown in FIG. 10A, the opening 1050 can extend across substantially all of the end or side of the storage container 1000. In some embodiments, the opening can additionally or alternatively extend across a face or layer 1010 near edge 1008 of container 1000 defined by the separation between edges 1011 and 1021. In one example, the opening 1050 is defined by a slit in the layer 1010. A larger opening can allow for input of a larger material (e.g., a tissue graft) into the storage volume 1001. Although it is appreciated that other materials as discussed herein can additionally or alternatively be introduced through opening 1050. After the material is introduced into the storage volume 1001, the opening 1050 can be sealed by seal 1052 (e.g., a heat seal, adhesive seal, etc.) enclosing volume 1001. This allows for the loading of biologicals or other materials through the opening 1050. Once loaded, the opening 1050 is sealed. The seal can be performed by a heat seal, an adhesive, or other suitable methods. In some embodiments, a laser line guides seal.

In some embodiments, the storage volume 1001 can be dispensed by egress 1070. In various examples the egress can include a V-shaped end or tip 1075. When the tip 1075 is opened, the material can be released or dispensed in a controlled manner during dispensing of the material. In some embodiments, the egress 1070 is a peelable seal. A portion of connection between the first layer 1010 and the second layer 1020 can be a peelable connection such that the egress 1070 includes areas 1078 in which the first layer 1010 and the second layer 1020 can be peeled apart after connection. The container 1000 can include features of the various the containers as disclosed in U.S. Pat. No. 11,065,095 (the '095 patent, titled "Sample Container with Peelable Seal and Access Port," which is already incorporated by reference in its entirety. In light of the disclosure in the present application, a person of ordinary skill in the art could adapt the features of the container in the '095 patent to be formed on as a storage container having peel reseal openings similar to those disclosed in the '095 patent.

In various examples, the connection between the first layer 1010 and the second layer 1020 can be a peelable connection such that the region includes areas in which the first layer and the second layer can be peeled apart after connection. For example, in some embodiments, the egress 1070 can include the peelable seal. The peelable sell can include an adhesive-based seal in which an adhesive layer pulls back from one of the first layer 1010 or the second layer 1020 when the first layer 1010 is peeled apart from the second layer 1020. In other embodiments, the peelable seal can be a cohesive seal in which an adhesive layer or intermediate layer fails within itself when the first layer 1010 is peeled apart from the second layer 1020. The egress 1070 can be produced by any suitable methods and/or mechanism as described herein. The seal and/or the layers 1010, 1020, whether peelable or permanent, hermetically seals the storage volume 1001. The egress 1070 can include a peelable seal. The egress 1070 can be of any suitable geometry to facilitate the desired peel direction, peel strength, and the like. For example, in some embodiments, the egress 1070 can be an angled seal that provides for peel tabs that can be grasped by the user to peel the first layer 1010 from the second layer 1020. In some embodiments, as illustrated in FIG. 10B, the egress 1070 can extend across the length and define the edge 1005, 1007. However, in other embodiments, the egress 1070 can extend across a portion of an edge. Because cutting and tearing can introduce foreign matter, the peelable opening allows for the contents inside to remain aseptic after opening the container 1000. Additionally, the peel strength can be adjusted based on the material selected. In some examples, the peel strength is between 0.25 pounds and 5 pounds. In other examples, the peel strength is between 0.5 pounds and 2 pounds. In one example, the peel strength is about 1 pound. The peel can also control the amount of material dispensed. For example, how far the layers are peeled apart adjusts the opening size allowing more material to be dispensed relative to a smaller opening. The size can also be adjusted to the type of material being dispense. For example, a more viscous material can benefit from a larger opening. A less viscous material can benefit from a smaller opening.

The container 1000 can include a tapered portion. The tapered portion can define a narrow egress that can be opened thereby allowing the storage volume 1001 to be dispensed in a controlled manner. Without a port attached to the storage volume 1001, port leaking can be avoided producing robust long-term storage. The storage volume 1001 can be dispensed by egress 1070. In various examples the egress can include a tip 1075. When the tip 1075 is opened, the material can be released or dispensed in a controlled manner during dispensing of the material.

The egress 1070 can be of any suitable geometry to facilitate or form the egress opening. In some embodiments, container 1000 can include a tapered portion. For example, the egress 1070 can be an angled seal 1077 and 1079 that funnels the material in volume 1001 toward the tip 1075. The angled seals 1077 and 1079 can be formed between edges 1005 and 1007 of layers 1010 and 1020. This egress 1070 can include a tapered end that allows for maximum material dispensing because there are limited regions for the material to get hung up on within the storage volume 1001. In some embodiments, as illustrated in FIG. 10B, the egress 1070 can extend across the width of the container 1000 and define the edge 1005, 1007. However, in other embodiments, the egress 1070 can extend across a portion of the width of the container.

Figure 11:
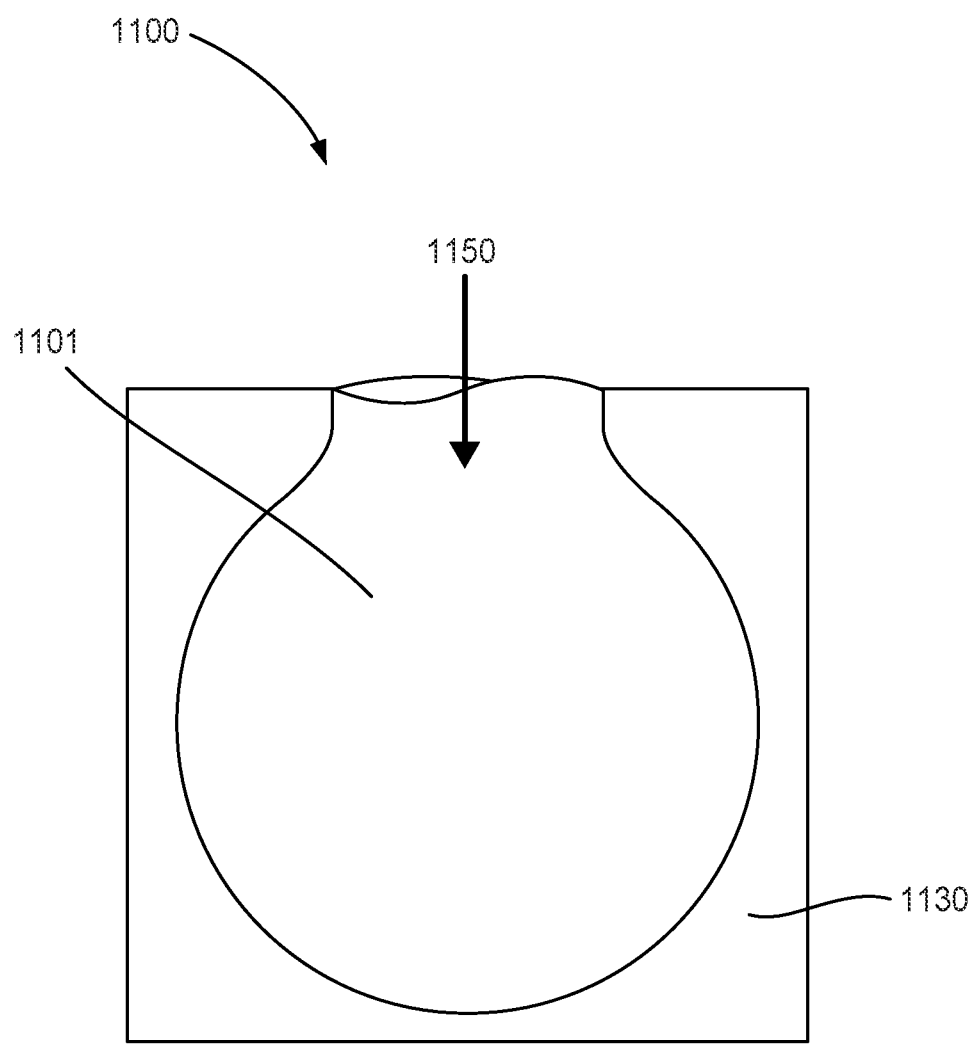
FIG. 11 is a schematic illustration of a storage container according to another embodiment.

Although the volumes of the containers (e.g., any of the layers in storage containers 100, 200, 300, 400, 500, 600, 700, 800, 900, and 1000) shown and described herein are depicted with rectangular or trapezoidal shapes, it is appreciated that the volumes can be formed between the first and second layers with any other desirable shapes. For example, as shown in FIG. 11, the volumes of the containers can include circular, oval, or U-shaped boundaries. The circular, oval, or U-shaped provides a rounded internal storage volume boundary that can provide a more compact storage area to keep stored material together, and/or prevent stored material from being trapped or retained in a corner portion while being removed from the storage volume. Additionally, the circular, oval, or U-shaped reduces stress risers by removing corners adding to the strength of the storage volume. The embodiment of a storage container 1100 is shown in FIG. 11. The storage container 1100 (and any of the container assemblies described herein) can include the storage volume 1101 that can be used to store any of the tissue and biological materials described herein, and/or to perform any of the methods described herein and/or the methods of preparing the material for use in a procedure. The storage container 1100 includes a seal 1130 that is continuously curved on the interior of the storage volume 1101. This curved profile limits stored material from being trapped or retained in any internal corner portions during storage of the stored material or during removal of the stored material from the storage volume 1101. Additionally, the circular, oval, or U-shaped reduces stress risers by omitting internal corner portions. While shown with an opening 1150 that tapers down to neck from the wider center portion of storage volume 1001, it should be appreciated that other embodiments can have a wider opening. For example, the opening can be as wide as the widest portion of the volume 1101.

Figure 12A:
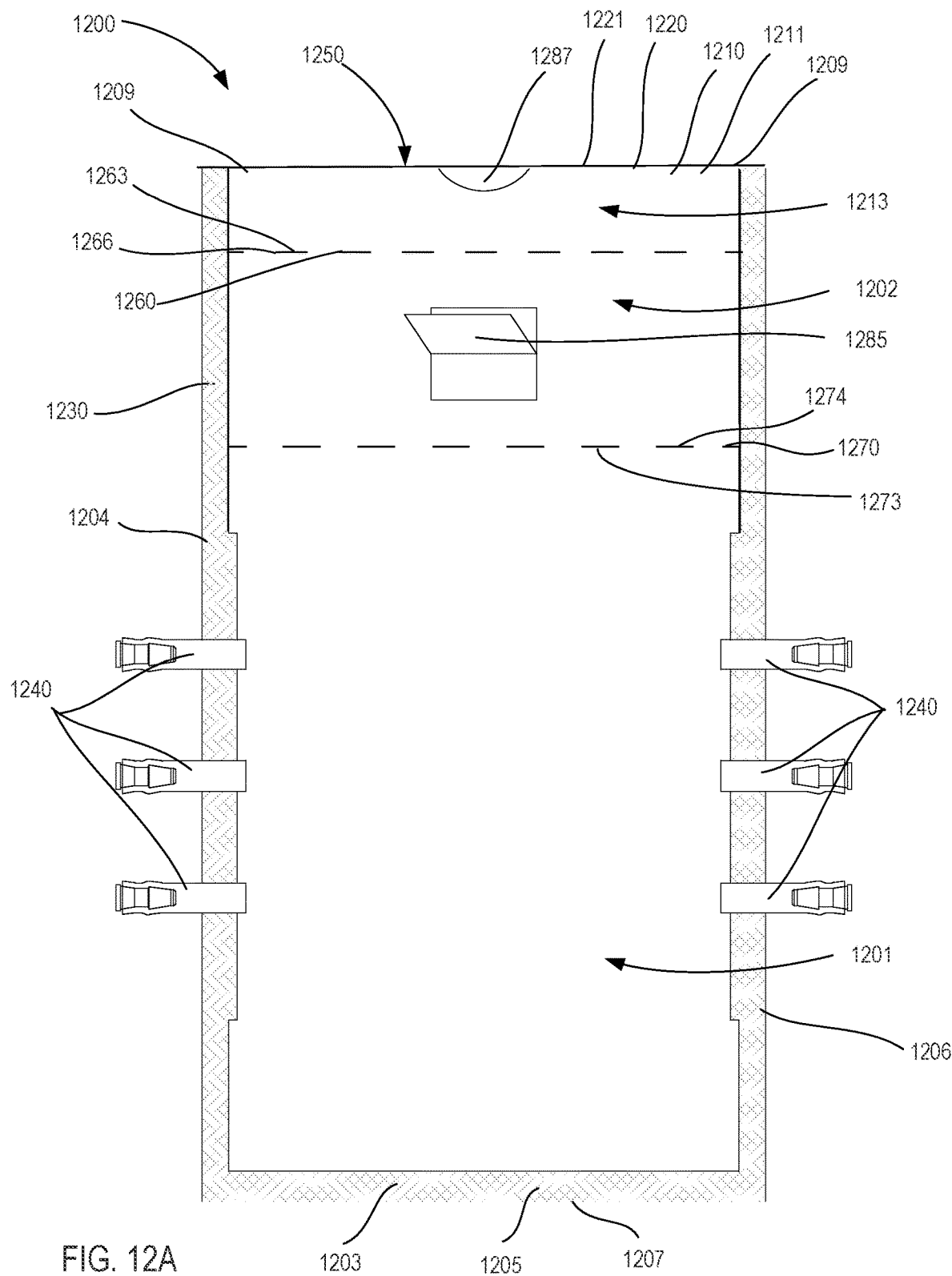
FIG. 12A is a schematic illustration of a storage container according to another embodiment.

An embodiment of a storage container 1200 is shown in FIG. 12A. The storage container 1200 can be configured to have multiple storage volumes 1201, 1202, and 1213. The storage container 1200 (and any of the container assemblies described herein) can include the storage volume 1201 that can be used to store any of the tissue and biological materials described herein, and/or to perform any of the methods described herein, and/or the methods of preparing the material for use in a procedure. In some embodiments, the storage container 1200 can include a storage volume 1202 that can be used similar to the storage volume 1201 to store any of the tissue and biological materials described herein, and/or to perform any of the methods described herein. Additionally or alternatively, the storage volume 1202 can be used as an interim material storage prior moving the material to the storage volume 1201. For example, if multiple units or pieces of tissue and/or biological material is to be stored in the storage container 1200, each unit or piece may be temporarily placed in the storage volume 1202 while the remaining units or pieces of material are retrieved. In this manner, the initial units and pieces of material placed within the storage volume 1202 are protected from external contaminates or debris while the remaining units or pieces are placed in the storage volume 1202. Additionally, the storage volume 1201 is maintained in a sterile condition during the loading of all the units or pieces of material into the storage volume 1202. Once all the units or pieces of material have been loaded into the storage volume 1202, the storage container 1200. In this way, the material can be sealed inside of the storage container 1200 before the storage volume 1201 is opened for moving the material into the storage volume 1201.

In some embodiments, the first storage volume 1201 is used to store a first kind of tissue and biological materials, and the second storage volume 1202 is used to store a second kind of tissue and biological materials, different from the first kind. In some embodiment, the first kind of tissue and biological materials can be mixed together with the second kind of tissue and biological materials prior to use. Alternatively, in some embodiments, the storage volume 1202 can be used to store peripheral items such as labels (e.g., to identify the material in 1201), tools (e.g., to perform procedures with the material in 1201), therapeutic treatments (e.g., to supplement or use with the material in 1201), etc. Alternatively, the storage volume 1213 can be used to store peripheral items such as labels (e.g., to identify the material in 1201), tools (e.g., to perform procedures with the material in 1201), therapeutic treatments (e.g., to supplement or use with the material in 1201), etc. Alternatively, the storage volume 1213 can remain unsealed to the outer environment.

As described herein, the storage container 1200 provides a container that can be used for cryogenically freezing, storage, transport, processing, defrosting and/or rehydration of the material. The storage container 1200 also includes a first layer 1210, a second layer 1220 and one or more seals 1230 connecting the first layer 1210 and the second layer 1220. The one or more seals 1230 form side edges 1204, 1206 of the storage container 1200. While sealed edges can define the storage container 1200, it is also appreciated that in some embodiments, the two layers (e.g., 1210, 1220) can be provided as tubular material that is flattened forming two longitudinal connections between the layers on the flattened longitudinal edges of the tubular material (e.g., layflat tubular film).

As shown in FIG. 12A, the storage container 1200 includes one or more material egresses. The storage container 1200 can include a first opening (e.g., opening 1250). The two layers 1210, 1220 respectively are joined at a first end portion 1203. For example, the two side edges 1205, 1207 are joined together. In such an embodiment, material can be inserted or additionally or alternatively treated (e.g., with a preservation fluid) via the opening 1250.

In some embodiments, in a first (or opened) configuration, one or more edges (e.g., edge 1211) of the first layer 1210 are spaced apart from one or more edges (e.g., edge 1221) of the second layer 1220 to define an opening 1250 into one or more of the storage volumes 1213, 1202, and 1201 of the storage container 1200. The opening 1250 can be of any suitable size to facilitate loading of the tissue, biological material and/or treatment (e.g., a tissue graft), as described herein. In some embodiments, the opening 1250 can extend across a portion of the length of an end or a side of the storage container 1200. In some embodiments, the opening 1250 can extend across substantially all of the end or side of the storage container 1200. A larger opening can allow for input of a larger material (e.g., a tissue graft) into the storage volume 1201. It is appreciated that other materials as discussed herein can additionally or alternatively be introduced through opening 1250. After the material is introduced into the storage volume 1202, opening 1250 can be sealed by seal 1252 (e.g., a heat seal, adhesive seal, etc.), thereby enclosing the storage volume 1201. This allows for the loading of biologicals or other materials through the opening 1250. Once loaded, the opening 1250 is sealable. The sealing of the opening 1250 (and the application of any other seals described herein) can be performed by a heat seal, an adhesive, or other suitable methods. In some embodiments, a laser line guides seal. In some embodiments, a seal 1263 can also be applied to fully separate opening 1250 from the adjacent storage volumes.

As shown in FIG. 12A, the storage container 1200 includes one or more material intermediate openings. For example, the storage container 1200 can include a first opening (e.g., port 1240). For example, as shown in FIG. 12A, the two layers 1210, 1220 respectively are joined at a first end portion 1203 and along the edges 1204 and 1206. In some embodiments, the one or more ports 1240 can be formed between the two layers 1210, 1220. In some embodiments, the ports 1240 can extend directly through a layer such as layer 1210 or 1220. In some embodiments, the ports 1240 can be coupled to the first end portion 1203 of the storage container 1200. The ports 1240 are configured to allow fluid communication between the outside of the storage container 1200 and the storage volume 1201. In this manner, additional material can be inserted and/or the material within the storage volume 1201 can be treated (e.g., with a preservation fluid) after being sealed within the storage container 1200. Additionally or alternatively, the port 1240 can also be coupled to a vacuum source to evacuate the storage volume. Additionally or alternatively, when in use (e.g., during a surgical procedure), the port 1240 can allow for cryogenically defrosting the material. Additionally or alternatively, when in use (e.g., during a surgical procedure), the port 1240 can allow for inflow of fluid used in rehydration or other uses. Additionally or alternatively, when in use, the port 1240 can allow for removal of fluid. In some embodiments, one set of ports 1240, such as those along edge 1206 can be used to convey a fluid into the storage volume 1201, while another set of ports, such as those along edge 1204 can be used to remove the fluid from the storage volume 1201.

The port 1240 can be any suitable port that selectively provides fluid communication to the storage volume 1201. For example, the port 1240 can include a tube, a valve, and/or a cap. In some embodiments, the port 1240 can be a needle-free port. In some embodiments, the port 1240 can be a swabable connector. Similarly stated in some embodiments, the port 1240 can have external surfaces and can be devoid of recesses or crevices such that the port 1240 can be easily wiped or "swabbed" to maintain sterility during use. In some embodiments, the port 1240 can include any of the barbed, swabable valves produced by the Halkey-Roberts Corporation, such as the 2455 series of swabable valves. In other embodiments, the port 1240 (and any of the ports described herein) need not be either a swabable connector or a needle-free port; any suitable port can be employed. In some embodiments, the port 1240 can include a male or female luer fitting. In some embodiments, the port 1240 can include a threaded connection for coupling with a syringe or a tubing set. In some embodiments, the port 1240 can be sealed at the end for sterile docking or cutting.

Although the port 1240 is shown as being coupled along the side edges 1204 and 1206 of the storage container 1200, the ports can be located in other locations. In other embodiments, the port 1240 (and any of the ports described herein) can be coupled at any location and to any portion of the storage container 1200. For example, in some embodiments, the port 1240 (and any of the ports described herein) need not be coupled to the side edges 1204 and 1206 of the storage container 1200, the port can be on the surface or another edge portion of the storage container 1200. For example, in some embodiments, the port can be located at a corner of the storage container 1200. In some embodiments, the port (and any of the ports described herein) can be coupled around a central portion of the storage container 1200.

In some embodiments, the port 1240 can include a filter. In some embodiments, the port 1240 can include a Y-connector. The base of Y-connector near port can contain the filter. One end of Y-connector can be sealed. The other end of the Y-connector can be threaded port for syringe connection. This allows for both hospital uses (e.g., syringe connection to port) and lab uses (e.g., a sterile dockable connection to the port). In some embodiments, the material stored in the storage volume 1201 does not, or is limited in its ability to, move through the port 1240. This may be due to size, viscosity, or other characteristics. In such embodiment, the port can be filterless allowing processing material to move into or out of the storage volume 1201 without regard to the material stored therein.

In some embodiments, the storage container 1200 is suitable for segregating a single material into multiple portions. For example, the storage container 1200 can include a sealable region 1260, suitable to apply a seal 1263 to separate the storage volume 1201 and 1202 from volume 1213. Additionally or alternatively, the sealable region can have a separable seal applied along seal 1266. The seal 1266 can be separated, then the material can be inserted into the volumes 1201, 1202 and then seal 1263 can be applied to sealable region 1260. Formation of the seal 1263 seals off the volumes 1201, 1202 from the exterior environment of the storage container 1200.

In some embodiments, the storage container 1200 is suitable for segregating a single material into multiple portions. For example, the storage container 1200 can include a sealable region 1270, suitable to apply a seal 1273 (also referred to as a separation seal) to separate the storage volume 1201 from volume 1202. Additionally or alternatively, the sealable region can have a separable seal applied along seal 1276. The seal 1276 can be separated allowing layers 1210 and 1220 to separate from one another opening volume 1201 to volume 1202. Then, the material can be inserted into the volumes 1201. Subsequently, the seal 1273 can be applied to sealable region 1270. Formation of seal 1273 separates the volume 1201 from the volume 1202.

In some embodiments, the seal 1273 can be applied after the material has been introduced into volume 1201. In such embodiments, the storage volumes 1201 and 1202 would be defined after the material is introduced. In some embodiments, some material can be moved to volume 1201 while some material remains in volume 1202 such that the two volumes could have identical material. The separation region 1270 can include an indicia to tell operator loading material into container 1200 where to apply the separation seal 1273. When sealed at the indicia, the volume on a first side of the seal will have a first predetermined volume (e.g., storage volume 1201) and volume on the other side of the seal has a second predetermined volume (e.g., storage volume 1202). In this way, one portion of the material (e.g., the material in volume 1201) is usable for the intended process or operation while the other portion of the material (e.g., the material in volume 1202) can be stored for subsequent use (e.g., quality control, testing, archiving, etc.) Separating the material into two portions allows for storage of the same material in both volume 1201 and volume 1202. In other words, the material within the volume 1201 has identical properties as the material within the storage volume 1202. In this manner, one portion of the material can be used or test without disturbing the second portion and therefore the second portion of material maintains sterility and can be used for a subsequent procedure or future testing. In various embodiments, second portion in the storage volume 1202 is a quality control sample that is fully representative of the portion stored in the storage volume 1201. In some embodiments, the storage volume 1201 is the larger volume as shown in FIG. 12A. Contrarily, in some embodiments, the storage volume 1202 is the larger volume. In this alternative, the larger volume 1202 can be used for significant subsequent testing using more material than the actual procedure. The second portion can be stored and subsequently tested to show first portion meets certain criteria. In some embodiments, the second portion could be about 5 cc to about 50 cc volume.

In some embodiments, the first storage volume 1201 and the second storage volume 1202 can be the same general shape, or in other embodiments, they can be different shapes. For example, as shown in FIG. 12A, the storage volume 1201 can be generally rectangular. The storage volume 1202 can similarly be generally rectangular. As discussed, the storage volume 1202 can be sealed after material or items have been added and without a port attached to storage volume 1202. Port leaking can be avoided producing robust long-term storage. The storage volume 1202 can be dispensed by cutting.

Figure 12B:
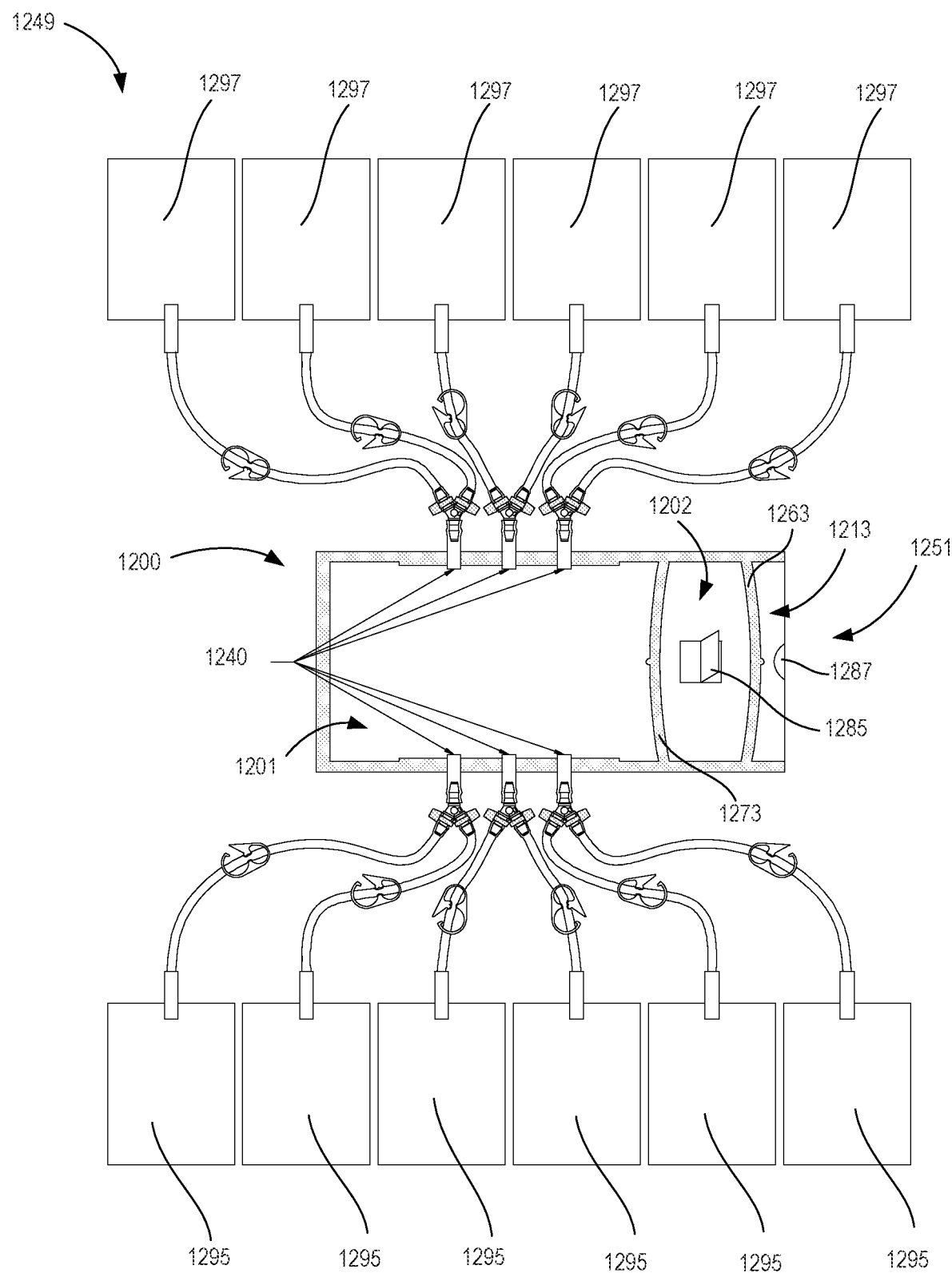
FIG. 12B is a schematic illustration of a material preparation system including the of the storage container of FIG. 12A in accordance with one embodiment.

In some embodiments, the storage container 1200 includes a separation member 1285. For example, one or both layers 210 and 220 can include the separation member 1285. The separation member 1285 can be located in the same region as the storage volume 1202. The separation member is operable for applying an external force to the storage container 1200 to pull the layers 210 and 220 apart to more easily pass the material through the volume 1202 into the volume 1201. In one example, as shown in FIGS. 12A and 12B, the separation member includes tabs that extend away from the external surface of layers 210 and 220. The tabs can be grippable by the hand of a user or the figures or a user to apply the outward force. Utilization of the separation member 1285 reduces the intrusion of possibly non-sterile equipment, hands, figures, or other items into the storage container 1200 to cause the separation, thereby increasing the overall sterility of the inside of the storage container 1200.

In some embodiments, the storage container 1200 includes an end separation member 1287. The end separation member facilitates easier initial separation of layers 1210 and 1220. In one example, the end separation member 1287 includes a notch extending through the surface of layer 1210. The notch allows for a section of layer 1210 that does not overlap layer 1220 allowing for easy access to layer 1220 such that the layers can be separation proximal to their end termination.

FIG. 12B is a schematic illustration of the storage container 1200 utilized in a material preparation system 1249 in accordance with some embodiments. The material preparation system 1249 can include one or more port injectable fluids 1295 connected to one or more of the ports 1240. The port injectable related media can include any of a variety of substances such as culture media, saline solution, cryoprotectant, preservation solution, etc. Additionally or alternatively, the material preparation system 1249 can include one or more fluid egress containers 1297 connected to one or more of the ports 1240. The media can be injected though a first set of ports 1240 and then evacuated through a second set of ports.

In some embodiments, seal 1273 can be applied after the material in volume 1201 has be exposed to the media via ports 1240. In such an embodiment, a portion of the material can remain in volume 1202 after the exposure to the media. Once sealed off, the material in the volume 1202 functions as a quality control sample preserved apart from the media of the volume 1201.

As described above, the storage container 1200 can be used to temporarily hold multiple units or pieces of materials (e.g., tissues and/or biological materials) during an extraction or loading process before the multiple units or pieces of materials are sealed within the storage container 1200 for storage. The temporarily holding volume promotes greater sterility within the storage container 1200. In some embodiments, the storage container 1200 may be pre-formed with the seal 1263 and the seal 1273 to provide a sterility entry area between the seal 1263 and the seal 1273. In such an embodiment, the seal 1263 is opened and one or more pieces of material is introduced into the volume 1202. The seal 1263 is then replaced or re-applied at the same or similar location to close the sterility entry area. Seal 1273 is then separated opening volume 1202 up to volume 1201. In some embodiments, an external force can be applied to separation members 1285 separating layers 1210 and 1220 from one another and breaking the seal 1273. The material can then be moved from the sterility entry area and into the volume 1201. In some embodiments, the seal 1273 is then replaced or re-applied at the same or similar location thereby sealing the material in the volume 1201 and separating it from the volume 1202. In some embodiments, a portion of the material can be kept within the volume 1202 (prior to replacing or reapplying the seal 1273) thereby allowing the volume 1202 to serve as a quality control container and/or providing the storage container 1200 with two volumes 1201, 1202 with the same material such that the two volumes of material can be used independent of one another without contaminating or affecting the sterility of the other volume of material.

Figure 12C:
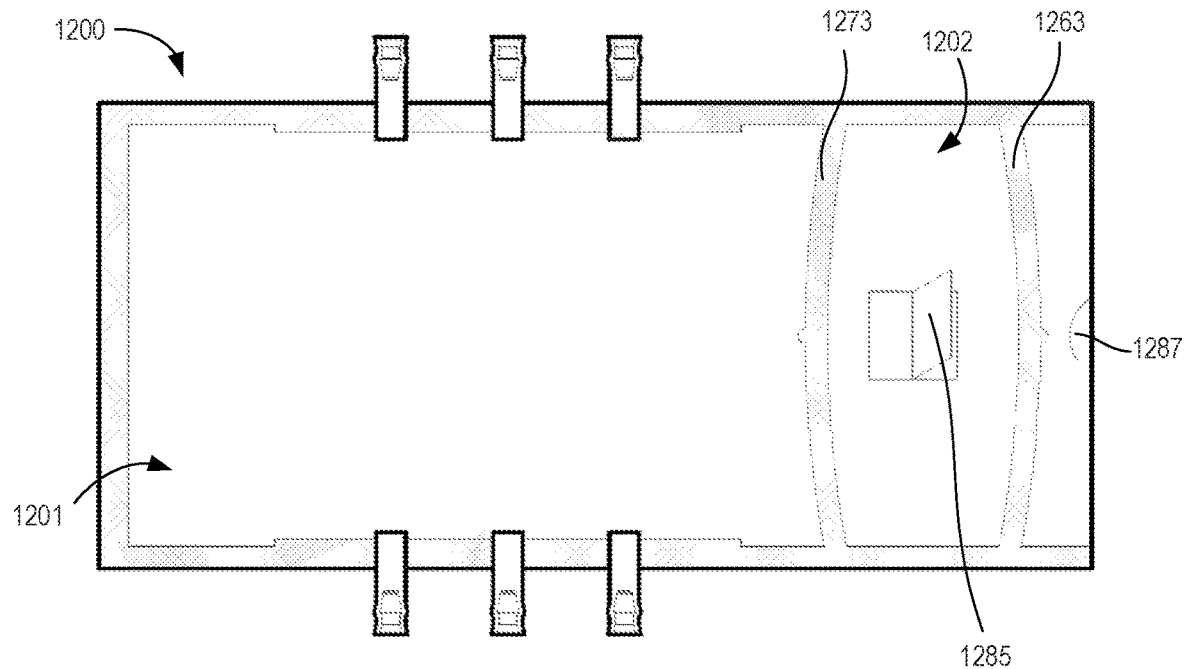
FIG. 12C is a schematic illustration of a storage container according to another embodiment.
Figure 12D:
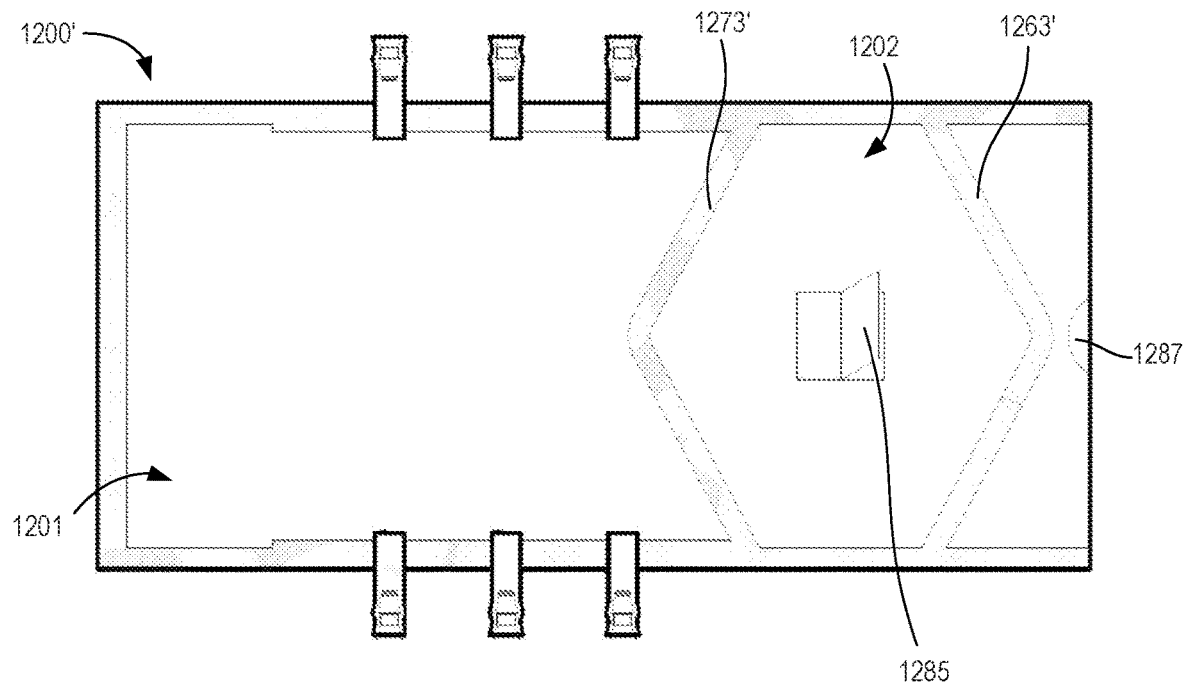
FIG. 12D is a schematic illustration of a storage container according to another embodiment.
Figure 12E:
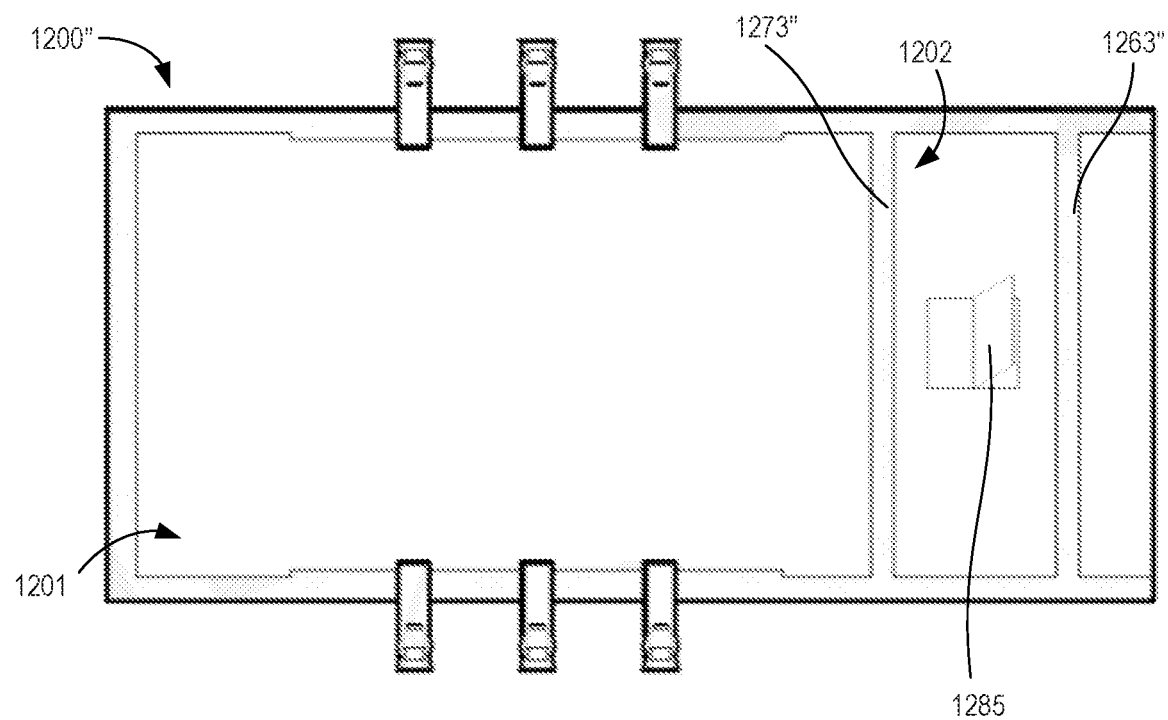
FIG. 12E is a schematic illustration of a storage container according to another embodiment.

FIG. 12C shows the storage container 1200 with the seal 1263 and the seal 1273 applied. In some embodiments, one or more of the seals 1263, 1273 form a concave inner wall bounding the volume 1202. FIG. 12D shows a storage container 1200', which is similar to the storage container 1200, except that the volume 1202 is bounded by one or more V-shaped inner walls formed by the seals 1263', 1273'. FIG. 12E shows a storage container 1200", which is similar to the storage container 1200, except that the volume 1202 is bounded by one or more linear inner walls formed by the seals 1263", 1273". Although the thickness of the seals (1263, 1263', 1263", 1273, 1273', 1273") are shown as having a constant width (or having a constant wall thickness), it will be appreciated the seals (and therefore the thickness of the walls formed by the seals) can have a variable width. For example, seals (1263, 1263', 1263", 1273, 1273', 1273", or any other seals described herein) can be provided with variable widths to promote separation (such as by using the separation member 1285) and/or to provide additional structural support in certain areas of the storage container 1200.

It should further be appreciated that any of the storage volumes described herein (including any of the storage volumes associated with storage containers 100, 200, 300, 400, 500, 600, 700, 800, 900, 1000, 1100 and 1200) can include circular, oval, or U-shaped internal boundaries.

The first and second layers (e.g., any of the layers in storage containers 100, 200, 300, 400, 500, 600, 700, 800, 900, 1000, 1100, and 1200) can be constructed of any suitable material. The first layer can have a first stiffness and the second layer can have a second stiffness. In some embodiments, the stiffnesses of the first layer and the second layer are the same. In some embodiments the stiffnesses are different. In some embodiments the second stiffness is greater than the first stiffness. In some embodiments, the first stiffness is greater than the second stiffness. In some embodiments, the layers can be constructed from the same material. In some embodiments, the layers can be constructed from a different material. In some embodiments, the layers can have different stiffness. In some embodiments, the first layer can be a thin, peelable film. The first layer can have any suitable thickness to provide the desired strength, flexibility, and sealing characteristics. For example, in some embodiments, the first layer 1110 can be between about 10 microns (0.010 mm) and about 2000 microns (2.0 mm). In some embodiments, the first layer 1110 can be between about 50 microns (0.050 mm) and about 200 microns (0.200 mm). In some embodiments, the first layer can be between about microns (0.050 mm) and about 1000 microns (0.100 mm). The second layer can have any suitable thickness to provide the desired strength, flexibility, and sealing characteristics. For example, in some embodiments, the first layer can be between about 10 microns (0.010 mm) and about 2000 microns (2.0 mm). In some embodiments, the second layer 1120 can be between about 50 microns (0.050 mm) and about 200 microns (0.200 mm). In other embodiments, the second layer 1120 can be between about 50 microns (0.050 mm) and about 1000 microns (0.100 mm).

In some embodiments, the layers (e.g., any of the layers in storage containers 100, 200, 300, 400, 500, 600, 700, 800, 900, 1000, 1100, and 1200) can be produced out of any one or more of the following materials: polyethylene (PE), low density polyethylene (LDPE), composites of LDPE, linear low-density polyethylene (LLDPE), high density poly ethylene (HDPE), polychlorotrifluoroethylene (PCTFE), ethylene tetrafluoroethylene (ETFE), polytetrafluoroethylene (PTFE), fluorinated ethylene propylene (FEP), polyurethane, polyimides (coats or non-coated), polyvinyl chloride (PVC), perfluoroalkoxy alkane (PFA), ethylene-vinyl acetate (EVA), polyvinylidene fluoride or polyvinylidene difluoride (PVDF), THV (a polymer of tetrafluoroethylene, hexafluoropropylene and vinylidene fluoride), PFE (Poly (fluorenylene ethynylene)), nylon, and/or composite of nylon. In some embodiments, any of the packaging using the materials above can be co-extruded and/or laminated. In some embodiments, any of the multi-chamber packaging using the materials above can further include aluminum foil laminate, aluminum oxide laminate, or laminated or co-extruded with aluminum oxide. In some embodiments, any of the multi-chamber packaging can be laminated with a layer of alder or any other suitable adhesive. The materials from which the first layer and the second layer are selected to ensure that the two layers can be joined to hermetically seal the storage volume within which the material (or any other stored product described herein) is stored while also retaining the desired flexibility. The two layers can be joined together at the end portions and along the side edges by any suitable methods and/or mechanism, such as, for example, by heat bonding or by an adhesive.

In some embodiments, the closing seals of the containers (e.g., storage containers 100, 200, 300, 400, 500, 600, 700, 800, 900, 1000, 1100, and 1200) are a permanent seal that is openable by destroying the seal and/or the layers. In other embodiments, the closing seals are peelable seals that are openable by separating the first layer from the second layer with a force that is less than a force required to tear or rip a material of the first layer and/or the second layer apart when sealed. The peelable seal can be configured to have any suitable failure (or peel) mechanism and can be of any suitable peel strength. In some embodiments, any of the containers (e.g., any of storage containers 100, 200, 300, 400, 500, 600, 700, 800, 900, 1000, 1100, and 1200) described herein can be produced using a plasma treatment, and/or a corona treatment.

While some embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

Although some embodiments have been described as having particular features and/or combinations of components, other embodiments are possible having a combination of any features and/or components from any of embodiments as discussed above. Aspects have been described in the general context of medical devices, and more specifically tissue packaging devices, but inventive aspects are not necessarily limited to use in medical devices and tissue packaging.

What is claimed is:

1. A system, comprising:
   a first layer;
   a second layer, the first layer and second layer being coupled together to form a container having a first end portion, a second end portion, a first edge between the first end portion and the second end portion, and a second edge between the first end portion and the second end portion, the first edge opposite the second edge;
a plurality of seals coupling the first layer and the second layer together along at least the first end portion, the second end portion, the first edge, or the second edge to define a storage volume between the first layer and the second layer;
a first opening into the storage volume, the first opening being positioned at the first end portion, the first opening being suitable to receive a material;
at least one intermediate seal extending between the first edge and the second edge, the at least one intermediate seal separating the storage volume into a first volume and a second volume, the intermediate seal being applicable after a target material is introduced into the storage volume such that the target material is stored within the first volume and the second volume; and
a frangible region extending along the at least one intermediate seal, the frangible region allowing for physical separation of the container into a first container portion and a second container portion, the first container portion including the first volume and the second container portion including the second volume, the second container portion including a tapered portion that extends from an end of the second edge to a tip at the second end portion,
wherein the plurality of seals coupling the first layer and the second layer includes a peelable seal at the tip, the peelable seal is configured such that the first layer can be peeled away from the second layer to produce a second opening at the tip.

2. The system of claim 1, wherein the frangible region includes any of a perforation, a tear notch, or a stress concentration riser.

3. The system of claim 2, wherein the frangible region includes a first perforation defined in the first layer and a second perforation defined in the second layer, the first perforation aligned with the second perforation.

4. The system of claim 1, wherein a width of the intermediate seal is greater than a width of the frangible region.

5. The system of claim 1, wherein a first seal of the plurality of seals is along the first edge and a second seal of the plurality of seals is along the second edge.

6. The system of claim 1, further comprising a port positioned along the first end portion, the port defining the opening.

7. The system of claim 6, wherein:
the first end portion includes an end portion seal that fluidically isolates the port from the storage volume; and
an end portion frangible region extending along the end portion seal, the end portion frangible region allowing for physical separation of the port from the storage volume.

8. The system of claim 1, wherein the frangible region is configured to allow removal of the tapered portion while maintaining the plurality of seals of the first container portion and the second container portion.

9. The system of claim 1, wherein the first volume and the second volume are partially defined by at least one of the plurality of seals and the intermediate seal completes a closure across the one of the plurality of seals to fully isolate the first volume and the second volume from one another.

10. The system of claim 1, wherein the first volume is larger than the second volume.

11. The system of claim 1, wherein the first volume is more than twice a size of the second volume.

12. The system of claim 1, wherein both the first volume and the second volume include regions that are openable to remove the target material from each of the first volume and the second volume.

13. The system of claim 12, wherein the first volume includes a port and the second volume includes a peelable region.

14. The system of claim 1, wherein the second container portion includes a plurality of graduated markings that indicate a quantity of the target material stored therein.

15. The system of claim 1, wherein:
the first container portion includes a first indicium associated with the target material; and
the second container portion includes a second indicium associated with at least one of the first indicium, the first container portion, or the target material.

16. The system of claim 15, wherein the first indicium and the second indicium are each machine readable.

17. The system of claim 1, wherein at least one of the first layer or the second layer include a separation tab extending from an exterior portion of the first layer or the second layer and oriented such that a user can grip the separation tab and separate the first layer from the second layer.

* * * * *